US011485795B2

(12) United States Patent
Tsun et al.

(10) Patent No.: US 11,485,795 B2
(45) Date of Patent: Nov. 1, 2022

(54) ANTI-PCSK9 ANTIBODY AND USE THEREOF

(71) Applicant: INNOVENT BIOLOGICS (SUZHOU) CO., LTD., Jiangsu (CN)

(72) Inventors: Andy Tsun, Jiangsu (CN); Eric Krauland, Jiangsu (CN); Jonathan P Belk, Jiangsu (CN); Xiaoniu Miao, Jiangsu (CN); Min Zhang, Jiangsu (CN); Nadthakarn Boland, Jiangsu (CN); Xiaolin Liu, Jiangsu (CN); Dechao Yu, Jiangsu (CN)

(73) Assignee: INNOVENT BIOLOGICS (SUZHOU) CO., LTD, Jiangsu (CN)

( * ) Notice: Subject to any disclaimer, the term of this patent is extended or adjusted under 35 U.S.C. 154(b) by 215 days.

(21) Appl. No.: 16/473,245

(22) PCT Filed: Dec. 22, 2017

(86) PCT No.: PCT/CN2017/118050
§ 371 (c)(1),
(2) Date: Jun. 24, 2019

(87) PCT Pub. No.: WO2018/113781
PCT Pub. Date: Jun. 28, 2018

(65) Prior Publication Data
US 2020/0087416 A1    Mar. 19, 2020

(30) Foreign Application Priority Data
Dec. 24, 2016 (CN) .......................... 201611210645.3

(51) Int. Cl.
*C07K 16/40* (2006.01)
*A61P 3/06* (2006.01)
*A61K 39/395* (2006.01)
*A61K 45/06* (2006.01)

(52) U.S. Cl.
CPC .......... *C07K 16/40* (2013.01); *A61K 39/3955* (2013.01); *A61K 45/06* (2013.01); *A61P 3/06* (2018.01); *C07K 2317/21* (2013.01); *C07K 2317/24* (2013.01); *C07K 2317/92* (2013.01)

(58) Field of Classification Search
None
See application file for complete search history.

(56) References Cited

U.S. PATENT DOCUMENTS

| 5,648,237 | A  | 7/1997  | Carter         |
|-----------|----|---------|----------------|
| 5,789,199 | A  | 8/1998  | Joly et al.    |
| 5,840,523 | A  | 11/1998 | Simmons et al. |
| 6,171,586 | B1 | 1/2001  | Lam et al.     |
| 6,267,958 | B1 | 7/2001  | Andya et al.   |
| 8,030,457 | B2 | 10/2011 | Jackson et al. |
| 8,062,640 | B2 | 11/2011 | Sleeman et al. |
| 8,080,243 | B2 | 12/2011 | Liang et al.   |
| 2009/0142352 | A1 | 6/2009 | Jackson et al. |
| 2009/0246192 | A1 | 10/2009 | Condra et al. |
| 2010/0166768 | A1 | 7/2010 | Sleeman et al. |
| 2022/0062416 | A1 | 3/2022 | Wang et al. |

FOREIGN PATENT DOCUMENTS

| CN | 103717237 A | 4/2014 |
| CN | 105001336 A | 10/2015 |
| CN | 105348390 A | 2/2016 |
| CN | 105801701 A | 7/2016 |
| CN | 106084058 A | 11/2016 |
| CN | 107261139 A | 10/2017 |
| EP | 0404097 A2 | 12/1990 |
| TW | 201946659 A | 12/2019 |
| WO | 1993/01161 A1 | 1/1993 |
| WO | 2005/103081 A2 | 11/2005 |
| WO | 2006/044908 A2 | 4/2006 |
| WO | 2008/105797 A2 | 9/2008 |
| WO | 2009/026558 A1 | 2/2009 |
| WO | 2009/036379 A2 | 3/2009 |
| WO | 2010/029513 A2 | 3/2010 |
| WO | 2010/077854 A1 | 7/2010 |
| WO | 2010/105256 A1 | 9/2010 |
| WO | 2012/009568 A2 | 1/2012 |
| WO | 2012/065072 A2 | 5/2012 |
| WO | 2012154999 A1 | 11/2012 |
| WO | 2013/016648 A2 | 1/2013 |
| WO | 2013/166448 A1 | 11/2013 |
| WO | 2015/200438 A1 | 12/2015 |
| WO | 2018/113781 A1 | 6/2018 |

(Continued)

OTHER PUBLICATIONS

Vajdos et al. (J Mol Biol. Jul. 5, 2002;320(2):415-28 (Year: 2002).*
Brown et al. (J Immunol. May 1996;156(9):3285-91 (Year: 1996).*
Mateu et al. (Mateu MG, et. al. Eur J Immunol. Jun. 1992;22(6):1385-9.) (Year: 1992).*
Greenspan et al. (Greenspan NS, Di Cera E. Defining epitopes: It's not as easy as it seems. Nat Biotechnol. Oct. 1999;17(10):936-7.) (Year: 1999).*
Examination Report No. 1 in Australian application No. 2017379048, dated Apr. 23, 2020.
Examination Report in Canadian application No. 3,047,049, dated Sep. 15, 2020.

(Continued)

*Primary Examiner* — Brian Gangle
*Assistant Examiner* — Andrea K McCollum
(74) *Attorney, Agent, or Firm* — Leason Ellis LLP

(57) ABSTRACT

The present invention provides an antibody that specifically binds to proprotein convertase subtilisin/kexin type 9 (PCSK9), an antigen-binding fragment of the antibody, and a composition comprising the antibody or the fragment. Also provided are a nucleic acid that encodes the antibody or the fragment, a host cell containing the nucleic acid, and applications of the antibody and fragment in treatment and diagnosis.

29 Claims, 15 Drawing Sheets

Specification includes a Sequence Listing.

(56) References Cited

FOREIGN PATENT DOCUMENTS

WO 2018/156741 A1 8/2018

OTHER PUBLICATIONS

Extended European Search Report in EP Application No. 17883464. 4, dated Nov. 19, 2020.
Center For Drug Evaluation And Research: "Pharmacology Review: REPATHA (evolocumab)", Aug. 20, 2015, pp. 1-80.
Manal Alkindi et al: "Monoclonal Antibodies for the Treatment of Hypercholesterolemia: Targeting PCSK9", Canadian Journal of Cardiology., vol. 32, No. 12, May 3, 2016, pp. 1552-1560.
Cormac Sheridan: "Phase 3 data for PCSK9 inhibitor wows", Nature Biotechnology, vol. 31, Dec. 6, 2013, pp. 1057-1058.
Rudikoff S et al : "Single amino acid substitution altering antigen-binding specificity", Proceedings of the National Academy of Sciences, National Academy of Sciences, vol. 79, No. 6, Mar. 1, 1982, pp. 1979-1983.
Stephan Duebel ED—Stefan Dubel: "Handbook of Therapeutic Antibodies Chapter 6", Jan. 1, 2007, Handbook ofTherapeutic Antibodies, Wiley-VCH. Weinheim, pp. 119-144.
S. Kuhnast et al: "Alirocumab inhibits atherosclerosis, improves the plaque morphology, and enhances the effects of a statin", Journal of Lipid Research, vol. 55, No. 10, Oct. 1, 2014, 2103-2112.
Toth Peter P ED, Chilton Robert: "Novel Therapies for Low Density Lipoprotein Cholesterol Reduction", American Journal of Cardiology, Cahners Publishing Co., Newton, MA, US, 2016, vol. 118, No. 6.
Zhao et al. Guidelines for the Prevention and Treatment of Dyslipidemia in Chinese Adults (2016 Revised Edition). Chinese Circulatory Journal, 2016, 31(10): 937-953.
Latimer et al. PCSK9 inhibitors in the prevention of cardiovascular disease. Journal of Thrombosis and Thrombolysis, 2016, 42(3):405-419.
Blom et al. PCSK9 inhibition in the management of hyperlipidemia: focus on evolocumab. Vascular Health and Risk Management, 2016, 12:185-197.
US prescribing information of Evolocumab dated Aug. 2015.
US prescribing information of Alirocumab dated Jul. 2015.
Zhang et al., "Pathogenic gene mutation in patients with familial hypercholesterolemia and premature coronary heart disease", Journal of Chinese Practical Diagnosis and Therapy, 2015, 29(6):549-552.
Zhang et al., "The Clinical Characteristics of Cardiovascular Involvement in Patients With Familial Hypercholesterolemia", Chinese Circulation Journal 2015, 29(5):327-330.
Hu et al., "The status of Chinese prevention and treatment of dyslipidemia", Chinese Journal of Internal Medicine, 2009, 29(1):2-4.
Li et al, "The levels and distribution of the serum lipids in Chinese adults, 2010". China J. of Prev. Med. 2012, 46(7):607-612.
Li et al, "Epidemologic characteristics of dyslipidemia in Chinese adults, 2010", China J. of Prev. Med. 2012, 46(5):414-418.
Li et al, "Awareness rate, treatment rate and control rate of dyslipidemia in Chinese adults, 2010", China J. of Prev. Med. 2012, 46(8):687-691.
Report On Cardiovascular Diseases in China (2014) National Center for Cardiovascular Diseases, China.
Neil et al. "Reductions in all-cause, cancer, and coronary mortality in statin-treated patients with heterozygous familial hypercholesterolaemia: a prospective registry study". European Heart Journal. 2008, 29(21):2625-2633.
Raal et al. "Expanded-dose simvastatin is effective in homozygous familial hypercholesterolaemia". Atherosclerosis. 1997, 135(2):249-256.
Watts et al. "Integrated guidance on the care of familial hypercholesterolaemia from the International FH Foundation". International Journal of Cardiology 2014, 171(3):309-325.

Nordestgaard et al. "Familial hypercholesterolaemia is underdiagnosed and undertreated in the general population guidance for clinicians to prevent coronary heart disease". European Heart Journal. 2013, 34(45):3478a-3490a.
Careskey et al. "Atorvastatin increases human serum levels of proprotein convertase subtilisin/kexin type 9". Journal of Lipid Research, 2008, 49(2):394-398.
World Preview 2014, Outlook to 2020. EvaluatePharma 2014.
Partial European Search Report in EP Application No. 17883464.4, dated Jul. 17, 2020.
International Search Report and Written Opinion in PCT/CN2019/086388, dated Aug. 15, 2019.
Waters et al., Lipid Treatment Assessment Project 2: a multinational survey to evaluate the proportion of patients achieving low-density lipoprotein cholesterol goals. Circulation. 120(1):28-34, 2009.
Libby P., The forgotten majority: unfinished business in cardiovascular risk reduction. Journal of the American College of Cardiology. 46(7):1225-1228, 2005.
Duff CJ., et al., Antibody-mediated disruption of the interaction between PCSK-9 and the low-density lipoprotein receptor. The Biochemical Journal. 419(3):577-584, 2009.
Lambert G., et al., Molecular basis of PCSK-9 function. Atherosclerosis. 203(1):1-7, 2009.
George M, et al., Looking into the crystal ball-upcoming drugs for dyslipidemia. Journal of Cardiovascular Pharmacology and Therapeutics. 20(1):11-20, 2016.
Zhang Y., et al., Dysregulation of the low-density lipoprotein receptor pathway is involved in lipid disorder-mediated organ injury. International Journal of Biological Sciences. 12(5):569-579, 2016.
Burke AC., et al.PCSK-9: regulation and target for drug development for dyslipidemia. Annual Review of Pharmacology and Toxicology. 13(3), 2016.
Abifadel M., et al., Mutations in PCSK-9 cause autosomal dominant hypercholesterolemia. Nature Genetics. 34(2):154-156, 2003.
Cohen JC., et al., Sequence variations in PCSK-9, low LDL, and protection against coronary heart disease. New England Journal of Medicine. 54(12):1264-1272, 2006.
Zhao Z., et al., Molecular characterization of loss of function mutations in PCSK-9 and identification of a compound heterozygote. American Journal of Human Genetics. 79(3):514-523, 2006.
Lagace TA., et al., Secreted PCSK-9 decreases the number of LDL receptors in hepatocytes and in livers of parabiotic mice. Journal of Clinical Investigation. 116(11):2995-3005, 2006.
Rashid S., et al., Decreased plasma cholesterol and hypersensitivity to statins in mice lacking PCSK-9. Proceedings of the National Academy of Sciences of the United States of America. 102(15):5374-5379, 2005.
Law et al: Quantifying effect of statins on low density lipoprotein cholesterol, ischaemic heart disease, and stroke: systematic review and meta-analysis, BMJ, 2003, 326:1423-1427.
Hudson et al.: Engineered Antibodies: Nat. Med., 9:129-134 (2003).
Hollinger et al: "Diabodies": Small bivalent and bispecific antibody fragments, Proc. Natl. Acad. Sci. (USA) 90: 6444-6448 (1993).
Clackson et al: Making antibody fragments using phage display libraries: Nature 352:624-628 (1991).
Shields et al: Lack of Fucose on Human IgG1 N-Linked Oligosaccharide Improves Binding to Human FcγRIII and Antibody-dependent Cellular Toxicity: J. Biol. Chem. (2002) 277:26733.
Almagro JC et al: Humanization of Antibodies: Frontiers inBioscience, (2008) 13:1619-1633.
Lonberg, Fully Human Antibodies from transgenic mouse and phage display platforms: Curr. Opin. Immunol. 20: 450-459 (2008).
McCafferty et al.: Phage antibodies: filamentous phage displaying antibody variable domains: Nature, 1990, 348: 552-554.
Marks et al: By-passing Immunization Human Antibodies from V-gene Libraries Displayed on Phage: J. Mol. Biol. 222: 581-597(1992).
Sidhu et al: Phage-displayed Antibody Libraries of Synthetic Heavy Chain Complementarity Determining Regions, J. Mol. Biol. 338(2): 299-310 (2004).

(56) References Cited

OTHER PUBLICATIONS

Lee et al: High-affinity Human Antibodies from Phage-displayed Synthetic Fab Libraries with a Single Framework Scaffold, J. Mol. Biol. 340(5): 1073-1093 (2004).
Fellouse: Synthetic antibodies from a four-amino-acid code: A dominant role for tyrosine in antigen recognition, Proc. Natl. Acad. Sci. USA, 101(34): 12467-12472 (2004).
Lee et al: Bivalent antibody phage display mimics natural immunoglobulin, J. Immunol. Methods, 284(1-2): 119-132 (2004).
Graham et al: Characteristics of a Human Cell Line Transformed by DNA from Human Adenovirus Type 5, J. Gen. Virol. 36: 59 (1977).
Urlaub et al: Isolation of Chinese hamster cell mutants deficient in dihydrofolate reductase activity, Proc. Natl. Acad. Sci. USA, 77: 216 (1980).
Estep, P et al: High throughput solution Based measurement of antibody-antigen affinity and epitope binning. MAbs, 2013, 5(2): 270-8.
Xu et al., Addressing polyspecificity of antibodies selected froman in vitro yeast presentation system: a FACS-based, high-throughput selection and analytical tool, Protein Engineering, Design & Selection, vol. 26 No. 10, pp. 663-670, 2013.
International search report and Written Opinion of corresponding International Application PCT/CN2017/118050, dated Mar. 27, 2018, with English translation.
U.S. Appl. No. 17/642,978, filed Mar. 15, 2022.
International Search Report and Written Opinion of PCT/CN2020/116245, dated Dec. 16, 2020.

\* cited by examiner

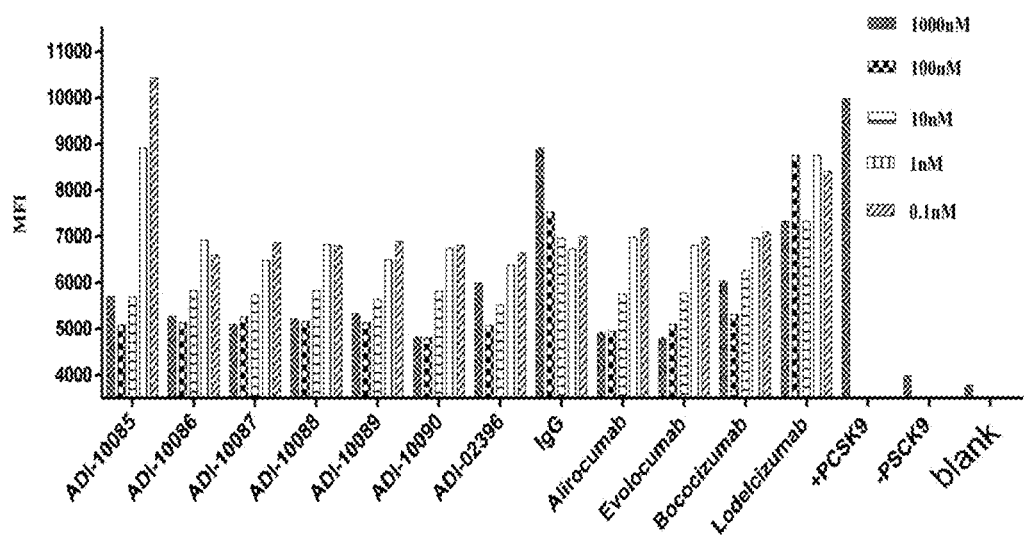
Fig. 1 Anti-PCSK9 antibodies block the binding of PCSK-9 to LDLR

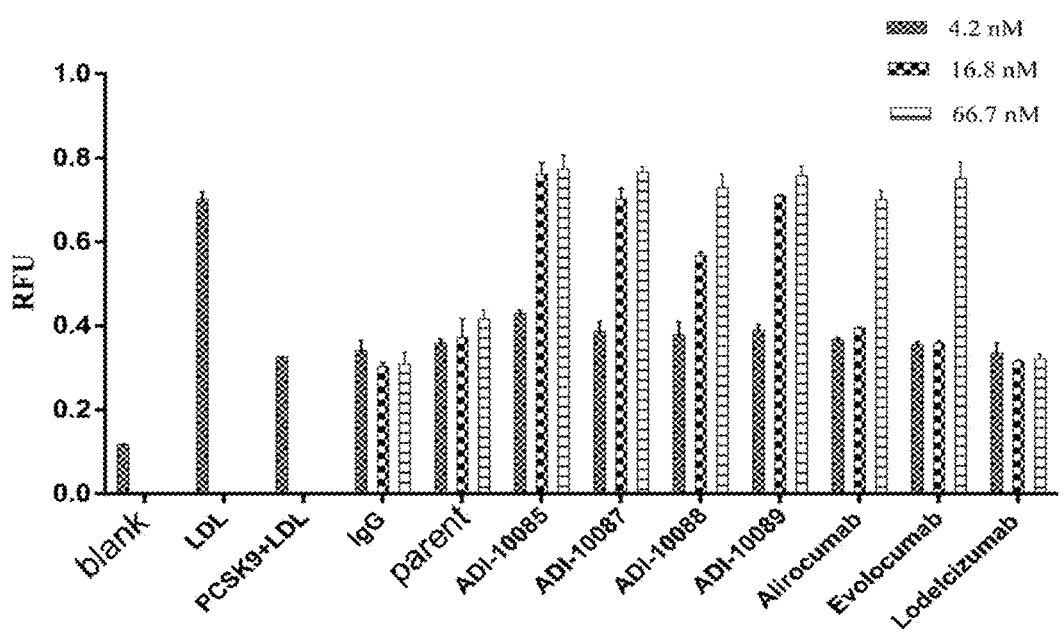
Fig. 2 Anti-PCSK9 antibodies increase the capability of HepG2 cells to restore LDLR.

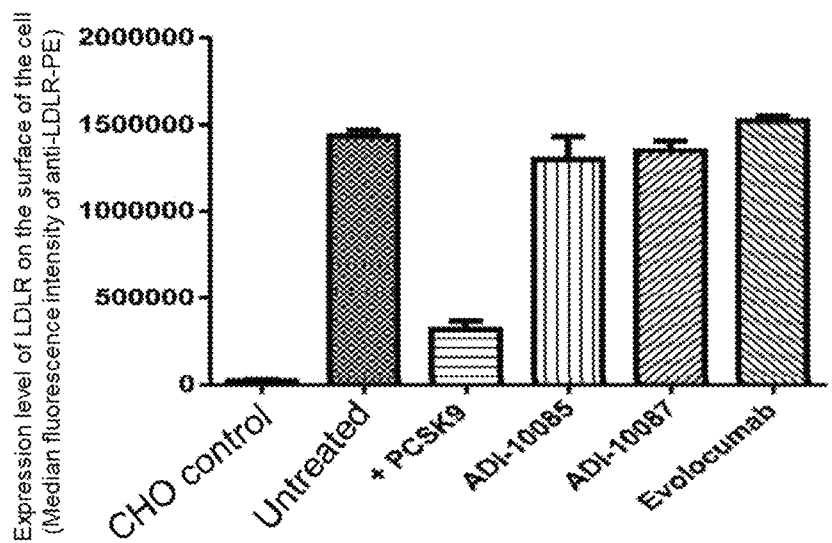
Fig. 3 Anti-PCSK9 antibodies reduce the cellular internalization of LDLR.

| IgG ADI name | VH germline | VH FR1 | VH CDR1 | VH FR2 | VH CDR2 | VH FR3 | VH CDR3 | VH FR4 |
|---|---|---|---|---|---|---|---|---|
| ADI-02396 | VH 4-3 9 | QLQLQESGPGLVKPSET LSLTCTVSG (SEQ ID NO:45) | GSISSSSYYW G (SEQ ID NO:1) | WIRQPPGKGLE WIG (SEQ ID NO:46) | SIYYSGSTYYNP SLKS (SEQ ID NO:2) | RVTISVDTSKNQFSLKLS SVTAADTAVYYC (SEQ ID NO:47) | AREGSGVVPAAGP NWFDP (SEQ ID NO:3) | WGQGTLVTVS S (SEQ ID NO:48) |
| ADI-09111 | VH 4-3 9 | QLQLQESGPGLVKPSET LSLTCTVSG (SEQ ID NO:45) | GSISSSSYYW G (SEQ ID NO:1) | WIRQPPGKGLE WIG (SEQ ID NO:46) | SIYYSGSTYYNP SLKS (SEQ ID NO:2) | RVTISVDTSKNQFSLKLS SVTAADTAVYYC (SEQ ID NO:47) | ARENSGVVPAAGP NWFDP (SEQ ID NO:18) | WGQGTLVTVS S (SEQ ID NO:48) |
| ADI-09112 | VH 4-3 9 | QLQLQESGPGLVKPSET LSLTCTVSG (SEQ ID NO:45) | GSISSSSYYW G (SEQ ID NO:1) | WIRQPPGKGLE WIG (SEQ ID NO:46) | SIYYSGSTYYNP FLKS (SEQ ID NO:14) | RVTISVDTSKNQFSLKLS SVTAADTAVYYC (SEQ ID NO:47) | ARENSGVVPAAGP NWFGP (SEQ ID NO:19) | WGQGTLVTVS S (SEQ ID NO:48) |
| ADI-09113 | VH 4-3 9 | QLQLQESGPGLVKPSET LSLTCTVSG (SEQ ID NO:45) | GSVSSSSYYW G (SEQ ID NO:7) | WIRQPPGKGLE WIG (SEQ ID NO:46) | SAYYSGSTYYNP SLKS (SEQ ID NO:15) | RVTISVDTSKNQFSLKLS SVTAADTAVYYC (SEQ ID NO:47) | ARENSGVVPAAGP NWFDP (SEQ ID NO:18) | WGQGTLVTVS S (SEQ ID NO:48) |
| ADI-10085 | VH 4-3 9 | QLQLQESGPGLVKPSET LSLTCTVSG (SEQ ID NO:45) | GSIVSSSYYW A (SEQ ID NO:8) | WIRQPPGKGLE WIG (SEQ ID NO:46) | SINYKGSTYYNP SLKS (SEQ ID NO:16) | RVTISVDTSKNQFSLKLS SVTAADTAVYYC (SEQ ID NO:47) | ARENSGVVPAAGP NWFGP (SEQ ID NO:19) | WGQGTLVTVS S (SEQ ID NO:48) |
| ADI-10086 | VH 4-3 9 | QLQLQESGPGLVKPSET LSLTCTVSG (SEQ ID NO:45) | GSIRSSAYYW G (SEQ ID NO:9) | WIRQPPGKGLE WIG (SEQ ID NO:46) | SINYRGSTYYNP SLKS (SEQ ID NO:17) | RVTISVDTSKNQFSLKLS SVTAADTAVYYC (SEQ ID NO:47) | ARENSGVVPAAGP NWFGP (SEQ ID NO:19) | WGQGTLVTVS S (SEQ ID NO:48) |

Fig. 4A

| IgG ADI name | VH germ line | VH FR1 | VH CDR1 | VH FR2 | VH CDR2 | VH FR3 | VH CDR3 | VH FR4 |
|---|---|---|---|---|---|---|---|---|
| ADI-10087 | VH4-39 | QLQLQESGPGLVKPSETLSLTC TVSG (SEQ ID NO:45) | GSISSASYYWS (SEQ ID NO:10) | WIRQPPGKGLEWIG (SEQ ID NO:46) | SINYRGSTYYNPSLKS (SEQ ID NO:17) | RVTISVDTSKNQFSLKLNSVTAAD TAVYYC (SEQ ID NO:47) | ARENSGVVPAAGPNWFGP (SEQ ID NO:19) | WGQGTLVTVSS (SEQ ID NO:48) |
| ADI-10088 | VH4-39 | QLQLQESGPGLVKPSETLSLTC TVSG (SEQ ID NO:45) | GSIGSSSYWA (SEQ ID NO:11) | WIRQPPGKGLEWIG (SEQ ID NO:46) | SINYRGSTYYNPSLKS (SEQ ID NO:17) | RVTISVDTSKNQFSLKLSSVTAAD TAVYYC (SEQ ID NO:47) | ARENSGVVPAAGPNWFDP (SEQ ID NO:18) | WGQGTLVTVSS (SEQ ID NO:48) |
| ADI-10089 | VH4-39 | QLQLQESGPGLVKPSETLSLTC TVSG (SEQ ID NO:45) | GSIGSSYYWT (SEQ ID NO:12) | WIRQPPGKGLEWIG (SEQ ID NO:46) | SINYRGSTYYNPSLKS (SEQ ID NO:17) | RVTISVDTSKNQFSLKLSSVTAAD TAVYYC (SEQ ID NO:47) | ARENSGVVPAAGPNWFDP (SEQ ID NO:18) | WGQGTLVTVSS (SEQ ID NO:48) |
| ADI-10090 | VH4-39 | QLQLQESGPGLVKPSETLSLTC TVSG (SEQ ID NO:45) | GSIWSSSYYWT (SEQ ID NO:13) | WIRQPPGKGLEWIG (SEQ ID NO:46) | SINYRGSTYYNPSLKS (SEQ ID NO:17) | RVTISVDTSKNQFSLKLSSVTAAD TAVYYC (SEQ ID NO:47) | ARENSGVVPAAGPNWFDP (SEQ ID NO:18) | WGQGTLVTVSS (SEQ ID NO:48) |
| consensus sequence | | | GSX1X2SX3X4YY WX5 (wherein X1 is selected from V and L, X2 is selected from the group consisting of S, V, P, G and W; X3 is selected from S or A; X4 is selected from S or A; X5 is selected from G, A, S or T) (SEQ ID NO:20) | | SX1X2YX3GSTYYNP X4LKS (Wherein X1 is selected from I or A; X2 is selected from the group consisting of Y and N; X3 is selected from the group consisting of S, K and R; and X4 is selected from the group consisting of S and F) (SEQ ID NO:21) | | AREX1SGVVPAAGPNW FX2P (Wherein said X1 is selected from the group consisting of G and N, and said X2 is selected from the group consisting of D and G) (SEQ ID NO:22) | |

Fig. 4A(continue)

| IgG ADI name | VL germ line | VL FR1 | VL CDR1 | VL FR2 | VL CDR2 | VL FR3 | VL CDR3 | VL FR4 |
|---|---|---|---|---|---|---|---|---|
| ADI-0 2396 | VK3-11 | EIVLTQSPATLSLSPG ERATLSC(SEQ ID NO:49) | RASQSVSS YLA(SEQ ID NO:4) | WYQQKPGQAPR LLIY(SEQ ID NO:50) | DASNRA T(SEQ ID NO:5) | GIPARFSGSGSGTDFTLTISS LEPEDFAVYYC(SEQ ID NO:51) | QQRRNWF T(SEQ ID NO:6) | FGGGTKVE IK(SEQ ID NO:52) |
| ADI-0 9111 | VK3-11 | EIVLTQSPATLSLSPG ERATLSC(SEQ ID NO:49) | RASQSVSS YLA(SEQ ID NO:4) | WYQQKPGQAPR LLIY(SEQ ID NO:50) | DASNRA T(SEQ ID NO:5) | GIPARFSGSGSGTDFTLTISS LEPEDFAVYYC(SEQ ID NO:51) | QQRRNWF T(SEQ ID NO:6) | FGGGTKVE IK(SEQ ID NO:52) |
| ADI-0 9112 | VK3-11 | EIVLTQSPATLSLSPG ERATLSC(SEQ ID NO:49) | RASQSVSS YLA(SEQ ID NO:4) | WYQQKPGQAPR LLIY(SEQ ID NO:50) | DASNRA T(SEQ ID NO:5) | GIPARFSGSGSGTDFTLTISS LEPEDFAVYYC(SEQ ID NO:51) | QQRRNWF T(SEQ ID NO:6) | FGGGTKVE IK(SEQ ID NO:52) |
| ADI-0 9113 | VK3-11 | EIVLTQSPATLSLSPG ERATLSC(SEQ ID NO:49) | RASQSVSS YLA(SEQ ID NO:4) | WYQQKPGQAPR LLIY(SEQ ID NO:50) | DASNRA T(SEQ ID NO:5) | GIPARFSGSGSGTDFTLTISS LEPEDFAVYYC(SEQ ID NO:51) | QQRRNWF T(SEQ ID NO:6) | FGGGTKVE IK(SEQ ID NO:52) |
| ADI-1 0085 | VK3-11 | EIVLTQSPATLSLSPG ERATLSC(SEQ ID NO:49) | RASQSVSS YLA(SEQ ID NO:4) | WYQQKPGQAPR LLIY(SEQ ID NO:50) | DASNRA T(SEQ ID NO:5) | GIPARFSGSGSGTDFTLTISS LEPEDFAVYYC(SEQ ID NO:51) | QQRRNWF T(SEQ ID NO:6) | FGGGTKVE IK(SEQ ID NO:52) |

Fig. 4B

| IgG ADI name | VL germline | VL FR1 | VL CDR1 | VL FR2 | VL CDR2 | VL FR3 | VL CDR3 | VL FR4 |
|---|---|---|---|---|---|---|---|---|
| ADI-1 0086 | VK3-11 | EIVLTQSPATLSLSPG ERATLSC(SEQ ID NO:49) | RASQSVSS YLA(SEQ ID NO:4) | WYQQKPGQAPR LLIY(SEQ ID NO:50) | DASNRA T(SEQ ID NO:5) | GIPARFSGSGSGTDFTLTISS LEPEDFAVYYC(SEQ ID NO:51) | QQRRNWF T(SEQ ID NO:6) | FGGGTKVE IK(SEQ ID NO:52) |
| ADI-1 0087 | VK3-11 | EIVLTQSPATLSLSPG ERATLSC(SEQ ID NO:49) | RASQSVSS YLA(SEQ ID NO:4) | WYQQKPGQAPR LLIY(SEQ ID NO:50) | DASNRA T(SEQ ID NO:5) | GIPARFSGSGSGTDFTLTISS LEPEDFAVYYC(SEQ ID NO:51) | QQRRNWF T(SEQ ID NO:6) | FGGGTKVE IK(SEQ ID NO:52) |
| ADI-1 0088 | VK3-11 | EIVLTQSPATLSLSPG ERATLSC(SEQ ID NO:49) | RASQSVSS YLA(SEQ ID NO:4) | WYQQKPGQAPR LLIY(SEQ ID NO:50) | DASNRA T(SEQ ID NO:5) | GIPARFSGSGSGTDFTLTISS LEPEDFAVYYC(SEQ ID NO:51) | QQRRNWF T(SEQ ID NO:6) | FGGGTKVE IK(SEQ ID NO:52) |
| ADI-1 0089 | VK3-11 | EIVLTQSPATLSLSPG ERATLSC(SEQ ID NO:49) | RASQSVSS YLA(SEQ ID NO:4) | WYQQKPGQAPR LLIY(SEQ ID NO:50) | DASNRA T(SEQ ID NO:5) | GIPARFSGSGSGTDFTLTISS LEPEDFAVYYC(SEQ ID NO:51) | QQRRNWF T(SEQ ID NO:6) | FGGGTKVE IK(SEQ ID NO:52) |
| ADI-1 0090 | VK3-11 | EIVLTQSPATLSLSPG ERATLSC(SEQ ID NO:49) | RASQSVSS YLA(SEQ ID NO:4) | WYQQKPGQAPR LLIY(SEQ ID NO:50) | DASNRA T(SEQ ID NO:5) | GIPARFSGSGSGTDFTLTISS LEPEDFAVYYC(SEQ ID NO:51) | QQRRNWF T(SEQ ID NO:6) | FGGGTKVE IK(SEQ ID NO:52) |

Fig. 4B (continue)

ADI-02396 (SEQ ID NO:23)
QLQLQESGPGLVKPSETLSLTCTVSGGSISSSSSYYWGWIRQPPGKGLEWIGSIYYSGSTYYNPSLKSRVTISVDTSKNQFSLKLSSVTAADTAVYYCAREGSGVVPAAGPNWFDPWGQGTLVTVSS

ADI-09111 (SEQ ID NO:25)
QLQLQESGPGLVKPSETLSLTCTVSGGSISSSSSYYWGWIRQPPGKGLEWIGSIYYSGSTYYNPSLKSRVTISVDTSKNQFSLKLSSVTAADTAVYYCARENSGVVPAAGPNWFDPWGQGTLVTVSS

ADI-09112 (SEQ ID NO:26)
QLQLQESGPGLVKPSETLSLTCTVSGGSISSSSSYYWGWIRQPPGKGLEWIGSIYYSGSTYYNPFLKSRVTISVDTSKNQFSLKLSSVTAADTAVYYCARENSGVVPAAGPNWFGPWGQGTLVTVSS

ADI-09113 (SEQ ID NO:27)
QLQLQESGPGLVKPSETLSLTCTVSGGSVSSSSYYWGWIRQPPGKGLEWIGSAYYSGSTYYNPSLKSRVTISVDTSKNQFSLKLSSVTAADTAVYYCARENSGVVPAAGPNWFDPWGQGTLVTVSS

ADI-10085 (SEQ ID NO:28)
QLQLQESGPGLVKPSETLSLTCTVSGGSIVSSSYYWAWIRQPPGKGLEWIGSINYKGSTYYNPSLKSRVTISVDTSKNQFSLKLSSVTAADTAVYYCARENSGVVPAAGPNWFGPWGQGTLVTVSS

ADI-10086 (SEQ ID NO:29)
QLQLQESGPGLVKPSETLSLTCTVSGGSIRSSAYYWGWIRQPPGKGLEWIGSINYRGSTYYNPSLKSRVTISVDTSKNQFSLKLSSVTAADTAVYYCARENSGVVPAAGPNWFGPWGQGTLVTVSS

ADI-10087 (SEQ ID NO:30)
QLQLQESGPGLVKPSETLSLTCTVSGGSISSASYYWSWIRQPPGKGLEWIGSINYRGSTYYNPSLKSRVTISVDTSKNQFSLKLSSVTAADTAVYYCARENSGVVPAAGPNWFGPWGQGTLVTVSS

ADI-10088 (SEQ ID NO:31)
QLQLQESGPGLVKPSETLSLTCTVSGGSISSSSYYWAWIRQPPGKGLEWIGSINYRGSTYYNPSLKSRVTISVDTSKNQFSLKLSSVTAADTAVYYCARENSGVVPAAGPNWFDPWGQGTLVTVSS

ADI-10089 (SEQ ID NO:32)
QLQLQESGPGLVKPSETLSLTCTVSGGSIGSSSYYWTWIRQPPGKGLEWIGSINYRGSTYYNPSLKSRVTISVDTSKNQFSLKLSSVTAADTAVYYCARENSGVVPAAGPNWFDPWGQGTLVTVSS

ADI-10090 (SEQ ID NO:33)
QLQLQESGPGLVKPSETLSLTCTVSGGSIWSSSYYWTWIRQPPGKGLEWIGSINYRGSTYYNPSLKSRVTISVDTSKNQFSLKLSSVTAADTAVYYCARENSGVVPAAGPNWFDPWGQGTLVTVSS

Fig. 5A The sequence of heavy chain variable region of the Antibody

SEQ ID NO:24
EIVLTQSPATLSLSPGERATLSCRASQSVSSYLAWYQQKPGQAPRLLIYDASNRATGIPARFSGSGSGTDFTLTISSLEPEDFAVYYCQQRRNWFTFGGGTKVEIK

Fig. 5B The sequence of light chain variable region of the Antibody

ANTI-PCSK9 ANTIBODY AND USE THEREOF

CROSS-REFERENCE TO RELATED APPLICATIONS

The present application is a U.S. National Stage entry under 35 U.S.C. § 371 of International Application No. PCT/CN2017/118050 filed on Dec. 22, 2017, designating the United States of America and published in Chinese on Jun. 28, 2018, which claims priority to Chinese application number 201611210645.3, filed on Dec. 24, 2016, each of which is hereby incorporated by reference in its entirety.

The present invention relates to a novel antibody and antibody fragments which specifically binds to Proprotein Convertase Subtilisin/Kexin Type 9 (PCSK9) (hereinafter referred to as PCSK9) and a composition comprising the antibody or antibody fragments. Furthermore, the invention relates to a nucleic acid encoding the antibody or antibody fragments thereof, and a host cell comprising the same, and related uses. Furthermore, the invention relates to the therapeutic and diagnostic use of these antibodies and antibody fragments.

INCORPORATION-BY-REFERENCE OF SEQUENCE LISTING

A sequence listing, filed as the ASCII text file "11275-008631-US0_ST25" which was created on Mar. 14, 2022 and is 80,871 bytes in size, is incorporated herein by reference in its entirety.

BACKGROUND OF THE INVENTION

Elevated serum cholesterol level is an important risk factor leading to cardiovascular events. Currently, the basis for cholesterol-lowering therapy is statin, which play an important role in primary and secondary prevention of atherosclerotic cardiovascular diseases. However, current lipid-lowering therapies do not meet clinical needs.

Although statins can reduce the death resulted from cardiovascular diseases, there are certain limitations in statins therapy. First, statins can reduce the level of Low Density Lipoprotein Cholesterol (LDL-C) by 40 to 55% at most, and doubling the dose of statins can only further reduce the level of LDL-C by about 6%.

Studies with large numbers of samples have shown that statins/combinations do not achieve the purpose for the treatment of LDL-C. In the study of L-TAP 2 (Lipid Treatment Assessment Project 2), 9955 patients with hyperlipidemia from nine countries in Americas, Europe, and Asia received stable lipid-lowering therapy (75% of them received statins therapy). The overall rate to reduce to normal by LDL-C is 47-84% (Waters D D et al, Lipid Treatment Assessment Project (L-TAP) 2: a multinational survey to evaluate the proportion of patients achieving Low Density Lipoprotein cholesterol goals. Circulation. 120(1): 28-34, 2009). In a comprehensive clinical analysis of multiple statins, statins have a role in reducing cardiovascular events as primary and secondary prevention, but totally only one-third of the events were reduced, especially in high-risk groups, among which only 27% of the events were reduced (Libby P., The forgotten majority: unfinished business in cardiovascular risk reduction. Journal of the American College of Cardiology. 46(7):1225-1228, 2005).

At present, various cholesterol-lowering drugs through different mechanisms are commercially available or under investigation, among which antibodies against PCSK9 have been extensively concerned due to their good safety and efficacy.

PCSK9 is a serine protease belonging to the family of proprotein convertase. In rodent and human, PCSK9 is mainly expressed in liver, secondly in small intestine and kidney. Firstly, a 72 kDa PCSK9 precursor protein is synthesized in the rough endoplasmic reticulum. The precursor protein comprises a 30 amino acid N-terminal signal peptide, a leader peptide (31-152), a catalytic region (153-425), and a C-terminal cysteine/histidine-rich domain (CHRD) (426-692) (Duff C J., et al., Antibody-mediated disruption of the interaction between PCSK-9 and the Low Density Lipoprotein receptor. The Biochemical Journal. 419(3):577-584, 2009; Lambert G., et al., Molecular basis of PCSK-9 function. Atherosclerosis. 203(1):1-7, 2009). After being autocatalyzed on position Gln152, the precursor protein is cleaved into a 14 kDa leader peptide fragment and a 63 kDa mature functional protein (including a catalytic structure and C-terminal domain), which are non-covalently tightly bound to form a complex. The leader peptide acts as a molecular chaperone of the mature protein, after which the complex leaves the endoplasmic reticulum to reach the Golgi apparatus, where it is secreted from the cells into the blood circulation via tyrosine sulfation, acetylation and a series of post-translational modifications in the Golgi apparatus.

The secretory PCSK9 mainly mediates the degradation of low density lipoprotein receptor (LDLR) on the surface of the plasma membrane of hepatocytes. The catalytic region of PCSK9 comprises a LDLR-binding site, capable of binding to Epidermal Growth Factor-Like Repeat Homology Domain-A (EGF-A) in LDLR structure and forming a LDLR/PCSK9 complex, which is then endocytosed into hepatocytes after coated with clathrin. In the endosomes of hepatocytes, the interaction between LDLR and PCSK9 is enhanced so as to form a more stable complex due to the acidic environment, i.e., due to the decreased pH value, which thereby inhibits the conformational change of LDLR, prevents the dissociation and recycling of LDLR and promotes the transportation of LDLR/PCSK9 complex into lysosomes to be degraded via proteolysis (Lambert G., et al., Molecular basis of PCSK9 function. Atherosclerosis. 203 (1):1-7, 2009; George M, et al., Looking into the crystal ball-upcoming drugs for dyslipidemia. Journal of Cardiovascular Pharmacology and Therapeutics. 20(1):11-20, 2016). PCSK9 acts in vivo by interfering with the clearance pathway of Low Density Lipoprotein Cholesterol (LDL-C). After LDL-C binds to LDLR and then be endocytosed, the bound PCSK9 prevents LDLR from detaching from the LDLR/LDL-C complex and will transport the complex to the lysosome to be degraded, so that LDLR cannot be recycled to the surface of the hepatocyte, which thereby reduces the amount of LDLR on the surface of the hepatocyte (Lambert G., et al., Molecular basis of PCSK-9 function. Atherosclerosis. 203(1): 1-7, 2009). In addition, immature PCSK9 in the Golgi apparatus can also directly bind to intracellular LDLR and then enter into lysosome to be degraded, which prevents LDLR from being expressed on the surface of hepatocyte (Lambert G., et al., Molecular basis of PCSK-9 function. Atherosclerosis. 203 (1): 1-7, 2009; Zhang Y., et al., Dysregulation of the Low Density Lipoprotein receptor pathway is involved in lipid disorder-mediated organ injury. International Journal of Biological Sciences. 12(5): 569-579, 2016). Therefore, PCSK9 can directly act on LDLR through cell surface and intracellular pathways, reduce the expression of LDLR on the surface of hepatocyte, decrease the LDL-C reuptake by hepatocytes, and result in the decreased LDL-C clearance and the persistently increased LDL-C level in circulation. Inhibition of PCSK9 can block the binding of plasma PCSK9 to LDLR, thereby prevent endocytosis and degradation of LDLR, increase the level and quantity of LDLR expression on the cell surface, increase the LDL-C reuptake by LDLR, and ultimately reduce the LDL-C level in circulation, so as to achieve the direct effect of lowering blood fat.

PCSK9 promotes the degradation of other members of LDLR family, including Very Low Density Lipoprotein Receptor (VLDLR), Apolipoprotein E Receptor 2 (apoER2), and LDLR-related protein 1 (LDLR) (Lambert G., et al., Molecular basis of PCSK-9 function. Atherosclerosis. 203 (1): 1-7, 2009). Although PCSK9 also binds to the EGF-A domain of VLDLR and apoER2, the degradation pathways are different, and so far the physiological significance of such degradation has not been revealed (Burke A C., et al. PCSK-9: regulation and target for drug Development for dyslipidemia. Annual Review of Pharmacology and Toxicology. 13(3), 2016). In addition, recent studies have shown that scavenger receptor CD36 can also interact with PCSK9, in addition to maintain homeostasis of cholesterol in circulation, suggesting that PCSK9 may play a role in the metabolism of triglyceride (Burke A C., et al. PCSK-9: regulation and Target for drug development for dyslipidemia. Annual Review of Pharmacology and Toxicology. 13(3), 2016). In summary, PCSK9 is closely related with lipid cycle and metabolism in vivo.

Studies on human genetics provide strong evidence supporting the role of PCSK9 in regulating the level of LDL-C and the incidence of coronary heart disease. Studies on human have confirmed that gain-of-function mutations in the PCSK9 gene are associated with the elevated serum level of LDL-C and associated with the early coronary heart disease (Abifadel M., et al., Mutations in PCSK-9 cause autosomal dominant hypercholesterolemia. Nature Genetics. 34(2):154-156, 2003), whereas loss-of-function mutations are associated with the lower serum level of LDL-C (Cohen J C., et al, Sequence variations in PCSK-9, low LDL, and protection against coronary heart disease. New England Journal of Medicine 54(12): 1264-1272, 2006). In a 15-year prospective cohort study (ARIC study), persons carrying PCSK9 nonsense mutation displayed significantly reduced level of LDK-C and risk of coronary heart disease (Cohen J C., et al., Sequence variations in PCSK-9, low LDL, and protection against coronary heart disease. New England Journal of Medicine. 54(12): 1264-1272, 2006). The study included 3,363 black subjects, 2.6% of whom carried $PCSK9^{142X}$ or $PCSK9^{679X}$ nonsense mutation. The level of LDL-C was decreased by 28% and the risk of coronary heart disease was decreased by 88%, compared to the subjects carrying no mutation (Cohen J C., et al., Sequence variations in PCSK-9, low LDL, and protection against coronary heart disease. New England Journal of Medicine. 54(12): 1264-1272, 2006). The study included 9524 white subjects, 3.2% of whom carried $PCSK9^{46L}$ nonsense mutation. The level of LDL-C was decreased by 15% and the risk of coronary heart disease was decreased by 47% (Cohen J C., et al., Sequence variations in PCSK-9, low LDL, and protection against coronary heart disease. New England Journal of Medicine. 54(12): 1264-1272, 2006). In addition, in a woman carrying PCSK9 a complex heterozygous inactivating mutation, PCSK9 was undetectable in plasma, and the serum level of LDL-C were extremely low (14 mg/dl), but overall health condition was good and she was fertile (Zhao Z., et al., Molecular characterization of loss of function mutations in PCSK-9 and identification of a compound heterozygote. American Journal of Human Genetics. 79(3): 514-523, 2006.).

Animal experiments in vivo further revealed the mechanism underlying the action of PCSK9. The elevated serum level of PCSK9 in mice resulted in a decrease in LDLR protein in hepatocytes and an increase in serum level of total cholesterol (Lagace T A., et al, Secreted PCSK-9 decreases the number of LDL receptors in hepatocytes and in livers of parabiotic mice. Journal of Clinical Investigation 116(11): 2995-3005, 2006). In contrast, PCSK9 knockout mice showed an elevated level of LDLR protein in hepatocytes (whereas the level of LDLR messenger RNA was unchanged), and the corresponding serum level of total cholesterol was reduced by approximately 50%. (Rashid S., et al., Decreased plasma cholesterol and hypersensitivity to statin in mice lacking PCSK-9. Proceedings of the National Academy of Sciences of the United States of America. 102(15): 5374-5379, 2005).

Thus, there is substantial evidence indicating that PCSK9 plays a role in the regulation of Low Density Lipoprotein (LDL); The expression or up-regulation of PCSK9 is associated with the increased plasma level of LDL cholesterol; The inhibition or deficiency in PCSK9 expression is associated with the decreased plasma level of LDL cholesterol; And the decrease in the level of LDL cholesterol is associated with changes in PCSK9 sequence, which has been found to confer protection against coronary heart disease (Cohen, 2006 N. Engl. J. Med. 354: 1264-1272).

In clinical trials, it has been found that a decreased level of LDL cholesterol is directly related to the grade of coronary events (Law et al., 2003 BMJ 326: 1423-1427). In addition, it has been found that a modest lifetime reduction in plasma level of LDL cholesterol is associated with a substantial reduction in the incidence of coronary events (Cohen, 2006 N. Engl. J. Med. 354: 1264-1272). It is also the same in populations with a high prevalence of non-lipid-related cardiovascular risk factors. Therefore, the management and control of the LDL cholesterol level is of great benefit.

For this reason, identification of other molecules that can be used to modulate cholesterol level and block or inhibit or neutralize the activity of PCSK9 would have tremendous benefits. PCSK9 antibodies and their effects on lowering plasma level of LDL-C are known in the art. Such PCSK9 antibodies and uses thereof are disclosed, for example, in US2009/0246192, US2009/0142352, US2010/0166768 and WO 2010/029513.

So far, the known PCSK9 monoclonal antibody Alirocumab (a product from Sanofi/Regeneron, trade name PRALUENT®) and Evolocumab (a product from Amgen, trade name REPATHA®) have shown remarkable efficacy in various types of primary hypercholesterolemia, and were approved in 2015 by FDA of the United States for use in hypercholesterolemia badly controlled by statin and in familial hypercholesterolemia (including heterozygous and homozygous familial hypercholesteremia, referred to as HeFH and HoFH, respectively), and for use in patients with coronary atherosclerotic heart disease.

There is still a need for substitutive PCSK9 antibodies. Particularly, there is a need for a PCSK9 antibody having high affinity with PCSK9, derived from a reliable cell line, with good stability, and capable of reducing the level of LDL-C with high efficiency. Still more particularly, there is a need for a substitutive PCSK9 antibody that is capable of reducing the level of LDL-C with high efficiency and capable of providing sustained ongoing duration (e.g., sustained inhibition of the level of LDL-C). Such antibody will also preferably have good physicochemical properties favorable for development, preparation or formulation.

SUMMARY OF THE INVENTION

The invention is based in part on a variety of antibodies directed against PCSK9. PCSK9 presents as an important and advantageous therapeutic target. And the invention provides antibodies for the treatment and diagnosis of pathological conditions associated with the expression and/or activity of PCSK9. Accordingly, the invention provides an anti-PCSK9 antibody, and a composition, a kit, a method, and a use related with the anti-PCSK9 antibody.

In some embodiments, an anti-PCSK9 antibody or antibody fragments (preferably antigen-binding fragment) that binds to PCSK9 or fragments thereof (preferably a human PCSK9 protein) is provided.

In some embodiments, the anti-PCSK9 antibody or antigen-binding fragments thereof of the present invention comprises a heavy chain variable region (HCVR), wherein said HCVR comprises complementarity determining regions (CDRs) HCDR1, HCDR2 and HCDR3, wherein HCDR1 comprises or consists of amino acid sequence having at least 90%, 91%, 92%, 93%, 94%, 95%, 96%, 97%, 98% or 99% identity or 100% identity to the amino acid sequence selected from the group consisting of SEQ ID NOs: 1, 7, 8, 9, 10, 11, 12, 13 and 20, HCDR2 comprises or consists of amino acid sequence having at least 90%, 91%, 92%, 93%, 94%, 95%, 96%, 97%, 98% or 99% identity or 100% identity to the amino acid sequence selected from the group consisting of SEQ ID NOs:2, 14, 15, 16, 17 and 21, and HCDR3 comprises or consists of amino acid sequence having at least 90%, 91%, 92%, 93%, 94%, 95%, 96%, 97%, 98% or 99% identity or 100% identity to the amino acid sequence selected from the group consisting of SEQ ID NOs: 3, 18, 19 and 22.

In some embodiments, the anti-PCSK9 antibody or antigen-binding fragments thereof of the present invention comprises a light chain variable region (LCVR), wherein said LCVR comprises complementarity determining regions (CDRs) LCDR1, LCDR2 and LCDR3, wherein LCDR1 comprises or consists of amino acid sequence having at least 90%, 91%, 92%, 93%, 94%, 95%, 96%, 97%, 98% or 99% identity or 100% identity to the amino acid sequence of SEQ ID NO: 4, LCDR2 comprises or consists of amino acid sequence having at least 90%, 91%, 92%, 93%, 94%, 95%, 96%, 97%, 98% or 99% identity or 100% identity to the amino acid sequence of SEQ ID NO: 5, and LCDR3 comprises or consists of amino acid sequence having at least 90%, 91%, 92%, 93%, 94%, 95%, 96%, 97%, 98% or 99% identity or 100% identity to the amino acid sequence of SEQ ID NO: 6.

In some embodiments, the anti-PCSK9 antibody or antigen-binding fragments thereof of present invention comprises a heavy chain variable region (HCVR) and a light chain variable region (LCVR), wherein said HCVR comprises complementarity determining regions (CDRs) HCDR1, HCDR2 and HCDR3, and said LCVR comprises CDRs LCDR1, LCDR2 and LCDR3, wherein HCDR1 comprises or consists of amino acid sequence having at least 90%, 91%, 92%, 93%, 94%, 95%, 96%, 97%, 98% or 99% identity or 100% identity to the amino acid sequence selected from the group consisting of SEQ ID NOs: 1, 7, 8, 9, 10, 11, 12, 13 and 20, HCDR2 comprises or consists of amino acid sequence having at least 90%, 91%, 92%, 93%, 94%, 95%, 96%, 97%, 98% or 99% identity or 100% identity to the amino acid sequence selected from the group consisting of SEQ ID NOs:2, 14, 15, 16, 17 and 21, and HCDR3 comprises or consists of amino acid sequence having at least 90%, 91%, 92%, 93%, 94%, 95%, 96%, 97%, 98% or 99% identity or 100% identity to the amino acid sequence selected from the group consisting of SEQ ID NOs: 3, 18, 19 and 22; and wherein LCDR1 comprises or consists of amino acid sequence having at least 90%, 91%, 92%, 93%, 94%, 95%, 96%, 97%, 98% or 99% identity or 100% identity to the amino acid sequence of SEQ ID NO: 4, LCDR2 comprises or consists of amino acid sequence having at least 90%, 91%, 92%, 93%, 94%, 95%, 96%, 97%, 98% or 99% identity or 100% identity to the amino acid sequence of SEQ ID NO: 5, and LCDR3 comprises or consists of amino acid sequence having at least 90%, 91%, 92%, 93%, 94%, 95%, 96%, 97%, 98% or 99% identity or 100% identity to the amino acid sequence of SEQ ID NO: 6.

In some embodiments, the anti-PCSK9 antibody or antigen-binding fragments thereof of the present invention comprises a heavy chain variable region (HCVR), wherein said HCVR comprises complementarity determining regions (CDRs) HCDR1, HCDR2 and HCDR3, wherein HCDR1 comprises or consists of the amino acid sequence selected from the group consisting of SEQ ID NOs: 1, 7, 8, 9, 10, 11, 12, 13 and 20, HCDR2 comprises or consists of the amino acid sequence selected from the group consisting of SEQ ID NOs:2, 14, 15, 16, 17 and 21, and HCDR3 comprises or consists of the amino acid sequence selected from the group consisting of SEQ ID NOs: 3, 18, 19 and 22.

In some embodiments, the anti-PCSK9 antibody or antigen-binding fragments thereof of the present invention comprises a light chain variable region (LCVR), wherein said LCVR comprises complementarity determining regions (CDRs) LCDR1, LCDR2 and LCDR3, wherein LCDR1 comprises or consists of the amino acid sequence of SEQ ID NO: 4, LCDR2 comprises or consists of the amino acid sequence of SEQ ID NO: 5, and LCDR3 comprises or consists of the amino acid sequence of SEQ ID NO: 6.

In some embodiments, the anti-PCSK9 antibody or antigen-binding fragments thereof of the present invention comprises a heavy chain variable region (HCVR) and a light chain variable region (LCVR), wherein said HCVR comprises complementarity determining regions (CDRs) HCDR1, HCDR2 and HCDR3, and said LCVR comprises CDRs LCDR1, LCDR2 and LCDR3, wherein HCDR1 comprises or consists of the amino acid sequence selected from the group consisting of SEQ ID NOs: 1, 7, 8, 9, 10, 11, 12, 13 and 20, HCDR2 comprises or consists of the amino acid sequence selected from the group consisting of SEQ ID NOs:2, 14, 15, 16, 17 and 21, and HCDR3 comprises or consists of the amino acid sequence selected from the group consisting of SEQ ID NOs: 3, 18, 19 and 22; and wherein LCDR1 comprises or consists of the amino acid sequence of SEQ ID NO: 4, LCDR2 comprises or consists of the amino acid sequence of SEQ ID NO: 5, and LCDR3 comprises or consists of the amino acid sequence of SEQ ID NO: 6.

In a preferred embodiment, the anti-PCSK9 antibody or antigen-binding fragments thereof provided herein comprises a heavy chain variable region (HCVR) and a light chain variable region (LCVR), wherein said HCVR comprises complementarity determining regions (CDRs) HCDR1, HCDR2 and HCDR3, and said LCVR comprises CDRs LCDR1, LCDR2 and LCDR3, wherein HCDR1 comprises or consists of the amino acid sequence of SEQ ID NO: 20, HCDR2 comprises or consists of the amino acid sequence of SEQ ID NO:21, and HCDR3 comprises or consists of the amino acid sequence of SEQ ID NO:22; and wherein LCDR1 comprises or consists of the amino acid sequence of SEQ ID NO: 4, LCDR2 comprises or consists of the amino acid sequence of SEQ ID NO: 5, and LCDR3 comprises or consists of the amino acid sequence of SEQ ID NO: 6.

In a preferred embodiment, the anti-PCSK9 antibody or antigen-binding fragments thereof provided herein comprises a heavy chain variable region (HCVR) and a light chain variable region (LCVR), wherein said HCVR comprises complementarity determining regions (CDRs) HCDR1, HCDR2 and HCDR3, and said LCVR comprises CDRs LCDR1, LCDR2 and LCDR3, wherein HCDR1 comprises or consists of the amino acid sequence of SEQ ID NO: 1, HCDR2 comprises or consists of the amino acid sequence of SEQ ID NO:2, and HCDR3 comprises or consists of the amino acid sequence of SEQ ID NO:3; and LCDR1 comprises or consists of the amino acid sequence of SEQ ID NO: 4, LCDR2 comprises or consists of the amino acid sequence of SEQ ID NO: 5, and LCDR3 comprises or consists of the amino acid sequence of SEQ ID NO: 6.

In a preferred embodiment, the anti-PCSK9 antibody or antigen-binding fragments thereof provided herein comprises a heavy chain variable region (HCVR) and a light chain variable region (LCVR), wherein said HCVR comprises complementarity determining regions (CDRs) HCDR1, HCDR2 and HCDR3, and said LCVR comprises CDRs LCDR1, LCDR2 and LCDR3, wherein HCDR1 comprises or consists of the amino acid sequence of SEQ ID NO: 1, HCDR2 comprises or consists of the amino acid sequence of SEQ ID NO:2, and HCDR3 comprises or consists of the amino acid sequence of SEQ ID NO:18; and LCDR1 comprises or consists of the amino acid sequence of SEQ ID NO: 4, LCDR2 comprises or consists of the amino acid sequence of SEQ ID NO: 5, and LCDR3 comprises or consists of the amino acid sequence of SEQ ID NO: 6.

In a preferred embodiment, the anti-PCSK9 antibody or antigen-binding fragments thereof provided herein comprises a heavy chain variable region (HCVR) and a light chain variable region (LCVR), wherein said HCVR comprises complementarity determining regions (CDRs) HCDR1, HCDR2 and HCDR3, and said LCVR comprises CDRs LCDR1, LCDR2 and LCDR3, wherein HCDR1 comprises or consists of the amino acid sequence of SEQ ID NO: 1, HCDR2 comprises or consists of the amino acid sequence of SEQ ID NO:14, and HCDR3 comprises or consists of the amino acid sequence of SEQ ID NO:19; and LCDR1 comprises or consists of the amino acid sequence of SEQ ID NO: 4, LCDR2 comprises or consists of the amino acid sequence of SEQ ID NO: 5, and LCDR3 comprises or consists of the amino acid sequence of SEQ ID NO: 6.

In a preferred embodiment, the anti-PCSK9 antibody or antigen-binding fragments thereof provided herein comprises a heavy chain variable region (HCVR) and a light chain variable region (LCVR), wherein said HCVR comprises complementarity determining regions (CDRs) HCDR1, HCDR2 and HCDR3, and said LCVR comprises CDRs LCDR1, LCDR2 and LCDR3, wherein HCDR1 comprises or consists of the amino acid sequence of SEQ ID NO: 7, HCDR2 comprises or consists of the amino acid sequence of SEQ ID NO:15, and HCDR3 comprises or consists of the amino acid sequence of SEQ ID NO:18; and LCDR1 comprises or consists of the amino acid sequence of SEQ ID NO: 4, LCDR2 comprises or consists of the amino acid sequence of SEQ ID NO: 5, and LCDR3 comprises or consists of the amino acid sequence of SEQ ID NO: 6.

In a preferred embodiment, the anti-PCSK9 antibody or antigen-binding fragments thereof provided herein comprises a heavy chain variable region (HCVR) and a light chain variable region (LCVR), wherein said HCVR comprises complementarity determining regions (CDRs) HCDR1, HCDR2 and HCDR3, and said LCVR comprises CDRs LCDR1, LCDR2 and LCDR3, wherein HCDR1 comprises or consists of the amino acid sequence of SEQ ID NO: 8, HCDR2 comprises or consists of the amino acid sequence of SEQ ID NO:16, and HCDR3 comprises or consists of the amino acid sequence of SEQ ID NO:19; and LCDR1 comprises or consists of the amino acid sequence of SEQ ID NO: 4, LCDR2 comprises or consists of the amino acid sequence of SEQ ID NO: 5, and LCDR3 comprises or consists of the amino acid sequence of SEQ ID NO: 6.

In a preferred embodiment, the anti-PCSK9 antibody or antigen-binding fragments thereof provided herein comprises a heavy chain variable region (HCVR) and a light chain variable region (LCVR), wherein said HCVR comprises complementarity determining regions (CDRs) HCDR1, HCDR2 and HCDR3, and said LCVR comprises CDRs LCDR1, LCDR2 and LCDR3, wherein HCDR1 comprises or consists of the amino acid sequence of SEQ ID NO: 9, HCDR2 comprises or consists of the amino acid sequence of SEQ ID NO:17, and HCDR3 comprises or consists of the amino acid sequence of SEQ ID NO:19; and LCDR1 comprises or consists of the amino acid sequence of SEQ ID NO: 4, LCDR2 comprises or consists of the amino acid sequence of SEQ ID NO: 5, and LCDR3 comprises or consists of the amino acid sequence of SEQ ID NO: 6.

In a preferred embodiment, the anti-PCSK9 antibody or antigen-binding fragments thereof provided herein comprises a heavy chain variable region (HCVR) and a light chain variable region (LCVR), wherein said HCVR comprises complementarity determining regions (CDRs) HCDR1, HCDR2 and HCDR3, and said LCVR comprises CDRs LCDR1, LCDR2 and LCDR3, wherein HCDR1 comprises or consists of the amino acid sequence of SEQ ID NO: 10, HCDR2 comprises or consists of the amino acid sequence of SEQ ID NO:17, and HCDR3 comprises or consists of the amino acid sequence of SEQ ID NO:19; and LCDR1 comprises or consists of the amino acid sequence of SEQ ID NO: 4, LCDR2 comprises or consists of the amino acid sequence of SEQ ID NO: 5, and LCDR3 comprises or consists of the amino acid sequence of SEQ ID NO: 6.

In a preferred embodiment, the anti-PCSK9 antibody or antigen-binding fragments thereof provided herein comprises a heavy chain variable region (HCVR) and a light chain variable region (LCVR), wherein said HCVR comprises complementarity determining regions (CDRs) HCDR1, HCDR2 and HCDR3, and said LCVR comprises CDRs LCDR1, LCDR2 and LCDR3, wherein HCDR1 comprises or consists of the amino acid sequence of SEQ ID NO: 11, HCDR2 comprises or consists of the amino acid sequence of SEQ ID NO:17, and HCDR3 comprises or consists of the amino acid sequence of SEQ ID NO:18; and LCDR1 comprises or consists of the amino acid sequence of SEQ ID NO: 4, LCDR2 comprises or consists of the amino acid sequence of SEQ ID NO: 5, and LCDR3 comprises or consists of the amino acid sequence of SEQ ID NO: 6.

In a preferred embodiment, the anti-PCSK9 antibody or antigen-binding fragments thereof provided herein comprises a heavy chain variable region (HCVR) and a light chain variable region (LCVR), wherein said HCVR comprises complementarity determining regions (CDRs) HCDR1, HCDR2 and HCDR3, and said LCVR comprises CDRs LCDR1, LCDR2 and LCDR3, wherein HCDR1 comprises or consists of the amino acid sequence of SEQ ID NO: 12, HCDR2 comprises or consists of the amino acid sequence of SEQ ID NO:17, and HCDR3 comprises or consists of the amino acid sequence of SEQ ID NO:18; and LCDR1 comprises or consists of the amino acid sequence of SEQ ID NO: 4, LCDR2 comprises or consists of the amino acid sequence of SEQ ID NO: 5, and LCDR3 comprises or consists of the amino acid sequence of SEQ ID NO: 6.

In a preferred embodiment, the anti-PCSK9 antibody or antigen-binding fragments thereof provided herein comprises a heavy chain variable region (HCVR) and a light chain variable region (LCVR), wherein said HCVR comprises complementarity determining regions (CDRs) HCDR1, HCDR2 and HCDR3, and said LCVR comprises CDRs LCDR1, LCDR2 and LCDR3, wherein HCDR1 comprises or consists of the amino acid sequence of SEQ ID NO: 13, HCDR2 comprises or consists of the amino acid sequence of SEQ ID NO:17, and HCDR3 comprises or consists of the amino acid sequence of SEQ ID NO:18; and LCDR1 comprises or consists of the amino acid sequence of SEQ ID NO: 4, LCDR2 comprises or consists of the amino acid sequence of SEQ ID NO: 5, and LCDR3 comprises or consists of the amino acid sequence of SEQ ID NO: 6.

In some embodiments, the anti-PCSK9 antibody or antigen-binding fragments thereof of the present invention comprises a heavy chain variable region HCVR, which comprises or consists of amino acid sequence having at least 90%, 91%, 92%, 93%, 94%, 95%, 96%, 97%, 98% or 99% identity or 100% identity to the amino acid sequence selected from the group consisting of SEQ ID NOs: 23, 25, 26, 27, 28, 29, 30, 31, 32 and 33.

In some embodiments, the anti-PCSK9 antibody or antigen-binding fragments thereof of the present invention comprises a light chain variable region LCVR, which comprises or consists of amino acid sequence having at least 90%, 91%, 92%, 93%, 94%, 95%, 96%, 97%, 98% or 99% identity or 100% identity to the amino acid sequence of SEQ ID NO: 24.

In some embodiments, the anti-PCSK9 antibody or antigen-binding fragments thereof of the present invention comprises a heavy chain variable region (HCVR) and a light chain variable region (LCVR), wherein the heavy chain variable region HCVR comprises or consists of amino acid sequence having at least 90%, 91%, 92%, 93%, 94%, 95%, 96%, 97%, 98% or 99% identity or 100% identity to the amino acid sequence selected from the group consisting of SEQ ID NOs: 23, 25, 26, 27, 28, 29, 30, 31, 32 and 33; and wherein the light chain variable region LCVR comprises or consists of amino acid sequence having at least 90%, 91%, 92%, 93%, 94%, 95%, 96%, 97%, 98% or 99% identity or 100% identity to the amino acid sequence of SEQ ID NO: 24.

In some embodiments, the anti-PCSK9 antibody or antigen-binding fragments thereof of the present invention comprises a heavy chain variable region HCVR, which comprises or consists of the amino acid sequence selected from the group consisting of SEQ ID NOs: 23, 25, 26, 27, 28, 29, 30, 31, 32 and 33.

In some embodiments, the anti-PCSK9 antibody or antigen-binding fragments thereof of the present invention comprises a light chain variable region LCVR, which comprises or consists of the amino acid sequence of SEQ ID NO: 24.

In some embodiments, the anti-PCSK9 antibody or antigen-binding fragments thereof of the present invention comprises a heavy chain variable region (HCVR) and a light chain variable region (LCVR), wherein the heavy chain variable region HCVR comprises or consists of the amino acid sequence selected from the group consisting of SEQ ID NOs: 23, 25, 26, 27, 28, 29, 30, 31, 32 and 33; and wherein the light chain variable region LCVR comprises or consists of the amino acid sequence of SEQ ID NO: 24.

In a preferred embodiment, the anti-PCSK9 antibody or antigen-binding fragments thereof provided herein comprises a heavy chain variable region (HCVR) and a light chain variable region (LCVR), wherein the heavy chain variable region HCVR comprises or consists of the amino acid sequence of SEQ ID NO: 23; and wherein the light chain variable region LCVR comprises or consists of the amino acid sequence of SEQ ID NO: 24.

In a preferred embodiment, the anti-PCSK9 antibody or antigen-binding fragments thereof provided herein comprises a heavy chain variable region (HCVR) and a light chain variable region (LCVR), wherein the heavy chain variable region HCVR comprises or consists of the amino acid sequence of SEQ ID NO: 25; and the light chain variable region LCVR comprises or consists of the amino acid sequence of SEQ ID NO: 24.

In a preferred embodiment, the anti-PCSK9 antibody or antigen-binding fragments thereof provided herein comprises a heavy chain variable region (HCVR) and a light chain variable region (LCVR), wherein the heavy chain variable region HCVR comprises or consists of the amino acid sequence of SEQ ID NO: 26; and the light chain variable region LCVR comprises or consists of the amino acid sequence of SEQ ID NO: 24.

In a preferred embodiment, the anti-PCSK9 antibody or antigen-binding fragments thereof provided herein comprises a heavy chain variable region (HCVR) and a light chain variable region (LCVR), wherein the heavy chain variable region HCVR comprises or consists of the amino acid sequence of SEQ ID NO: 27; and the light chain variable region LCVR comprises or consists of the amino acid sequence of SEQ ID NO: 24.

In a preferred embodiment, the anti-PCSK9 antibody or antigen-binding fragments thereof provided herein comprises a heavy chain variable region (HCVR) and a light chain variable region (LCVR), wherein the heavy chain variable region HCVR comprises or consists of the amino acid sequence of SEQ ID NO: 28; and the light chain variable region LCVR comprises or consists of the amino acid sequence of SEQ ID NO: 24.

In a preferred embodiment, the anti-PCSK9 antibody or antigen-binding fragments thereof provided herein comprises a heavy chain variable region (HCVR) and a light chain variable region (LCVR), wherein the heavy chain variable region HCVR comprises or consists of the amino acid sequence of SEQ ID NO: 29; and the light chain variable region LCVR comprises or consists of the amino acid sequence of SEQ ID NO: 24.

In a preferred embodiment, the anti-PCSK9 antibody or antigen-binding fragments thereof provided herein comprises a heavy chain variable region (HCVR) and a light chain variable region (LCVR), wherein the heavy chain variable region HCVR comprises or consists of the amino acid sequence of SEQ ID NO: 30; and the light chain variable region LCVR comprises or consists of the amino acid sequence of SEQ ID NO: 24.

In a preferred embodiment, the anti-PCSK9 antibody or antigen-binding fragments thereof provided herein comprises a heavy chain variable region (HCVR) and a light chain variable region (LCVR), wherein the heavy chain variable region HCVR comprises or consists of the amino acid sequence of SEQ ID NO: 31; and the light chain variable region LCVR comprises or consists of the amino acid sequence of SEQ ID NO: 24.

In a preferred embodiment, the anti-PCSK9 antibody or antigen-binding fragments thereof provided herein comprises a heavy chain variable region (HCVR) and a light chain variable region (LCVR), wherein the heavy chain variable region HCVR comprises or consists of the amino acid sequence of SEQ ID NO: 32; and the light chain variable region LCVR comprises or consists of the amino acid sequence of SEQ ID NO: 24.

In a preferred embodiment, the anti-PCSK9 antibody or antigen-binding fragments thereof provided herein comprises a heavy chain variable region (HCVR) and a light chain variable region (LCVR), wherein the heavy chain variable region HCVR comprises or consists of the amino acid sequence of SEQ ID NO: 33; and the light chain variable region LCVR comprises or consists of the amino acid sequence of SEQ ID NO: 24.

In some embodiments, the anti-PCSK9 antibody or antigen-binding fragments thereof of the present invention comprises a heavy chain, wherein the heavy chain comprises or consists of amino acid sequence having at least 90%, 91%, 92%, 93%, 94%, 95%, 96%, 97%, 98% or 99% identity or 100% identity to the amino acid sequence selected from the group consisting of SEQ ID NOs: 34, 36, 37, 38, 39, 40, 41, 42, 43 and 44.

In some embodiments, the anti-PCSK9 antibody or antigen-binding fragments thereof of the present invention comprises a light chain, wherein the light chain comprises or consists of amino acid sequence having at least 90%, 91%, 92%, 93%, 94%, 95%, 96%, 97%, 98% or 99% identity or 100% identity to the amino acid sequence of SEQ ID NO:35.

In some embodiments, an anti-PCSK9 antibody or antigen-binding fragments thereof of the present invention comprises a heavy chain and a light chain, wherein the heavy chain comprises or consists of amino acid sequence having at least 90%, 91%, 92%, 93%, 94%, 95%, 96%, 97%, 98% or 99% identity or 100% identity to the amino acid sequence selected from the group consisting of SEQ ID NOs: 34, 36, 37, 38, 39, 40, 41, 42, 43 and 44; wherein the light chain comprises or consists of amino acid sequence having at least 90%, 91%, 92%, 93%, 94%, 95%, 96%, 97%, 98% or 99% identity or 100% identity to the amino acid sequence of SEQ ID NO:35.

In some embodiments, an anti-PCSK9 antibody or antigen-binding fragments thereof of the present invention comprises a heavy chain, wherein the heavy chain comprises or consists of the amino acid sequence selected from the group consisting of SEQ ID NOs: 34, 36, 37, 38, 39, 40, 41, 42, 43 and 44.

In some embodiments, an anti-PCSK9 antibody or antigen-binding fragments thereof of the present invention comprises a light chain, wherein the light chain comprises or consists of the amino acid sequence of SEQ ID NO:35.

In some embodiments, an anti-PCSK9 antibody or antigen-binding fragments thereof of the present invention comprises a heavy chain and a light chain, wherein the heavy chain comprises or consists of the amino acid sequence selected from the group consisting of SEQ ID NOs: 34, 36, 37, 38, 39, 40, 41, 42, 43 and 44; and the light chain comprises or consists of the amino acid sequence of SEQ ID NO:35.

In a preferred embodiment, an anti-PCSK9 antibody or antigen-binding fragments thereof provided herein comprises a heavy chain and a light chain, wherein the heavy chain comprises or consists of the amino acid sequence of SEQ ID NO: 34; and the light chain comprises or consists of the amino acid sequence of SEQ ID NO:35.

In a preferred embodiment, an anti-PCSK9 antibody or antigen-binding fragments thereof provided herein comprises a heavy chain and a light chain, wherein the heavy chain comprises or consists of the amino acid sequence of SEQ ID NO: 36; and the light chain comprises or consists of the amino acid sequence of SEQ ID NO:35.

In a preferred embodiment, an anti-PCSK9 antibody or antigen-binding fragments thereof provided herein comprises a heavy chain and a light chain, wherein the heavy chain comprises or consists of the amino acid sequence of SEQ ID NO: 37; and the light chain comprises or consists of the amino acid sequence of SEQ ID NO:35.

In a preferred embodiment, an anti-PCSK9 antibody or antigen-binding fragments thereof provided herein comprises a heavy chain and a light chain, wherein the heavy chain comprises or consists of the amino acid sequence of SEQ ID NO: 38; and the light chain comprises or consists of the amino acid sequence of SEQ ID NO:35.

In a preferred embodiment, an anti-PCSK9 antibody or antigen-binding fragments thereof provided herein comprises a heavy chain and a light chain, wherein the heavy chain comprises or consists of the amino acid sequence of SEQ ID NO: 39; and the light chain comprises or consists of the amino acid sequence of SEQ ID NO:35.

In a preferred embodiment, an anti-PCSK9 antibody or antigen-binding fragments thereof provided herein comprises a heavy chain and a light chain, wherein the heavy chain comprises or consists of the amino acid sequence of SEQ ID NO: 40; and the light chain comprises or consists of the amino acid sequence of SEQ ID NO:35.

In a preferred embodiment, an anti-PCSK9 antibody or antigen-binding fragments thereof provided herein comprises a heavy chain and a light chain, wherein the heavy chain comprises or consists of the amino acid sequence of SEQ ID NO: 41; and the light chain comprises or consists of the amino acid sequence of SEQ ID NO:35.

In a preferred embodiment, an anti-PCSK9 antibody or antigen-binding fragments thereof provided herein comprises a heavy chain and a light chain, wherein the heavy chain comprises or consists of the amino acid sequence of SEQ ID NO: 42; and the light chain comprises or consists of the amino acid sequence of SEQ ID NO:35.

In a preferred embodiment, an anti-PCSK9 antibody or antigen-binding fragments thereof provided herein comprises a heavy chain and a light chain, wherein the heavy chain comprises or consists of the amino acid sequence of SEQ ID NO: 43; and the light chain comprises or consists of the amino acid sequence of SEQ ID NO:35.

In a preferred embodiment, an anti-PCSK9 antibody or antigen-binding fragments thereof provided herein comprises a heavy chain and a light chain, wherein the heavy chain comprises or consists of the amino acid sequence of SEQ ID NO: 44; and the light chain comprises or consists of the amino acid sequence of SEQ ID NO:35.

In some embodiments, the antibody of the present invention also encompasses variants of the amino acid sequence of an anti-PCSK9 antibody, as well as antibodies that bind to the same epitope as any of the antibodies described above.

In certain embodiments, an antibody or antibody fragments (preferably antigen-binding fragments) thereof that bind to PCSK9 or fragments thereof is provided, wherein the antibody binds to an epitope within a fragment of PCSK9. In certain embodiments, an antibody or antibody fragments thereof that bind to PCSK9 or fragments thereof is provided, wherein the antibody binds to an epitope within the fragment of PCSK9, comprising amino acids 75 to 93 and 100 to 110 of human PCSK9 amino acid sequence SEQ ID NO: 53. In certain embodiments, the functional and/or structural epitope of the antibody according to the present invention comprises residue Y78 of human PCSK9. In certain embodiments, the functional and/or structural epitope of the antibody according to the present invention comprises residue T86 of human PCSK9. In certain embodiments, the functional and/or structural epitope of the antibody according to the present invention comprises residue H87 of human PCSK9. In certain embodiments, the functional and/or structural epitope of the antibody according to the present invention comprises residues Y78, T86 and H87 of human PCSK9. In certain embodiments, the functional and/or structural epitope of the antibody according to the present invention comprises residue R104 of human PCSK9. In certain embodiments, the functional and/or structural epitope of the antibody according to the present invention comprises residues Y78, T86, H87 and R104 of human PCSK9. In certain embodiments, the functional and/or structural epitope comprises one or more selected from residues Y78, T86, H87 and R104 of human PCSK9. In certain embodiments, the functional and/or structural epitope comprises one or more residues adjacent to Y78, T86, H87 and R104 of human PCSK9. In certain embodiments, the functional and/or structural epitope of the antibody according to the present invention comprises (i) at least one residue selected from the group consisting of Y78, T86 and H87 of human PCSK9, (ii) R104 of human PCSK9. In certain embodiments, the functional and/or structural epitope comprises one, two, three or all of the following residues: Y78, T86, H87 and R104 of human PCSK9.

In some embodiments, the anti-PCSK9 antibody is a monoclonal antibody. In some embodiments, the anti-PCSK9 antibody is humanized. In some embodiments, the anti-PCSK9 antibody is a human antibody. In some embodiments, at least a portion of the framework sequence of an anti-PCSK9 antibody is human consensus framework sequence. In one embodiment, an anti-PCSK9 antibody of the present invention further encompasses antibody fragments thereof, preferably antibody fragment selected from the group consisting of Fab, Fab'-SH, Fv, scFv or (Fab')$_2$ fragment.

In one aspect, the invention provides a nucleic acid encoding any of the above anti-PCSK9 antibodies or fragments thereof. In one embodiment, a vector comprising the nucleic acid is provided. In one embodiment, the vector is an expression vector. In one embodiment, a host cell comprising the vector is provided. In one embodiment, the host cell is eukaryotic. In another embodiment, the host cell is selected from the group consisting of yeast cell, mammalian cell, or other cells suitable for the preparation of the antibody or antigen-binding fragment thereof. In another embodiment, the host cell is prokaryotic.

In one embodiment, the invention provides a method of producing an anti-PCSK9 antibody or fragments thereof (preferably antigen-binding fragments), wherein the method comprises cultivating the host cell under conditions suitable for expressing the nucleic acid encoding the antibody or fragments thereof (preferably antigen-binding fragments), and optionally, isolating the antibody or fragments thereof (preferably antigen-binding fragments thereof). In a certain embodiment, the method further comprises recovering the anti-PCSK9 antibody or fragments thereof (preferably antigen-binding fragments thereof) from the host cell.

In some embodiments, the invention provides a composition comprising any of the anti-PCSK9 antibodies or fragments thereof (preferably antigen-binding fragments thereof) described herein, preferably the composition is a pharmaceutical composition. In one embodiment, the composition further comprises a pharmaceutically acceptable carrier.

In one aspect, the invention relates to a method of inhibiting the binding of PCSK9 to LDL-receptor (LDLR) in a subject, the method comprises administering an effective amount of any of the anti-PCSK9 antibodies or fragments thereof described herein to the subject. The invention further relates to the use of any of the anti-PCSK9 antibodies or fragments thereof described herein in the preparation of a composition or a medicament for inhibiting the binding of PCSK9 to LDL-receptor (LDLR) in a subject.

In another aspect, the invention relates to a method of lowering the level of cholesterol in a subject, the method comprises administering an effective amount of any of the anti-PCSK9 antibodies or fragments thereof described herein to the subject. In one embodiment, the cholesterol is LDL-cholesterol, preferably serum cholesterol. In another aspect, the invention relates to a method of lowering the level of LDL-cholesterol in a subject, the method comprises administering an effective amount of any of the anti-PCSK9 antibodies or fragments thereof described herein to the subject. In some embodiments, the invention relates to a method of lowering the serum level of LDL-cholesterol in a subject, the method comprises administering an effective amount of any of the anti-PCSK9 antibodies or fragments thereof described herein to the subject.

In another aspect, the invention further relates to the use of any of the anti-PCSK9 antibodies or fragments thereof described herein in the preparation of a medicament for lowering the level of cholesterol (in one embodiment, the level of LDL-cholesterol or the serum level of LDL-cholesterol) in a subject.

In another aspect, the invention relates to a method of treating a condition associated with the elevated level of LDL-cholesterol in a subject, the method comprises administering an effective amount of any of the anti-PCSK9 antibodies or fragments thereof described herein to the subject. The present invention further relates to the use of any of the anti-PCSK9 antibodies or fragments thereof described herein in the preparation of a medicament for treating a subject's condition associated with the elevated level of the LDL-cholesterol in a subject.

In one aspect, the present invention relates to a method of treating cholesterol-related diseases, the method comprises administering an effective amount of any of the anti-PCSK9 antibodies or fragments thereof described herein to the subject. The present invention further relates to the use of any of the anti-PCSK9 antibodies or fragments thereof described herein in the preparation of a medicament for treating cholesterol-related diseases. Exemplary and non-limiting examples of the cholesterol-related disease are provided below. In some embodiments, the cholesterol-related disease is hypercholesterolemia or hyperlipidemia. In some embodiments, the present invention relates to a method of treating hypercholesterolemia and/or hyperlipidemia, the method comprises administering an effective amount of any of the anti-PCSK9 antibodies or fragments thereof described herein to the subject. In some embodiments, the invention further relates to the use of any of the anti-PCSK9 antibodies or fragments thereof described herein in the preparation of a medicament for treating hypercholesterolemia and/or hyperlipidemia.

In one aspect, the present invention relates to a method of treating any disease or condition which may be ameliorated, slowed, inhibited or prevented by eliminating, inhibiting or reducing the activity of PCSK9. In some embodiments, diseases or conditions which can be treated or prevented by statins can also be treated with any of the anti-PCSK9 antibodies or fragments thereof described herein. In some embodiments, diseases or conditions which can be benefited from the prevented cholesterol synthesis or the increased LDLR expression can also be treated with any of the anti-PCSK9 antibodies or fragments thereof described herein.

In some embodiments, the methods described herein further comprise administration in combination with an effective amount of a second medicament to the subject, wherein an anti-PCSK9 antibody or fragments thereof described herein is a first drug. In one embodiment, the second medicament increases the level of LDLR protein. In another embodiment, the second medicament lowers the level of LDL-cholesterol. In another embodiment, the second medicament comprises statins. In another embodiment, the second medicament is statins. In some embodiments, the statins are selected from the group consisting of atorvastatin, fluvastatin, lovastatin, mevastatin, pitavastatin, pravastatin, rosuvastatin, simvastatin, and any combination thereof. In another embodiment, the second medicament elevates the level of HDL-cholesterol. In some embodiments, the subject or the individual is mammal, preferably human.

In one aspect, the present invention relates to a method of detecting PCSK9 protein in a sample, the method comprises: (a) contacting the sample with any of the anti-PCSK9 antibodies or fragments thereof described herein; and (b) detecting the formation of a complex between the anti-PCSK9 antibody or fragments thereof and the PCSK9 protein. In one embodiment, the anti-PCSK9 antibody is detectably labeled.

The present invention also encompasses any combination of any of the embodiments described herein. Any of the embodiments described herein, or any combination thereof, is suitable for use in any and all of the anti-PCSK9 antibodies or fragments, methods and uses thereof of the invention described herein.

BRIEF DESCRIPTION OF THE DRAWINGS

FIG. 1 shows the ability of each anti-PCSK9 antibody at various concentrations to block the binding of PCSK9 to LDLR.

FIG. 2 shows that each anti-PCSK9 antibody at various concentrations to increase the capability of HepG2 cells to restore LDLR.

FIG. 3 shows the ability of each anti-PCSK9 antibody at various concentrations to reduce the cellular internalization of LDLR.

FIG. 4 shows the sequence information of FR and CDR of the exemplary antibodies of the present invention.

FIG. 5 shows the sequence information of the heavy chain variable region and the light chain variable region of the exemplary antibodies of the present invention.

DETAILED DESCRIPTION OF THE INVENTION

Definition

Figure 6:
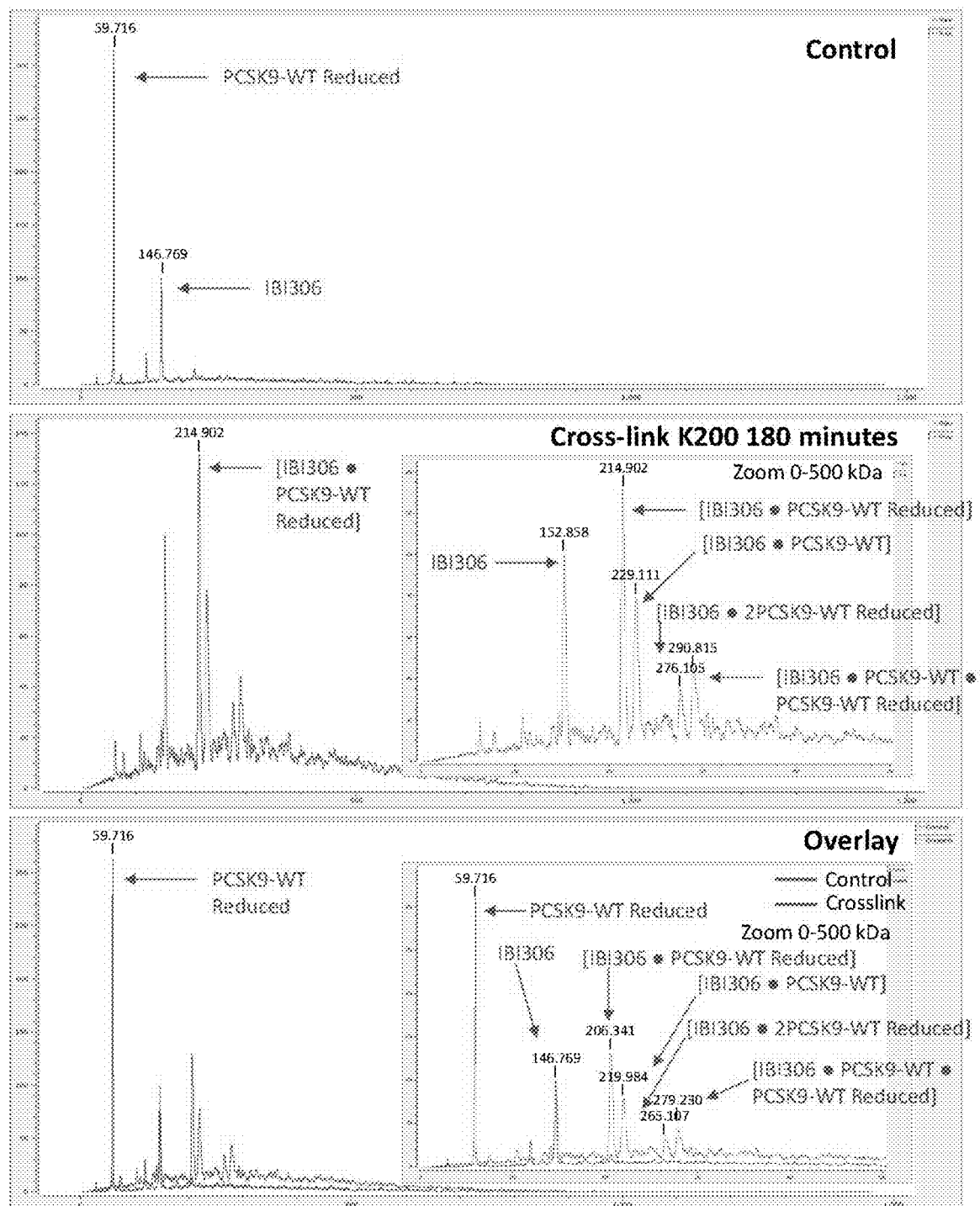
FIG. 6 shows HM4 High Mass MALDI ToF analysis of the complex anti-PCSK9 antibody/PCSK9-WT, wherein anti-PCSK9 antibody=0.5 μM; PCSK9-WT=4 μM, total volume=10 μl; cross-linking: K200, incubation time of 180 min.

Before the present invention is described in detail below, it is to be understood that the invention is not limited to the particular methodology, solutions, and reagents described herein, as these may vary. It is also understood that the terminology used herein is for the purpose of describing the particular embodiments and is not intended to limit the scope of the invention, which will only be restricted by the appended claims. All technical and scientific terms used herein have the same meaning as commonly understood by those skilled in the art to which this invention belongs, unless otherwise defined.

For the purpose of interpreting the specification, the following definitions will be used, and the terms used in the singular may also include the plural, vice versa, if appropriate. It is understood that the terminology used herein is for the purpose of describing particular embodiments and is not intended to be restrictive.

The term "about" when used in connection with a numerical value is meant to encompass numerical values within the range between the lower limit of 5% less than the specified numerical value and the upper limit of 5% greater than the specified numerical value.

"Affinity" refers to the strength of the sum of all non-covalent interactions between a single binding site of a molecule (e.g., an antibody) and its binding partner (e.g., an antigen). As used herein, "binding affinity" refers to the intrinsic binding affinity that reflects a 1:1 interaction between members of a binding pair (e.g., an antibody and an antigen), unless otherwise indicated. The affinity of molecule X for its partner Y is generally expressed by the equilibrium dissociation constant ($K_D$). Affinity can be measured by conventional methods known in the art, including those known in the art and described herein.

The term "anti-PCSK9 antibody", "anti-PCSK9", "PCSK9 antibody" or "antibody binding to PCSK9" refers to an antibody which is capable of binding to PCSK9 protein or a fragment thereof with sufficient affinity such that the antibody can be used as diagnostic and/or therapeutic agent targeting PCSK9. In one embodiment, the anti-PCSK9 antibody binds to an unrelated, non-PCSK9 protein to an extent lesser than about 10% of the binding of the antibody to PCSK9, as measured, for example, by radioimmunoassay (RIA). In some embodiments, the anti-PCSK9 antibody has an equilibrium dissociation constant ($K_D$) of ≤1 μM, ≤100 nM, ≤10 nM, ≤1 nM, ≤0.1 nM, ≤0.01 nM, or ≤0.001 nM (e.g., $10^{-8}$M or less, e.g., from $10^{-8}$M to $10^{-13}$M, e.g., from $10^{-9}$M to $10^{-13}$M).

As used herein, "monoclonal antibody" or "mAb" refers to a single copy or cloned antibody derived from, for example, a eukaryotic, a prokaryotic, or a phage clone, while does not refer to a method of producing the same. Monoclonal antibodies or antigen-binding fragments thereof can be produced, for example, by hybridoma technology, recombinant technique, phage display technique, synthetic technique such as CDR grafting, or a combination of such or other techniques known in the art.

"Antibody fragment" refers to a molecule other than an intact antibody, and it comprises a portion of an intact antibody that binds to an antigen to which the intact antibody binds.

"An antibody that binds to the same epitope" as a reference antibody refers to an antibody that blocks 50% or more of the binding of the reference antibody to its antigen in a competitive assay. On the contrary, the reference antibody blocks 50% or more of the binding of the antibody to its antigen in a competitive assay.

There are five major classes of antibodies known in the art: IgA, IgD, IgE, IgG and IgM, and several of these antibodies can be further divided into subclasses (isotypes), for example, $IgG_1$, $IgG_2$, $IgG_3$, $IgG_4$, $IgA_1$ and $IgA_2$. The heavy chain constant domains corresponding to different classes of immunoglobulins are referred to as α, δ, ε, γ, and μ, respectively.

The term "cytotoxic agent" as used in the present invention refers to a substance which inhibits or prevents from cell function and/or causes cell death or disruption.

The term "diabody" refers to an antibody fragment having two antigen binding sites, and said antibody fragment comprises a heavy chain variable domain (VH) linked to a light chain variable domain (VL) in the same polypeptide chain (VH-VL). The domains are forced to pair with the complementary domains on the other chain to create two antigen binding sites, by using a linker that is too short to make the two domains on the same chain be paired with each other. A diabody can be bivalent or bispecific. Diabodies are more fully described, for example, in EP 404,097; WO 1993/01161; Hudson et al, Nat. Med. 9: 129-134 (2003); and Hollinger et al., Proc. Natl. Acad. Sci. USA 90:6444-6448 (1993). Triabodies and tetrabodies are also described in Hudson et al, Nat. Med. 9: 129-134 (2003).

"Effector function" refers to those biological activities attributable to the Fc region of an antibody, which vary with the antibody isotypes. Examples of antibody effector's functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

The term "effective amount" refers to an amount or dose of an antibody or fragment of the invention that produces the desired effect in a patient to be treated, when administered to the patient in single or multiple doses. An effective amount can be readily determined by the attending physician as a person skilled in the art by considering various factors such as the species of the mammal; its size, age and general health; the particular disease involved; the extent or severity of the disease; the response of an individual patient; the specific antibody to be administered; mode of administration; bioavailability characteristics of the formulation to be administered; selected dosing regimen; and use of any concomitant therapy.

"Antibodies and antigen-binding fragments thereof" suitable for use in the present invention include, but are not limited to, polyclonal, monoclonal, monovalent, bi specific, heteroconjugate, multi specific, recombinant, heterologous, heterozygous, chimeric, humanized (especially grafted with CDRs), deimmunized, or human antibody, Fab fragments, Fab' fragments, F(ab')$_2$ fragments, fragments produced by Fab expression library, Fd, Fv, disulfide-linked Fv (dsFv), single-chain antibody (e.g., scFv), diabody or tetrabody (Holliger P. et al. (1993) Proc. Natl. Acad. Sci. USA 90 (14), 6444-6448), nanobody (also referred to as a single domain antibody), anti-idiotypic (anti-Id) antibody (including, for example, an anti-Id antibody against the antibody of the invention), and epitope-binding fragments of any of the above.

A "Fab" fragment includes a heavy chain variable domain and a light chain variable domain, and also includes a constant domain of the light chain and a first constant domain of the heavy chain (CH1). Fab' fragments differ from Fab fragments by the addition of some residues at the carboxyl terminus of the heavy chain CH1 domain, including one or more cysteines derived from the antibody hinge region. Fab'-SH is the designation herein for a Fab' in which a cysteine residue within a constant domain carries a free thiol group. F(ab')2 antibody fragment was originally produced as a pair of Fab' fragments with a hinge cysteine between the Fab' fragments. Other chemical couplings of antibody fragments are also known.

The term "Fc region" is used herein to define a C-terminal region of an immunoglobulin heavy chain, and the Fc region comprises at least a portion of the constant region. The term includes native Fc region sequence and Fc region variants. In certain embodiments, the human IgG heavy chain Fc region extends from Cys226 or Pro230 to the carbonyl terminus of the heavy chain. However, the C-terminal lysine (Lys447) of Fc region may or may not be present. Unless otherwise indicated, the amino acid residues in Fc region or constant region are numbered according to the EU numbering system, which is also referred to as the EU index, as described in Kabat et al., Sequences of Proteins of Immunological Interest, 5th Ed. Public Health Service, National. Institutes of Health, Bethesda, Md., 1991.

"Framework" or "FR" refers to variable domain residues other than hypervariable region (HVR) (e.g., complementarity determining region) residues. The FR of a variable domain typically consists of four FR domains: FR1, FR2, FR3 and FR4. Accordingly, the HVR and FR sequences generally appear in the following sequence in the heavy chain variable domain (VH) (or the light chain variable domain (VL)): FR1-H1(L1)-FR2-H2(L2)-FR3-H3 (L3)-FR4.

The terms "full length antibody", "intact antibody" and "whole antibody" are used herein interchangeably to refer to an antibody having a structure substantially similar to a native antibody structure or having heavy chains that contain an Fc region as defined herein.

"Fv" is the smallest antibody fragment that contains the entire antigen binding site. In one embodiment, the double-stranded Fv species consists of a dimer wherein one heavy chain variable domain and one light chain variable domain is tightly and non-covalently associated. In single-chain Fv (scFv) species, one heavy chain variable domain can be covalently linked to one light chain variable domain by a flexible peptide linker such that the light and heavy chains can associated into a "dimer" structure similar to double-stranded Fv species. In this configuration, the three HVRs within each variable domain interact with each other to define an antigen binding site located on the surface of the VH-VL dimer. In summary, six HVRs confer antigen binding specificity to the antibody. However, even a single variable domain (or half of Fv only comprising the three HVRs specific for an antigen) has the ability to recognize and bind to the antigen, although the affinity is lower than the intact binding site. For a review of scFv, see, for example, Pluckthun in The Pharmacology of Monoclonal Antibodies, Vol. 113, Rosenburg and Moore eds. (Springer-Verlag, New York, 1994), pp. 269-315.

The terms "host cell", "host cell line" and "host cell culture" are used interchangeably and refer to cells into which exogenous nucleic acid has been introduced, including the progeny of such cells. Host cells include "transformants" and "transformed cells", which include the primary transformed cell and progeny derived therefrom regardless of the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subtype of variable domain sequences. Generally, the subtype of the sequences is a subtype as defined in Kabat et al., Sequences of Proteins of Immunological Interest, Fifth Edition, NIH Publication 91-3242, Bethesda Md. (1991), vols. 1-3. In a embodiment, for the VL, the subtype is subtype kappa I as in Kabat et al., supra. In some embodiments, for the VH, the subtype is subtype III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypercholesterolemia" as used herein refers to a condition in which the level of cholesterol is increased above the desired level. In some embodiments, the level of LDL-cholesterol is increased above the desired level. In some embodiments, the serum level of LDL-cholesterol is increased above the desired level.

An "immunoconjugate" is an antibody conjugated to one or more heterologous molecule(s), including but not limited to a cytotoxic agent.

An "individual" or "subject" includes a mammal. Mammals include, but are not limited to, domestic animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated antibody" is one which has been separated from a component of its natural environment. In some embodiments, an antibody is purified to greater than 95% or 99% purity, for example, as determined by, e.g., electrophoresis (e.g., SDS-PAGE, isoelectric focusing (IEF), capillary electrophoresis) or chromatography (e.g., ion exchange or reverse phase HPLC). For a review of methods for assessment of antibody purity, see, e.g., Flatman et al., J. Chromatogr. B 848:79-87 (2007).

An "isolated nucleic acid" refers to a nucleic acid molecule that has been separated from a component of its natural environment. An isolated nucleic acid includes a nucleic acid molecule contained in cells that ordinarily contain the nucleic acid molecule, but the nucleic acid molecule is present outside the chromosomes or at a chromosomal location that is different from its natural chromosomal location.

An "isolated nucleic acid encoding an anti-PCSK9 antibody or antigen-binding fragment thereof" refers to one or more nucleic acid molecules encoding the heavy and light chain of an antibody or antigen-binding fragment thereof, including such nucleic acid molecules contained in a single vector or in separate vectors, as well as such nucleic acid molecules present at one or more locations within a host cell.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways in the art, for instance, using publicly available computer software such as BLAST®, BLAST-2, ALIGN or MEGALIGN (DNASTAR) software. Those skilled in the art can determine appropriate parameters for aligning sequences, including any algorithm needed to achieve maximal alignment over the full length of the sequences being compared.

When percentages of sequence identity are referred to in this application, these percentages are calculated relative to the full length of the longer sequence, unless otherwise specifically indicated. The calculation relative to the full length of the longer sequence applies to both the nucleic acid sequence and the polypeptide sequence.

The term "pharmaceutical composition" refers to a formulation which is in such form as to permit the biological activity of an active ingredient contained therein to be effective, and which contains no additional components which are unacceptably toxic to a subject to which the formulation would be administered.

The term "pharmaceutically acceptable carrier" refers to a diluent, adjuvant (e.g., Freund's adjuvant (complete and incomplete)), excipient or vehicle co-administered with the therapeutic agent.

Unless otherwise indicated, the term "proprotein convertase subtilisin/kexin type 9 (PCSK9)", "PCSK9" or "NARC-1" as used herein refers to any natural PCSK9 derived from any vertebrate origin, including mammals such as primates (e.g., humans) and rodents (e.g., mice and rats), unless otherwise indicated. The term encompasses "full length" unprocessed PCSK9 as well as any form of PCSK9 or any fragment thereof produced via intracellular processing. The term also encompasses naturally occurring PCSK9 variants, for example, splice variants or allelic variants.

The term "PCSK9 activity" or "biological activity" of PCSK9, when used herein, includes any biological effect of PCSK9. In some embodiments, the PCSK9 activity comprises the ability of PCSK9 to interact with or bind to a substrate or receptor. In some embodiments, the biological activity of PCSK9 is the ability of PCSK9 to bind to LDL-receptor (LDLR). In some embodiments, PCSK9 binds to and catalyzes a reaction involving LDLR. In some embodiments, PCSK9 activity includes the ability of PCSK9 to reduce or decrease the availability of LDLR. In some embodiments, the biological activity of PCSK9 includes the ability of PCSK9 to increase the amount of LDL in a subject. In some embodiments, the biological activity of PCSK9 includes the ability of PCSK9 to reduce the amount of LDLR available in a subject to bind to LDL. In some embodiments, the biological activity of PCSK9 includes the ability of PCSK9 to reduce the amount of LDLR available bind to LDL. In some embodiments, the biological activity of PCSK9 includes any biological activity resulting from PCSK9 signaling.

As used herein, "treating" refers to slowing, interrupting, arresting, ameliorating, stopping, reducing, or reversing the progression or severity of an existing symptom, condition, disorder, or disease.

The term "variable region" or "variable domain" refers to the domain of an antibody heavy or light chain that is involved in binding the antibody to antigen. The variable domains of the heavy chain and light chain of a native antibody generally have similar structures, with each domain comprising four conserved framework regions (FRs) and three complementary determinant region. (See, e.g., Kindt et al. Kuby Immunology, $6^{th}$ ed., W.H. Freeman and Co., page 91 (2007).) A single VH or VL domain may be sufficient to confer antigen-binding specificity. Furthermore, antibodies that bind to a particular antigen may be isolated using a VH or VL domain from an antibody that binds to the antigen to screen a library of complementary VL or VH domains, respectively. See, e.g., Portolano et al., J. Immunol. 150:880-887 (1993); Clarkson et al., Nature 352: 624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "cholesterol-related diseases" includes any one or more selected from the group consisting of hypercholesterolemia, hyperlipidemia, heart disease, metabolic syndrome, diabetes mellitus, coronary heart disease, stroke, cardiovascular diseases, Alzheimers disease, and general dyslipidemia (which shows as, for example, increased level of total serum cholesterol, increased level of LDL, increased level of triglyceride, increased level of VLDL and/or low level of HDL). Some non-limiting examples of primary and secondary dyslipidemia which can be treated with an anti-PCSK9 antibody (alone or in combination with one or more other drugs) include metabolic syndrome, diabetes mellitus, familial combined hyperlipidemia, familial hypertriglyceridemia, familial hypercholesterolemias, including heterozygous hypercholesterolemia, homozygous hypercholesterolemia, familial defective apolipoprotein B-100; polygenic hypercholesterolemia; remnant removal disease, hepatic lipase deficiency; dyslipidemia secondary to any of dietary indiscretion, hypothyroidism, drugs (including estrogen and progesterone therapy, beta blockers, and thiazide diuretics)); nephrotic syndrome, chronic renal failure, Cushing's syndrome, primary biliary cirrhosis, glycogen storage diseases, hepatoma, cholestasis, acromegaly, insulinoma, isolated growth hormone deficiency and alcohol-induced hypertriglyceridemia.

Antibody of the Present Invention

In one aspect of the invention, provided herein is an anti-PCSK9 antibody, as well as antigen-binding fragments thereof. In some embodiments, the anti-PCSK9 antibody inhibits or blocks PCSK9 activity. In certain embodiments, the antibody provided herein has an equilibrium dissociation constant (KD) of ≤about 1 μM, ≤about 100 nM, ≤about 10 nM, ≤about 1 nM, ≤about 0.1 nM, ≤about 0.01 nM, or ≤about 0.001 nM (e.g., $10^{-8}$M or less, e.g., from $10^{-8}$M to $10^{-13}$M, e.g., from $10^{-9}$M to $10^{-13}$M).

In some embodiments, an anti-PCSK9 antibody or antigen-binding fragments thereof of the invention comprises a heavy chain variable region (HCVR), wherein the HCVR comprises complementarity determining regions (CDRs) HCDR1, HCDR2 and HCDR3, wherein HCDR1 comprises or consists of amino acid sequence having at least 90%, 91%, 92%, 93%, 94%, 95%, 96%, 97%, 98% or 99% identity or 100% identity to the amino acid sequence selected from the group consisting of SEQ ID NOs: 1, 7, 8, 9, 10, 11, 12, 13 and 20, HCDR2 comprises or consists of amino acid sequence having at least 90%, 91%, 92%, 93%, 94%, 95%, 96%, 97%, 98% or 99% identity or 100% identity to the amino acid sequence selected from the group consisting of SEQ ID NOs:2, 14, 15, 16, 17 and 21, and HCDR3 comprises or consists of amino acid sequence having at least 90%, 91%, 92%, 93%, 94%, 95%, 96%, 97%, 98% or 99% identity or 100% identity to the amino acid sequence selected from the group consisting of SEQ ID NOs: 3, 18, 19 and 22. In certain embodiments, the amino acid sequence of the CDRs of the anti-PCSK 9 antibody HCVR (e.g., the CDRs having at least 90%, 91%, 92%, 93%, 94%, 95%, 96%, 97%, 98% or 99% identity or 100% identity to the reference sequence) comprises one or more substitutions (e.g., conservative substitutions), insertions or deletions relative to the corresponding reference sequence, while the anti-PCSK9 antibody comprising said CDRs has the ability to bind to PCSK9.

In some embodiments, an anti-PCSK9 antibody or antigen-binding fragments thereof of the invention comprises a light chain variable region (LCVR), wherein the LCVR comprises complementarity determining regions (CDRs) LCDR1, LCDR2 and LCDR3, wherein LCDR1 comprises or consists of amino acid sequence having at least 90%, 91%, 92%, 93%, 94%, 95%, 96%, 97%, 98% or 99% identity or 100% identity to the amino acid sequence of SEQ ID NO: 4, LCDR2 comprises or consists of amino acid sequence having at least 90%, 91%, 92%, 93%, 94%, 95%, 96%, 97%, 98% or 99% identity or 100% identity to the amino acid sequence of SEQ ID NO: 5, and LCDR3 comprises or consists of amino acid sequence having at least 90%, 91%, 92%, 93%, 94%, 95%, 96%, 97%, 98% or 99% identity or 100% identity to the amino acid sequence of SEQ ID NO: 6. In certain embodiments, the amino acid sequence of the CDRs of the anti-PCSK 9 antibody LCVR (e.g., the CDRs having at least 90%, 91%, 92%, 93%, 94%, 95%, 96%, 97%, 98% or 99% identity or 100% identity to the reference sequence) comprises one or more substitutions (e.g., conservative substitutions), insertions or deletions relative to the corresponding reference sequence, while the anti-PCSK9 antibody comprising said CDRs has the ability to bind to PCSK9.

In some embodiments, an anti-PCSK9 antibody or antigen-binding fragments thereof of the invention comprises a heavy chain variable region (HCVR), wherein the heavy chain variable region HCVR comprises or consists of amino acid sequence having at least 90%, 91%, 92%, 93%, 94%, 95%, 96%, 97%, 98% or 99% identity or 100% identity to the amino acid sequence selected from the group consisting of SEQ ID NOs: 23, 25, 26, 27, 28, 29, 30, 31, 32 and 33. In some embodiments, the heavy chain variable region HCVR of the anti-PCSK antibody comprises amino acid sequence having one or more substitutions (e.g., conservative substitutions), insertions or deletions relative to the amino acid sequence selected from the group consisting of SEQ ID NOs: 23, 25, 26, 27, 28, 29, 30, 31, 32 and 33, while an anti-PCSK9 antibody comprising said HCVR has the ability to bind to PCSK9.

In some embodiments, an anti-PCSK9 antibody or antigen-binding fragments thereof of the invention comprises a light chain variable region (LCVR), wherein the light chain variable region LCVR comprises or consists of amino acid sequence having at least 90%, 91%, 92%, 93%, 94%, 95%, 96%, 97%, 98% or 99% identity or 100% identity to the amino acid sequence of SEQ ID NO: 24. In some embodiments, the light chain variable region LCVR of the anti-PCSK antibody comprises amino acid sequence having one or more substitutions (e.g., conservative substitutions), insertions or deletions relative to the amino acid sequence of SEQ ID NOs: 24, while an anti-PCSK9 antibody comprising said LCVR has the ability to bind to PCSK9.

In some embodiments, an anti-PCSK9 antibody or antigen-binding fragments thereof of the invention comprises a heavy chain, wherein the heavy chain comprises or consists of amino acid sequence having at least 90%, 91%, 92%, 93%, 94%, 95%, 96%, 97%, 98% or 99% identity or 100% identity to the amino acid sequence selected from the group consisting of SEQ ID NOs: 34, 36, 37, 38, 39, 40, 41, 42, 43 and 44. In some embodiments, the heavy chain of the anti-PCSK antibody comprises amino acid sequence having one or more substitutions (e.g., conservative substitutions), insertions or deletions relative to the amino acid sequence selected from the group consisting of SEQ ID NOs: 34, 36, 37, 38, 39, 40, 41, 42, 43 and 44, while an anti-PCSK9 antibody comprising said heavy chain has the ability to bind to PCSK9.

In some embodiments, an anti-PCSK9 antibody or antigen-binding fragments thereof of the invention comprises a light chain, wherein the light chain comprises or consists of amino acid sequence having at least 90%, 91%, 92%, 93%, 94%, 95%, 96%, 97%, 98% or 99% identity or 100% identity to the amino acid sequence of SEQ ID NO:35. In some embodiments, the light chain of the anti-PCSK antibody comprises amino acid sequence having one or more substitutions (e.g., conservative substitutions), insertions or deletions relative to the amino acid sequence of SEQ ID NO: 35, while an anti-PCSK9 antibody comprising said light chain has the ability to bind to PCSK9.

In a preferred embodiment, the substitutions, insertions or deletions occur outside the CDR (e.g., within FR). Optionally, an anti-PCSK9 antibody of the invention comprises post-translational modifications to the light chain variable region, the heavy chain variable region, the light chain or the heavy chain.

In some embodiments, the substitution is conservative substitution. Conservative substitution means that one amino acid is replaced by another amino acid within the same class, for example, one acidic amino acid is replaced by another acidic amino acid, one basic amino acid is replaced by another basic amino acid, or one neutral amino acid is replaced by another neutral amino acid. Exemplary substitutions are shown in Table A below:

TABLE A

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed. In some applications, modifications that remove unwanted glycosylation sites may be useful, or for example, modifications that remove fucose modules so as to enhance the antibody-dependent cellular cytotoxicity (ADCC) function (see Shield et al. (2002) JBC 277: 26733). In other applications, galactosylation modification may be performed to modify complement-dependent cytotoxicity (CDC).

In certain embodiments, one or more amino acid modifications may be introduced into the Fc region of an antibody provided herein, thereby generating an Fc region variant, so as to enhance the efficiency of the antibody, for example, in the treatment of diseases or conditions involving abnormal angiogenesis and/or vascular permeability or leakage. The Fc region variant may comprise human Fc region sequence (e.g., human IgG1, IgG2, IgG3 or IgG4 Fc region) comprising an amino acid modification (e.g. a substitution) at one or more amino acid positions.

In certain embodiments, it may be desirable to create cysteine engineered antibodies, e.g., "thioMAbs," in which one or more residues of an antibody are substituted with cysteine residues.

In certain embodiments, an antibody provided herein may be further modified to contain additional non-proteinous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, poly-amino acids (either homopolymers or random copolymers), and glucan or poly(n-vinyl pyrrolidone) polyethylene glycol, propylene glycol homopolymers, polypropylene oxide/ethylene oxide co-polymers, polyoxyethylated polyols (e.g., glycerol), polyvinyl alcohol, and mixtures thereof.

In some embodiments, the invention encompasses fragments of an anti-PCSK9 antibody. Examples of antibody fragments include, but are not limited to, Fv, Fab, Fab', Fab'-SH, F(ab')$_2$, diabody, linear antibody, single chain antibody molecule (e.g., scFv); and multispecific antibody formed by antibody fragments. Two identical antigen-binding fragments produced by papain digestion on antibody are termed "Fab" fragments, in which each has a single antigen-binding site and a residual "Fc" fragment. Its name reflects the ability susceptible to crystallize. F(ab')$_2$ fragment is produced by pepsin treatment, and it has two antigen binding sites and is still capable of cross-linking antigen.

In some embodiments, an anti-PCSK9 antibody of the present invention is a humanized antibody. Different methods for humanizing antibodies are known to those skilled in the art, as reviewed by Almagro & Fransson, the contents of which are incorporated herein by reference in its entirety (Almagro J C and Fransson J (2008) Frontiers in Bioscience 13: 1619-1633). Almagro & Fransson distinguishes a theoretical approach from an empirical approach. A theoretical approach is characterized by generating a few engineered antibody variants and assessing their binding or any other property of interest. If the designed variants do not achieve the expected results, then a new round of design and biding assay is initiated. Theoretical approaches include CDR grafting, Resurfacing, Superhumanization and Human String Content Optimization. In contrast, empirical approaches are based on generating a large library of humanized variants and selecting optimal clones by using enrichment techniques or high-throughput screening. Consequently, empirical approaches rely on reliable selection and/or screening systems that are capable of searching for a large number of antibody variants. In vitro display techniques, such as phage display and ribosome display, meet these requirements and are well known to the skilled artisans. Empirical approaches include FR libraries, Guided selection, Framework-shuffling, and Humaneering.

In some embodiments, an anti-PCSK9 antibody of the invention is a human antibody. Human antibodies may be prepared using a variety of techniques known in the art. Human antibodies are generally described in van Dijk and van de Winkel, Curr. Opin. Pharmacol 5: 368-74 (2001) and Lonberg, Curr. Opin. Immunol 20: 450-459 (2008).

Antibodies of the present invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in Methods in Molecular Biology 178:1-37 (O'Brien et al., ed., Human Press, Totowa, N.J., 2001) and further described, e.g., in the McCafferty et al., Nature 348:552-554; Clackson et al., Nature 352: 624-628 (1991); Marks et al., J. Mol. Biol. 222: 581-597 (1992); Marks and Bradbury, in Methods in Molecular Biology 248:161-175 (Lo, ed., Human Press, Totowa, N.J., 2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132(2004).

In some embodiments, the invention also encompasses an anti-PCSK9 monoclonal antibody conjugated to a therapeutic moiety, such as a cytotoxic agent or an immunosuppressive agent ("immunoconjugates"). Cytotoxic agents include any agent that is harmful to cells. Examples of cytotoxic agents (e.g., chemotherapeutic agents) suitable for forming immunoconjugates are known in the art, see for example WO05/103081. For example, cytotoxic agents include, but are not limited to, radioactive isotopes (e.g., At$^{211}$, I$^{131}$, I$^{125}$, Y$^{90}$, Re$^{186}$, Re$^{188}$, Sm$^{153}$, Bi$^{212}$, P$^{32}$, Pb$^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleic acid hydrolase; antibiotics; toxins such as small molecule toxins or enzymatically active toxins of bacterial, fungal, plant or animal origin, including fragments and/or variants thereof; and various well-known antitumor or anticancer agents.

In some embodiments, an antibody of the invention may be monospecific, bispecific or multispecific. A multispecific monoclonal antibody may be specific for various epitopes of a target polypeptide or may contain antigen binding domains specific for more than one target polypeptides. See, for example, Tutt et al. (1991) J. Immunol. 147: 60-69. An anti-PCSK9 monoclonal antibody may be linked to or co-expressed with another functional molecule, such as another peptide or protein. For example, an antibody or fragments thereof may be functionally linked to one or more other molecules, such as another antibody or antibody fragment (e.g., by chemical coupling, genetic fusion, non-covalent association, or otherwise) to produce a bispecific or multispecific antibody with a second or more binding specificities.

In some embodiments, an antibody of the present invention binds to human PCSK9 protein.

Nucleic Acid of the Present Invention and Host Cell Containing the Same

In one aspect, the invention provides a nucleic acid encoding any of the above anti-PCSK9 antibodies or fragments thereof. The nucleic acid may encode an amino acid sequence comprising a light chain variable region and/or a heavy chain variable region of an antibody, or an amino acid sequence comprising a light chain and/or a heavy chain of an antibody.

In one embodiment, one or more vectors comprising the nucleic acid are provided. In one embodiment, the vector is an expression vector.

In one embodiment, a host cell comprising the vector is provided. Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. See also Charlton, Methods in Molecular Biology, Vol. 248 (B. K. C. Lo, ed., Humana Press, Totowa, N.J., 2003, pp. 245-254, describing expression of antibody fragments in E.

coli. After expression, the antibody may be isolated from the bacterial cell paste in a soluble fraction and can be further purified.

In one embodiment, the host cell is eukaryotic. In another embodiment, the host cell is selected from the group consisting of a yeast cell, a mammalian cell, or other cells suitable for use in the preparation of an antibody or antigen-binding fragments thereof. For example, eukaryotic microorganisms such as filamentous fungi or yeast are cloning or expression hosts suitable for vectors encoding antibodies, including fungi and yeast strains, glycosylation pathways of which have been "humanized", resulting in the production of antibodies with partial or complete human glycosylation pattern. See Gerngross, Nat. Biotech. 22: 1409-1414 (2004), and Li et al, Nat. Biotech. 24: 210-215 (2006). Host cells suitable for expression of glycosylated antibodies are also derived from multicellular organisms (invertebrates and vertebrates). Vertebrate cells can also be used as hosts. For example, mammalian cell lines which have been engineered to be suitable for suspension growth may be used. Other examples of useful mammalian host cell lines are the monkey kidney CV1 line (COS-7) transformed with SV40; human embryonic kidney line (293 or 293 cells, e.g., as described in such as Graham et al, J. Gen Virol. 36:59 (1977)), and so on. Other useful mammalian host cell lines include Chinese hamster ovary (CHO) cells, including DHFR-CHO cells (Urlaub et al, Proc. Natl. Acad. Sci. USA 77: 216 (1980)); and myeloma cell lines such as YO, NSO and Sp2/0. For a review of certain mammalian host cell lines suitable for producing antibodies, see, for example, Yazaki and Wu, Methods in Molecular Biology, Vol. 248 (B. K. C. Lo, ed., Humana Press, Totowa, N.J.), pp. 255-268 (2003).

In one embodiment, provided is a method of preparing an anti-PCSK9 antibody, wherein the method comprises cultivating a host cell comprising a nucleic acid encoding the antibody under conditions suitable for expressing the antibody, as provided above, and optionally, recovering the antibody from the host cell (or the host cell culture medium). For recombinant production of an anti-PCSK9 antibody, a nucleic acid encoding an antibody (such as the antibody described above) is isolated and inserted into one or more vectors for further cloning and/or expression in a host cell. Such nucleic acids are readily isolated and sequenced using conventional procedures (e.g., by using oligonucleotide probes capable of specifically binding to genes encoding the heavy and light chain of an antibody).

Pharmaceutical Composition and Pharmaceutical Formulation

The invention also encompasses a composition (including a pharmaceutical composition or a pharmaceutical formulation) comprising an anti-PCSK9 antibody and a composition comprising a polynucleotide encoding an anti-PCSK9 antibody. In certain embodiments, the composition comprises one or more antibodies binding to PCSK9 or one or more polynucleotides encoding one or more antibodies that bind to PCSK9. These compositions may also comprise suitable pharmaceutically acceptable carriers such as pharmaceutical excipients known in the art, including buffers.

Pharmaceutically acceptable carriers suitable for use in the present invention may be sterile liquids such as water and oils, including those from petroleum, animal, plant or synthetic origin, such as peanut oil, soybean oil, mineral oil, sesame oil and the like. Water is a preferred carrier when the pharmaceutical composition is administered intravenously. Saline solution and aqueous dextrose and glycerol solution can also be used as liquid carriers, especially used as injectable solutions. Suitable pharmaceutical excipients include starch, glucose, lactose, sucrose, gelatin, malt, rice, flour, chalk, silica gel, sodium stearate, glyceryl monostearate, talc, sodium chloride, dried skim milk, glycerin, propylene, glycol, water, ethanol, etc. For excipients and the uses thereof, see also "Handbook of Pharmaceutical Excipients", Fifth Edition, R. C. Rowe, P. J. Seskey and S. C. Owen, Pharmaceutical Press, London, Chicago. If desired, the composition may also contain minor amounts of wetting or emulsifying agents, or pH buffer. These compositions may be in the form of solutions, suspensions, emulsions, tablets, pills, capsules, powders, sustained release preparations and the like. Oral formulations may contain standard carriers such as pharmaceutical grades of mannitol, lactose, starch, magnesium stearate, saccharin.

A pharmaceutical formulation comprising an anti-PCSK9 antibody of the invention can be prepared by mixing the anti-PCSK9 antibody of the present invention having desired purity with one or more optional pharmaceutical carriers (Remington's Pharmaceutical Sciences, 16th Ed., Osol, A., ed. (1980)), preferably in the form of a lyophilized preparation or an aqueous solution.

Exemplary lyophilized antibody formulations are described in U.S. Pat. No. 6,267,958. Aqueous antibody formulations include those described in U.S. Pat. No. 6,171, 586 and WO2006/044908, and the latter includes histidine-acetate buffer.

The pharmaceutical compositions or formulations of the present invention may also contain more than one active ingredient which is required for a particular indication to be treated, preferably those active ingredients which do not adversely affect each other's complementary activities. For example, it is desirable to further provide statins. The active ingredient is suitably present in combination in an amount effective for the intended use.

Sustained release formulations can be prepared. Suitable examples of the sustained release formulations include semipermeable matrices of solid hydrophobic polymers containing antibodies, the matrices are in the form of shaped articles, such as films or microcapsules.

Method for Treatment and Use of Antibodies

In one aspect, the invention relates to a method of inhibiting the binding of PCSK9 to LDL-receptor (LDLR) in a subject, the method comprises administering an effective amount of any of the anti-PCSK9 antibodies or fragments thereof described herein to the subject. In another aspect, the invention relates to a method of lowering the level of cholesterol in a subject, the method comprises administering an effective amount of any of the anti-PCSK9 antibodies or fragments thereof described herein to the subject. In one embodiment, the cholesterol is LDL-cholesterol. In another aspect, the invention relates to a method of lowering the level of LDL-cholesterol in a subject, the method comprises administering an effective amount of any of the anti-PCSK9 antibodies or fragments thereof described herein to the subject. In some embodiments, the invention relates to a method of lowering the serum level of LDL-cholesterol in a subject, the method comprises administering an effective amount of any of the anti-PCSK9 antibodies or fragments thereof described herein to the subject. In another aspect, the invention relates to a method of treating a condition associated with the elevated level of LDL-cholesterol in a subject, the method comprises administering an effective amount of any of the anti-PCSK9 antibodies or fragments thereof described herein to the subject. In one aspect, the invention relates to a method of treating cholesterol-related diseases, the method comprises administering an effective amount of any of the anti-PCSK9 antibodies or fragments thereof described herein to the subject. In some embodiments, the invention relates to a method of treating hypercholesterolemia and/or hyperlipidemia, the method comprises administering an effective amount of any of the anti-PCSK9 antibodies or fragments thereof described herein to the subject. In one aspect, the invention relates to a method of treating any disease or condition which may be ameliorated, slowed, inhibited or prevented by eliminating, inhibiting or reducing the activity of PCSK9. In some embodiments, diseases or conditions which can be treated or prevented by statins can also be treated with any of the anti-PCSK9 antibodies or fragments thereof described herein. In some embodiments, diseases or conditions which can be benefited from the prevention of cholesterol synthesis or the increased LDLR expression can also be treated with any of the anti-PCSK9 antibodies or fragments thereof described herein. Preferably, the subject is a human.

In other aspects, the invention provides use of an anti-PCSK9 antibody in the manufacture or preparation of a medicament for the treatment of related diseases or conditions as mentioned above.

In certain embodiments, antibodies or antibody fragments against PCSK9 of the invention may be administered prophylactically to prevent or alleviate the onset of hypercholesterolemia, hyperlipidemia, cardiovascular diseases, and/or the onset of any of the cholesterol-related diseases. In certain embodiments, antibodies or antibody fragments against PCSK9 of the invention can be administered to treat the existing hypercholesterolemia and/or hyperlipidemia. In some embodiments, antibodies or antibody fragments of the invention will delay the onset of conditions and/or symptoms associated with the conditions.

In certain embodiments, the methods and uses described herein further comprise administering an effective amount of at least one of additional therapeutic agents to the individual, such as statins, including but not limited to atorvastatin, fluvastatin, lovastatin, mevastatin, pitavastatin, pravastatin, rosuvastatin, simvastatin or any combination thereof, for example, VYTORIN®, ADVICOR® or SIMCOR®. In certain embodiments, the additional therapeutic agents are used for preventing and/or treating atherosclerosis and/or cardiovascular diseases. In certain embodiments, the additional therapeutic agents are used for reducing the risk of relapse of cardiovascular events. In certain embodiments, the additional therapeutic agents are used for increasing the level of HDL-cholesterol in a subject.

The combination therapies mentioned above include co-administration (wherein two or more therapeutic agents are comprised in the same or separate preparations) and separate administration, wherein the administration of an anti-PCSK9 antibody of the invention may occur prior to, simultaneously as and/or after the administration of the additional therapeutic agents/adjuvant.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Administration can be via any suitable route, e.g. by injections, such as intravenous or subcutaneous injections, depending to some extent on whether the administration is for short or long term. Various timing course for adminstration including but not limited to single or multiple administrations over various time-points, bolus administration, and pulse infusion are contemplated herein.

For the prevention or treatment of diseases, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Exemplary dosage range for the antibody includes 3-30 mg/kg.

Methods and Compositions for Diagnosis and Detection

In certain embodiments, any of the anti-PCSK9 antibodies or antigen-binding fragments thereof provided herein can be used for detection of the presence of PCSK9 in a biological sample. The term "detection" as used herein, includes quantitative or qualitative detection. In certain embodiments, the biological sample is blood, serum or other liquid sample derived from organisms. In certain embodiments, the biological sample comprises cells or tissues.

In one embodiment, an anti-PCSK9 antibody for use in a diagnostic or detection method is provided. In another aspect, a method of detecting the presence of PCSK9 in a biological sample is provided. In certain embodiments, the method comprises detecting the presence of PCSK9 protein in a biological sample. In certain embodiments, PCSK9 is human PCSK9. In certain embodiments, the method comprises contacting a biological sample with an anti-PCSK9 antibody as described herein under conditions allowing the binding of the anti-PCSK9 antibody to PCSK9, and detecting whether a complex is formed between the anti-PCSK9 antibody and PCSK9. The method may be an in vitro or in vivo method. In one embodiment, an anti-PCSK9 antibody is used to select a subject suitable for the treatment with an anti-PCSK9 antibody, for example, wherein PCSK9 or LDL-cholesterol is a biomarker for selecting a patient.

In one embodiment, an antibody of the invention can be used for the diagnosis of cholesterol-related diseases, such as hypercholesterolemia and/or hyperlipidemia.

In certain embodiments, a labeled anti-PCSK9 antibody is provided. Labels include, but are not limited to, labels or moieties (such as fluorescent labels, chromophore labels, electron dense labels, chemiluminescent labels, and radioactive labels) directly detected, as well as moieties indirectly detected, such as enzymes or ligands, for example, by enzymatic reaction or molecular interaction. Exemplary labels include, but are not limited to, radioisotopes $^{32}P$, $^{14}C$, $^{125}I$, $^{3}H$, and $^{131}I$, fluorophores such as rare earth chelates or fluorescein and derivatives thereof, rhodamine and derivatives thereof, dansyl, umbelliferone, luciferase, for example, firefly luciferase and bacterial luciferase (U.S. Pat. No. 4,737,456), fluorescein, 2,3-dihydrophthalazinedione, horseradish peroxidase (HR), alkaline phosphatase, β-galactosidase, glucoamylase, lytic enzyme, carbohydrate oxidases, for example, glucose oxidase, galactose oxidase and glucose-6-phosphate dehydrogenase, heterocyclic oxidases such as uricase and xanthine oxidase, plus enzymes that employs hydrogen peroxide to oxidize a dye precursor such as HR, lactoperoxidase, or microperoxidase, biotin/affinity, spin labels, phage labels, stable free radicals, and the like.

The invention is further illustrated by the following examples, which are to be understood by way of illustration and not limitation, a variety of modifications can be made by those skilled in the art.

EXAMPLES

Example 1 Screening Anti-PCSK9 Antibodies to Determine Parent Antibodies

Biotin Labeling of an Antigen

PCSK9 antigen (SEQ ID NO. 53) was labeled with biotin by using a succinimidyl sulfonate biotin labeling kit available from Pierce according to the manufacturer's instructions. FITC-labeled goat anti-human immunoglobulin F(ab') kappa chain antibody (LC-FITC) was purchased from Southern Biotech, polyethylene avidin (SA-PE) was purchased from Sigma, streptavidin-633 (SA-633) was purchased from Molecular Probes. Streptomycin beads and cellular immune magnetic bead separation columns were purchased from Miltenyi LS.

Preliminary Screening

Eight synthetic yeast-based antibody presentation libraries (available from Adimab) were amplified according to existing methods (Xu et al., 2013; WO2009036379; WO 2010105256; WO2012009568), the diversity of each library is up to 1×109. Briefly, the first two rounds of screening were performed by using magnetic activation cell sorting with MACS® system, Miltenyi. First, yeast cells from each library (~1×1010 cells/library) were incubated in FACS washing buffer (phosphate buffer, containing 0.1% bovine serum albumin) for 15 minutes at room temperature, wherein 100 nM biotin-labeled PCSK9 antigen prepared as described above was contained in the buffer. Washing once with 50 ml of pre-cooled FACS washing buffer, and then the cells were re-suspended with 40 ml of the same washing buffer, and added with 500 µl of streptomycin beads and incubated at 4° C. for 5 minutes. After centrifuging at 1000 rpm for 5 min, the supernatant was discarded, and the cells were re-suspended in 5 ml of FACS washing buffer, and the cell solution was added onto a Miltenyi LS column. After the loading was completed, the column was washed 3 times with FACS washing buffer, 3 ml per time. The Miltenyi LS column was removed from the magnetic field, eluted with 5 ml of growth medium, and the eluted yeast cells were collected and grown overnight at 37° C.

The next round of sorting was performed by using a flow cytometer: approximately 1×10⁸ yeast cells obtained by screen with the MACS system were washed three times with FACS buffer, and incubated in PCSK9 antigen or PCSK9-Fc fusion antigen labeled with low concentrations of biotins (100-1 nM) at room temperature. The culture medium was discarded, and the cells were washed twice with FACS washing buffer. The cells then were mixed with LC-FITC (1:100 dilution) and mixed with SA-633 (1:500 dilution) or EA-PE (1:50 dilution) reagent, incubated at 4° C. for 15 minutes. Eluted twice with pre-cooled FACS washing buffer and re-suspended in 0.4 ml buffer, and then the cells were transferred to a separation tube with a filter. Cells were sorted by using FACS ARIA™ (BD Biosciences).

Next, several rounds of screening were performed to obtain competitive ligands and to remove non-specific binders (e.g., membrane proteins of CHO cells). After the final rounds of sorting, the collected yeast cells were plated, incubated overnight at 37° C., and the target single clones were selected. The variable regions of the obtained antibodies were sequenced with Sanger method. A total of approximately 310 antibodies with unique variable region sequences were obtained, and then were identified one by one.

These anti-PCSK9 antibody proteins were obtained through yeast expression and purification with Protein A affinity chromatography.

Production and Purification of Antibodies

The yeast cells expressing an anti-PCSK9 antibody obtained by screening were shaken and induced at 30° C. for 48 hours to express the anti-PCSK9 antibody. After the end of the induction, the yeast cells were removed by centrifuging at 1300 rpm for 10 min, and the supernatant was harvested. The anti-PCSK9 antibody present in the supernatant was purified by using Protein A, eluted with acetic acid solution, pH 2.0, and the anti-PCSK9 antibody was harvested. The antibodies were digested with papain and purified with KappaSelect (GE Life Medical Group), so as to obtain the corresponding Fab fragments.

The gene DNA encoding an anti-PCSK9 antibody was obtained from the above-described yeast cells expressing the anti-PCSK9 antibody, according to a conventional method in the art, and the gene DNA was cloned into a new expression vector (pCDNA3.1) according to a conventional method.

The above expression vector containing the gene of interest antibody and the transfection reagent LIPO-FECTAMINE™ 2000 (purchased from Invitrogen) were transiently transfected into cultured human kidney blast cell 293 cells according to the protocol provided by the manufacturer, the medium was discarded and the cells were diluted with fresh medium to 4×106/ml. The cells were cultured for 7 days at 37° C., with 5% CO2, and added with fresh medium every 48 hours, and 7 days later, centrifuged at 13,000 rpm for 20 min. The supernatant was collected and purified with Protein A to obtain antibodies with purity of >95%.

ForteBio KD Assay (Biofilm Layer Interferometry)

ForteBio Affinity Assay was performed according to the existing method (Estep, P et al, High throughput solution Based measurement of antibody-antigen affinity and epitope binning. MAbs, 2013. 5(2): p. 270-8). Briefly, the sensor was equilibrated off-line in the assay buffer for 30 minutes, and then was tested on-line for 60 seconds to establish a baseline. The purified antibody obtained as described above was loaded online onto the AHQ sensor. The sensor was then placed in 100 nM of PCSK9 antigen for 5 minutes, then the sensor was transferred to assay buffer for dissociation for 5 minutes. The kinetic analysis was performed by using a 1:1 binding model.

MSD-SET Dynamic Detection

The detection of equilibrium affinity was described previously (Estep et al. 2013). Biotin-labeled PCSK9 antigens (b-PCSK9) obtained as described above were added into phosphate buffered saline (PBSF) containing 0.1% IgG-free BSA with a final concentrations of 10-100 pM. Anti-PCSK9 Fabs or mAbs obtained above were 3 to 5-fold serially diluted, and Fab or mAb solutions with concentrations of 5-100 nM were obtained. The antibodies (diluted in 20 nM phosphate buffered saline) were coated on MSD-ECL plates at 4° C. overnight or at room temperature for 30 minutes. 3% BSA was added, blocked at room temperature for 30 minutes at 700 rpm, and then washed 3 times with washing buffer (PBSF+0.05% Tween 20). The samples were added in the plate and placed in a shaker and incubated at room temperature at 700 rpm for 150 seconds, and then washed once. 250 ng/ml of sulfotag-labeled streptavidin (diluted in PBSF) was added and incubated at room temperature for 3 minutes. After washing 3 times with buffer, the antigen bound to the plate was determined using MSD Sector Imager 2400 Reader Device. The percentage of unbound antigen was obtained by antibody titration method. It was found that the binding of anti-PCSK9 Fab or mAb to the antigen was in accordance with the quadratic equation of pharmacokinetics.

Octet Red384 Identification of Binding Epitopes

Identification of binding epitopes was performed with a standard sandwich-type interactively blocking assay. Target-specific control IgG was immobilized on the AHQ sensor and the available Fc binding sites on the sensor were blocked with an irrelevant human IgG1 antibody. The sensor was placed in 100 nM target antigen PCSK9 solution for 120 s and then placed in a second 100 nM anti-PCSK9 antibody or ligand solution prepared as above. Data were read and processed by ForteBio Data Analysis Software 7.0 (from ForteBio). If the antigen can also be bound to a second antibody or ligand after binding to the antibody, it implies the presence of an unbound epitope (non-competitive), if not, it implies the epitope was blocked (competitive or ligand-blocked).

Through the above screening and identification, we obtained some antibodies capable of blocking the binding of PCSK9 to LDLR and capable of binding to both human and mouse PCSK9. To obtain anti-PCSK9 antibodies with higher affinity, we optimized the antibody ADI-02396 by the following method.

Example 2 Affinity Optimization of Anti-PCSK9 Antibodies

VHmut Screening

Mutations were introduced into the antibody heavy chain region by conventional mismatch-PCR in this method. During the PCR process, the probability of base mismatch was increased to about 0.01 bp by using 1 uM highly mutated base analogs dPTP and 8-oxo-dGTP.

The mismatched PCR product obtained was constructed into a vector containing a heavy chain constant region by homologous recombination. In this way, we obtained a secondary library with a library capacity of $1 \times 10^7$ under screening pressures including titer of PCSK9 antigen, competition of unlabeled antigen, and competition with parent antibody. Three rounds of successful screening were performed by FACS method.

CDRH1/CDRH2 Screening

The CDRH3 gene of the progeny antibody obtained by VHmut method was constructed into a CDRH1/CDRH2 gene library with diversity of $1 \times 10^8$ and was subjected to 3 rounds of screening. In the first round, the MACS method was used, and in the second and third rounds, the FACS method was used. The antibody-antigen conjugate was subjected to affinity pressure to select an antibody with the highest affinity.

Optimization of $1^{st}$ round: The first step was to increase the affinity of this anti-PCSK9 antibody with human-murine cross-activity and ligand-competition (ADI-02396 (designated as "parent" antibody)). Briefly, mutations were introduced into the parent antibody (using a "mismatch-PCR" approach) to establish a secondary library of yeast-based antibody presentation. A secondary library with approximately $1 \times 10^7$ size was eventually generated for subsequent enrichment of antibodies with higher affinity. Screening pressures included titer of PCSK9 antigen, competition of unlabeled antigen, and competition with parent antibody. FACS technology was also used to screen target populations (see Chao et al. Nature Protocols, 2006 for particular procedures). After 2-3 rounds of enrichment, the obtained yeast was plated to obtain a single clone. After this work, a total of three progenies with improved affinity, ADI-09111, ADI-09112 and ADI-09113, were obtained. The $K_D$ range of these three antibodies was 1-10 nM as determined by ForteBio Octet. Two progeny antibodies, ADI-09112 and ADI-09113, were used for affinity optimization of the second round.

Affinity optimization of the $2^{nd}$ round: The second step was to increase the affinities of the two anti-PCSK9 mAbs with human-murine cross-activity and ligand-competition, ADI-09112 and ADI-09113 (designated as "parent" antibody). Briefly, a secondary library of yeast-based antibody presentation was created again for each parent antibody. The CDR-H3 and light chain (LC) of a parent antibody were combined with CDR-H1 and CDR-H2 of the gene present in the existing yeast library (designated as "H1/H2" optimization). Ultimately 5 libraries with approximately $1 \times 10^8$ size were generated for subsequent enrichment of antibodies with higher affinity. The screening method is the same as the first round of screening. After 2-3 rounds of enrichment, yeast was plated to obtain a single clone. After this work, progeny antibodies with improved affinity were obtained, of which ADI-10085, ADI-10086 and ADI-10087 are variants of the CDR-H1 and CDR-H2 regions of ADI-09912, ADI-10088, ADI-10089 and ADI-10090 are variants of VH region ADI-09113. See Table B-D for relevant sequence information for the antibodies. The affinity of these antibodies for human PCSK9 was increased by 10-fold, and the $K_D$ range was from 4-17 pM to 200 pM, as measured by ForteBio method and MSD-SET assay (Table 1, Table 2). Some antibodies have an affinity about 10 times higher than that of the control antibody. The number of antibodies may be further limited by identifying other functions of an antibody for preclinical development.

The sequence information and numbering of each anti-PCSK-9 antibody referred to in the present application are shown in Tables B-D below:

TABLE B

CDR Sequence Numbers for Each Exemplary Antibody of the Present Application

| IgG ADI name | Heavy chain CDR SEQ ID NO | | | Light chain CDR SEQ ID NO | | |
|---|---|---|---|---|---|---|
| | CDR1 | CDR2 | CDR3 | CDR1 | CDR2 | CDR3 |
| ADI-02396 | 1 | 2 | 3 | 4 | 5 | 6 |
| ADI-09111 | 1 | 2 | 18 | 4 | 5 | 6 |
| ADI-09112 | 1 | 14 | 19 | 4 | 5 | 6 |
| ADI-09113 | 7 | 15 | 18 | 4 | 5 | 6 |
| ADI-10085 | 8 | 16 | 19 | 4 | 5 | 6 |
| ADI-10086 | 9 | 17 | 19 | 4 | 5 | 6 |
| ADI-10087 | 10 | 17 | 19 | 4 | 5 | 6 |
| ADI-10088 | 11 | 17 | 18 | 4 | 5 | 6 |
| ADI-10089 | 12 | 17 | 18 | 4 | 5 | 6 |
| ADI-10090 | 13 | 17 | 18 | 4 | 5 | 6 |

TABLE C

Framework Region Sequence Numbers of Heavy Chain Variable Region and Light Chain Variable Region of Each Exemplary Antibody of the Present Application

| IgG ADI name | Framework Region of Heavy Chain Variable Region SEQ ID NO | | | | Framework Region of Light Chain Variable Region SEQ ID NO | | | |
|---|---|---|---|---|---|---|---|---|
| | FR1 | FR2 | FR3 | FR4 | FR1 | FR2 | FR3 | FR4 |
| ADI-02396 | 45 | 46 | 47 | 48 | 49 | 50 | 51 | 52 |
| ADI-09111 | 45 | 46 | 47 | 48 | 49 | 50 | 51 | 52 |
| ADI-09112 | 45 | 46 | 47 | 48 | 49 | 50 | 51 | 52 |

TABLE C-continued

Framework Region Sequence Numbers of Heavy Chain Variable Region and Light Chain Variable Region of Each Exemplary Antibody of the Present Application

| IgG ADI name | Framework Region of Heavy Chain Variable Region SEQ ID NO | | | | Framework Region of Light Chain Variable Region SEQ ID NO | | | |
|---|---|---|---|---|---|---|---|---|
| | FR1 | FR2 | FR3 | FR4 | FR1 | FR2 | FR3 | FR4 |
| ADI-09113 | 45 | 46 | 47 | 48 | 49 | 50 | 51 | 52 |
| ADI-10085 | 45 | 46 | 47 | 48 | 49 | 50 | 51 | 52 |
| ADI-10086 | 45 | 46 | 47 | 48 | 49 | 50 | 51 | 52 |
| ADI-10087 | 45 | 46 | 47 | 48 | 49 | 50 | 51 | 52 |
| ADI-10088 | 45 | 46 | 47 | 48 | 49 | 50 | 51 | 52 |
| ADI-10089 | 45 | 46 | 47 | 48 | 49 | 50 | 51 | 52 |
| ADI-10090 | 45 | 46 | 47 | 48 | 49 | 50 | 51 | 52 |

TABLE D

Sequence Numbers of Heavy Chain Variable Region, Light Chain Variable Region, Heavy Chain and Light Chain of Each Exemplary Antibody of the Present Application

| IgG ADI name | Heavy Chain Variable Region SEQ ID NO | Heavy Chain SEQ ID NO | Light Chain Variable Region SEQ ID NO | Light Chain SEQ ID NO |
|---|---|---|---|---|
| ADI-02396 | 23 | 34 | 24 | 35 |
| ADI-09111 | 25 | 36 | 24 | 35 |
| ADI-09112 | 26 | 37 | 24 | 35 |
| ADI-09113 | 27 | 38 | 24 | 35 |
| ADI-10085 | 28 | 39 | 24 | 35 |
| ADI-10086 | 29 | 40 | 24 | 35 |
| ADI-10087 | 30 | 41 | 24 | 35 |
| ADI-10088 | 31 | 42 | 24 | 35 |
| ADI-10089 | 32 | 43 | 24 | 35 |
| ADI-10090 | 33 | 44 | 24 | 35 |

TABLE 1

$K_D$ Values for Each Antibody as Measured by ForteBio Method

| | Fortebio: IgG KD (M), IgG was immobilized on probes | | |
|---|---|---|---|
| Sample ID | Human PCSK-9 | cynomolgus PCSK-9 | murine PCSK-9 |
| ADI-02396 | 9.50E-09 | 3.23E-08 | 7.83E-08 |
| ADI-09111 | 1.17E-09 | 2.61E-09 | 1.05E-08 |
| ADI-09112 | 4.97E-10 | 9.83E-10 | 3.78E-09 |
| ADI-09113 | 8.04E-10 | 1.12E-09 | 3.10E-09 |
| ADI-10085 | 2.95E-10 | 3.77E-10 | 5.44E-10 |
| ADI-10086 | 3.36E-10 | 4.57E-10 | 6.07E-10 |
| ADI-10087 | 2.96E-10 | 3.96E-10 | 5.58E-10 |
| ADI-10088 | 4.71E-10 | 6.32E-10 | 8.55E-10 |
| ADI-10089 | 3.11E-10 | 4.08E-10 | 5.89E-10 |
| ADI-10090 | 3.52E-10 | 4.69E-10 | 6.74E-10 |
| Alirocumab | 3.01E-11 | 3.83E-10 | 2.66E-09 |
| Evolocumab | 1.03E-09 | 1.30E-09 | 1.14E-07 |
| Bocozumab | 3.86E-10 | 4.76E-10 | 6.63E-10 |
| Lodelcizumab | 1.51E-09 | 2.34E-09 | NB |

TABLE 2

$K_D$ Values for Each Antibody as Measured by MSD-SET Dynamics

| | MSD: Fab $K_D$ (M), IgG was immobilized on plates to be tested | | | |
|---|---|---|---|---|
| sample ID | human PCSK-9 (PH 7.4) | human PCSK-9 (PH 6.0) | cynomolgus PCSK-9 (PH 7.4) | murine PCSK-9 (PH 7.4) |
| ADI-02396 | ND | ND | 5.90E-09 | ND |
| ADI-09111 | 7.00E-10 | 1.90E-9 | 1.20E-09 | 3.50E-09 |
| ADI-09112 | 2.20E-10 | 4.90E-10 | 3.00E-10 | 1.20E-09 |
| ADI-09113 | 1.70E-10 | 6.50E-10 | 2.40E-10 | 7.60E-10 |
| ADI-10085 | 4.20E-12 | 5.90E-12 | 1.20E-11 | 4.10E-11 |
| ADI-10086 | 8.60E-12 | 1.30E-11 | 2.40E-11 | 6.00E-11 |
| ADI-10087 | 5.00E-12 | 9.80E-12 | 1.30E-11 | 4.10E-11 |
| ADI-10088 | 1.00E-11 | 1.60E-11 | 2.20E-11 | 8.70E-11 |
| ADI-10089 | 1.10E-11 | 1.00E-11 | 2.20E-11 | 7.00E-11 |
| ADI-10090 | 1.70E-11 | 2.10E-11 | 3.80E-11 | 1.20E-10 |
| Alirocumab | 7.20E-11 | 5.10E-11 | 8.20E-11 | 3.00E-10 |
| Evolocumab | 1.60E-11 | ND | 8.20E-12 | ND |
| Bocociumab | 2.10E-11 | 3.80E-11 | 2.60E-11 | 6.50E-11 |
| Lodelcizumab | ND | ND | 1.00E-10 | NB |

Example 3 Assay in which the Anti-PCSK-9 Antibody Inhibits the Binding of PCSK-9 to LDLR The PCSK9 protein as described in Example 1 was diluted with PBS solution (phosphate buffer solution) to 400 nmol/L and used as working solution. The anti-PCSK9 antibodies (ADI-10085, ADI-10086, ADI-10087, ADI-10088, ADI-10089 and ADI-10090) obtained in Example 2 were diluted with PBS solution to concentrations of 1000 nmol/L, 100 nmol/L, 10 nmol/L, 1 nmol/L and 0.1 nmol/L, respectively. Solutions of various concentrations of control antibody (Alirocumab, Evolocumab, Bococisumab and Lodelcizumab) were prepared in the same way. The PCSK9 working solution was mixed with equal volume of each gradient-diluted anti-PCSK9 antibody sample or control sample. CHO cells over-expressing LDLR (CHO-LDLR) were re-suspended in PBS solution and counted, the cell concentration was adjusted to $4 \times 10^6$ cells/ml with PBS solution, seeded in a 96-well U-shaped cell culture plate with $2.0 \times 10^5$ cells per well, 50 μl of cell culture medium was added into each well, 50 μl of the mixture of PCSK9 and anti-PCSK9 antibody was added, centrifuged at 200 g for 5 minutes at room temperature, and the supernatant was discarded. Anti-His-FITC (R&D Systems) was diluted at the ratio of 1:200 with PBS solution to the final concentration of 2.5 μg/ml, and then added into a 96-well plate, 100 μl per well, and incubated in ice bath for 30 minutes. Centrifuged at 200 g for 5 minutes at room temperature, the supernatant was gently discard, 150 μl of PBS solution was added to each well, centrifuged at 200 g for 5 minutes at room temperature, and the supernatant was gently discard, the procedure was repeated for 3 times. 80 μl/well PBS solution was added into each well, and the cells were re-suspended by pipetting several times. Fluorescence signal values of the cells were measured by Flow Cytometry.

Fluorescent signal detected in the experiment was shown in Table 3 below.

TABLE 3

| | Fluorescence Signal Values | | | | |
|---|---|---|---|---|---|
| Sample Name | 1000 nM | 100 nM | 10 nM | 1 nM | 0.1 nM |
| ADI-10085 | 5700.0 | 5087.0 | 5684.0 | 8914.0 | 10431.0 |
| ADI-10086 | 5269.0 | 5129.0 | 5830.0 | 6919.0 | 6600.0 |

TABLE 3-continued

Fluorescence Signal Values

| Sample Name | 1000 nM | 100 nM | 10 nM | 1 nM | 0.1 nM |
|---|---|---|---|---|---|
| ADI-10087 | 5094.0 | 5259.0 | 5743.0 | 6483.5 | 6865.0 |
| ADI-10088 | 5216.0 | 5162.0 | 5826.0 | 6827.0 | 6798.0 |
| ADI-10089 | 5331.0 | 5137.0 | 5635.0 | 6500.0 | 6889.5 |
| ADI-10090 | 4822.0 | 4806.0 | 5807.0 | 6750.0 | 6807.0 |
| ADI-02396 | 5993.0 | 5067.0 | 5513.0 | 6375.0 | 6646.0 |
| IgG | 8919.0 | 7523.0 | 6955.0 | 6728.5 | 6998.5 |
| Alirocumab | 4926.0 | 4952.0 | 5748.0 | 6985.0 | 7174.5 |
| Evolocumab | 4805.0 | 5097.0 | 5780.0 | 6807.0 | 6986.0 |
| Bococizumab | 6038.0 | 5307.0 | 6267.5 | 6959.0 | 7096.0 |
| Lodelcizumab | 7330.0 | 8756.0 | 7330.5 | 8756.0 | 8405.0 |
| +PCSK9 | 9977.0 | N/A | N/A | N/A | N/A |
| −PSCK9 | 3985.0 | N/A | N/A | N/A | N/A |
| Blank control | 3782.0 | N/A | N/A | N/A | N/A |

The raw data of Table 3 was analyzed with GraphPad Prism 6 software and FIG. 1 was obtained.

The experimental results show that the anti-PCSK9 antibodies have comparable ability to block the binding of PCSK9 to LDLR relative to the control antibody.

Example 4 Cellular LDL-c Uptake Assay

Cryopreserved HepG2 cells in tubes were taken out from the liquid nitrogen storage tank, thawed rapidly at 37° C. water bath. The cell suspension was transferred into a 15 ml centrifuge tube, added slowly with 4 ml of growth medium (90% DMEM+10% FBS, wherein both DMEM and FBS were purchased from Gibco) at room temperature, centrifuged at 1000 r/min for 5 minutes at room temperature, and then the cell pellet was re-suspended in fresh growth medium and transferred to a culture flask and cultured at 37° C. under 5% $CO_2$. HepG2 cells at logarithmic growth phase were washed twice with PBS solution, added with 1 ml of 0.25% trypsin (purchased from Gibco) and digested for 3 minutes, and 6 ml of growth medium was added to re-suspend the cells and to terminate the reaction. HepG2 cells were adjusted to $0.8 \times 10^6$ cells/ml with growth medium and inoculated into a poly-D-lysine coated 96-well cell culture plate with a black transparent bottom (purchased from Nunc), 100 μL per well, and incubated in an incubator at 37° C., at 5% $CO_2$ for 6-7 hours. The growth medium was discarded and replaced by with assay medium (DMEM+5% FBS), 100 μL/well, and incubated in an incubator at 37° C., at 5% $CO_2$ overnight. Antibody samples (ADI-10085, ADI-10087, ADI-10088, ADI-10089) were diluted to 66.7 nmol/L with assay medium, respectively. And then 4-fold gradient dilution was performed by using the 66.7 nmol/L of samples as the starting concentrations. The positive control antibodies (Alirocumab, Evolocumab, and Lodelcizumab) and the negative controls (LDL, PCSK9+LDL, and IgG) were subjected to the same operation. 60 μl of the obtained sample at each concentration gradient was separately mixed with equal volume of 60 μl of 66.7 nmol/L of PCSK9 to obtain each mixture. 120 μl of assay medium was used as blank control. The liquid in a 96-well plate was aspirated and discarded, 50 μl of the above mixture and blank control sample was separately added to each well, and incubated in an incubator at 37° C. at 5% $CO_2$ for 1 hour. The plate was taken out, 50 μl of LDL solution labeled with 6 μg/ml BODIPY (purchased from life technologies) diluted with assay medium was added into each well, and the plate was incubated at 37° C. at 5% $CO_2$ for 4 hours. The medium was discarded, and the plate was washed with 100 μl of PBS solution per well. The PBS solution was discarded after washing twice and then 100 μl PBS solution was added into each well again. Fluorescence values were read using Spectra Max 13 plate reader.

The raw data obtained for fluorescence values are listed in Table 4 below, and the data disclosed in Table 4 was analyzed and plotted with GraphPad Prism 6 software and FIG. 2 was obtained. From the experimental results, it was found that the anti-PCSK9 antibodies (ADI-10085, ADI-10087, ADI-10088, ADI-10089) enhanced the fluorescence value by about two times in the case of HepG2 cells compared to the fluorescence values in absence of anti-PCSK9 antibody. These data demonstrate that each of the anti-PCSK9 antibodies disclosed in the present application can increase the capability of HepG2 cells to restore LDLR and inhibit the decrease in LDK-c uptake induced by PCSK9, thereby increase the uptake of LDL-c by HepG2 cells. In addition, the effects of the antibodies at 16.8 nM and 66.7 nM are both superior to those of the positive control antibodies.

TABLE 4

Fluorescence Signal Values

| Sample Name | 4.2 nM | | 16.8 nM | | 66.7 nM | |
|---|---|---|---|---|---|---|
| Blank Control | 0.1179 | 0.1174 | N/A | N/A | N/A | N/A |
| LDL | 0.7139 | 0.6903 | N/A | N/A | N/A | N/A |
| PCSK9 + LDL | 0.3251 | 0.3259 | N/A | N/A | N/A | N/A |
| IgG | 0.3583 | 0.3250 | 0.2973 | 0.3093 | 0.3288 | 0.2881 |
| ADI-02396 | 0.3662 | 0.3522 | 0.4035 | 0.3410 | 0.4319 | 0.4006 |
| ADI-10085 | 0.4228 | 0.4349 | 0.7800 | 0.7423 | 0.7492 | 0.7973 |
| ADI-10087 | 0.3701 | 0.4030 | 0.7198 | 0.6835 | 0.7576 | 0.7755 |
| ADI-10088 | 0.3570 | 0.4005 | 0.5736 | 0.5611 | 0.7059 | 0.7522 |
| ADI-10089 | 0.3803 | 0.3986 | 0.7116 | 0.7064 | 0.7742 | 0.7413 |
| Alirocumab | 0.3636 | 0.3704 | 0.3958 | 0.3919 | 0.6865 | 0.7158 |
| Evolocumab | 0.3506 | 0.3598 | 0.3555 | 0.3630 | 0.7239 | 0.7785 |
| Lodelcizumab | 0.3181 | 0.3523 | 0.3173 | 0.3141 | 0.3296 | 0.3124 |

Example 5 Analysis of Cellular Internalization of LDLR

PCSK9 can directly bind to LDLR to promote LDLR internalization. After entering into hepatocytes, LDLR is transported to lysosome to be degraded, thereby the LDLR expressed on the cell surface is reduced and the serum level of LDL-c is increased. Anti-PCSK9 antibodies block the binding of PCSK9 to LDLR, thereby reduce the ability of PCSK9 to consume LDLR. In this experiment, CHO-LDLR cells were incubated with an anti-PCSK9 antibody and PCSK9 protein solution, and the fluorescence value of LDLR was detected by flow cytometry above. The fluorescence value of an anti-PCSK9 antibody was compared to that of the positive control antibody (Evolocumab) to determine the biological activity of the anti-PCSK9 antibody on cellular internalization of LDLR.

The above PCSK9 protein was prepared with RPMI 1640 cell culture medium (Gibco) to a concentration of 50 μg/ml. 60 μl of 1000 nm anti-PCSK9 antibody (ADI-10085 and ADI-10087) was mixed with PCSK9 (50 μg/ml) solution homogeneously and incubated for 30 min. The positive antibody controls were subjected to the same treatment. CHO cells and CHO-LDLR cells were centrifuged at 500 g for 3 minutes at room temperature, respectively, re-suspended in PBS solution and adjusted to a cell density of $2 \times 10^6$ cells/ml, and added into a 96-well U-shaped plate, 100 μl/well. The above mixed sample was added to the culture plate in quadruplicate, 100 μl/well, pipetted homogeneously, and incubated at 4° C. for 4 hours. Thereafter, the samples were washed three times with 200 μl of PBS solution, and centrifuged at 500 g for 3 minutes at room temperature. 5 μl of anti-LDLR-PE (Beijing Yiqiao Company, Cat No. 20131-R301-P) was diluted with 100 μl of PBS solution, and then added to a 96-well U-shaped plate at 100 μl per well and incubated for 30 minutes in dark place. The cells were washed three times with 200 μl of PBS solution, centrifuged at 500 g for 3 minutes, and re-suspended in cell culture medium. The fluorescence signal of PE fluorescence-labeled LDLR protein on the surface of CHO-LDLR cells was detected by Flow Cytometry. The experimental results are shown in Table 5. The raw data of Table 5 were analyzed with GraphPad Prism 6 software and FIG. 3 was obtained.

As can be seen from the results of Table 5, the antibodies obtained in the present application effectively prevent LDLR from cellular internalization.

TABLE 5

Fluorescence Signal Values

| Sample Name | 1 | 2 | 3 | 4 | average value |
|---|---|---|---|---|---|
| CHO control | 26308.5 | 14666.5 | N/A | N/A | 20487.5 |
| untreated | 1461967 | 1413043 | N/A | N/A | 1437505 |
| +PCSK9 | 267181 | 284270.5 | 353893 | 362791 | 317033.9 |
| ADI-10085 | 1148583 | 1232906 | 1465201 | 1339541 | 1296558 |
| ADI-10087 | 1432592 | 1332187 | 1339160 | 1300079 | 1351005 |
| Evolocumab | 1560702 | 1524849 | 1507073 | 1500379 | 1523251 |

Example 6: Epitope Recognized by Anti-PCSK Antibodies of the Invention

Prior to characterization, the integrity and aggregation level of the anti-PCSK antibody of the invention (ADI-10087 was used in this example, the same was also used below) and human PCSK-9 as an antigen were detected separately by using Ultrafelx III MALDI ToF ToF Mass Spectrometer (Bruker) equipped with a CovalX's HM4 interaction module (CovalX AG, Zurich, Switzerland) (experimental methods and result analysis are shown in Section A below). No non-covalent polymerization between the anti-PCSK antibody and human PCSK9 were detected. Human PCSK9 (hereinafter referred to as PCSK9-WT) is formed by non-covalent binding of two subunits of 59.983 kDa (hereinafter referred to as PCSK9-WT Reduced) and 13.749 kDa.

A. Characterization of Antibody/Antigen Complexes

1. Materials and Methods 1.1 Instruments

To characterize the complex, the molecular weight was measured using Ultraflex III MALDI ToF ToF Mass Spectrometer (Bruker) equipped with a CovalX HM4 interaction module.

CovalX interaction module includes a dedicated detection system, which is designed to optimize the detection for molecular weight up to 2 MDa and has sensitivity at nanomolar grade.

1.2 Sample Preparation:

Control Experiment

Antibody/antigen complexes were prepared at the following concentrations:

| | antigen: PCSK9-WT | | antibody: anti-PCSK9 antibody | | antibody/ antigen complex | |
|---|---|---|---|---|---|---|
| Mixture | volume | concentration | volume | concentration | volume | concentration |
| 1 | 5 μl | 8 μM | 5 μl | 1 μM | 10 μl | 0.5 μM/4 μM |

1 μl of the obtained antibody/antigen mixture was mixed with 1 μl of sinapic acid matrice-supersaturated solution (10 mg/ml, acetonitrile/water (1:1, v/v), TFA 0.1%, provided by K200 MALDI Kit), and from which 1 μl was spotted on a MALDI plate (SCOUT 384, AchorChip). After crystallization at room temperature, the plates were introduced into MALDI ToF Mass Spectrometer and analyzed immediately. The analysis has been repeated in triplicate.

Cross-Linking Experiment

The mixture prepared for the control experiment (9 μl left) was submitted to cross-linking using CovalX's K200 MALDI MS analysis kit. 9 μl of the antibody/antigen mixture is mixed with 1 μl of K200 Stabilizer reagent (2 mg/ml, CovalX AG, Zurich, Switzerland) and incubated at room temperature for 180 minutes. Thereafter, the samples were prepared for MALDI analysis as for Control experiments.

1.3 High-Mass MALDI MS Analysis

MALDI ToF MS analysis was performed using CovalX HM4 interaction module, which was equipped with a standard nitrogen laser ion source and can be focused on different mass ranges from 0 to 2000 kDa.

The parameters used are as follows:

Mass Spectrometer:

Linear and Positive Ion Mode

Ion source 1: 20 kV

Ion source 2: 17 kV

Lens: 12 kV

Pulsed ion extraction: 400 ns

HM4:

Gain voltage: 3.14 kV

Acceleration voltage: 20 kV

The mass spectrometer was subjected to external mass calibration with a clusters of proteins containing Insulin, BSA and IgG prior to use. For each sample, 3 points were analyzed (300 laser shots per spot). The spectrogram presented corresponds to the sum of 300 laser shots. MS data were analyzed by using CovalX Complex Tracker Analysis Software version 2.0.

2. Results 2.1 Anti-PCSK9 Antibody/PCSK9-WT 2.1.1 Interaction Analysis

Control Experiment

In the control experiment, both antigen PCSK9-WT Reduced and anti-PCSK9 antibody were detected, and the detected molecular weight was MH+=59.716 kDa and MH+=146.769 kDa, respectively (FIG. 6, control).

| Observed molecular weight (kDa) | |
|---|---|
| 59.716 | PCSK9-WT Reduced |
| 146.769 | Anti-PCSK9 antibody |

Cross-Linking Experiment

In the cross-linking experiment, the antibody/antigen complex was incubated with the cross-linking agent K200 for 180 minutes and the molecular weight was measured with MALDI ToF. After cross-linking, in addition to the two peaks detected in the control experiment, four additional peaks were detected: MH+=214.902 kDa, MH+=229.111 kDa, MH+=276.105 kDa and MH+=290.815 kDa (FIG. 6, cross-linking).

Using the Complex Tracker software, we overlapped the control and cross-linking spectrogram and resolved four non-covalent complexes with the following compositions (FIG. 6, overlay):

| Observed molecular weight(kDa) | Compositions of the complex |
| --- | --- |
| 206.341 | [anti-PCSK9 antibody•PCSK9-WT Reduced] |
| 219.984 | [anti-PCSK9 antibody•PCSK9-WT] |
| 265.107 | [anti-PCSK9 antibody•2 PCSK9-WT Reduced] |
| 279.230 | [anti-PCSK9 antibody•PCSK9-WT Reduced•PCSK9-WT] |

3. Conclusion of Antibody/Antigen Complex Characterization

Characterization of the antibody/antigen complex revealed that both the antigen PCSK9-WT Reduced and PCSK9-WT can bind to the anti-PCSK9 antibody.

B. Characterization of the Molecular Interface of the Antibody/Antigen Complex (Molecular Interface)

For high-resolution determination of the binding epitope between the anti-PCSK9 antibody and the antigen PCSK9-WT, the antibody/antigen complex was incubated with the cross-linking agent DSS d0/d12, followed by enzymatic hydrolysis with trypsin, chymotrypsin, aspartate N-terminal endonuclease (Asp-N), elastase and thermolysin, respectively, and the cross-linked peptide fragments obtained after enzymatic hydrolysis were identified by an online system of nano-liquid phase chromatography connected in series with high resolution mass spectrometry (nLC-LTQ-Orbitrap MS/MS) and analyzed with XQuest and Stavrox software.

Figure 7:
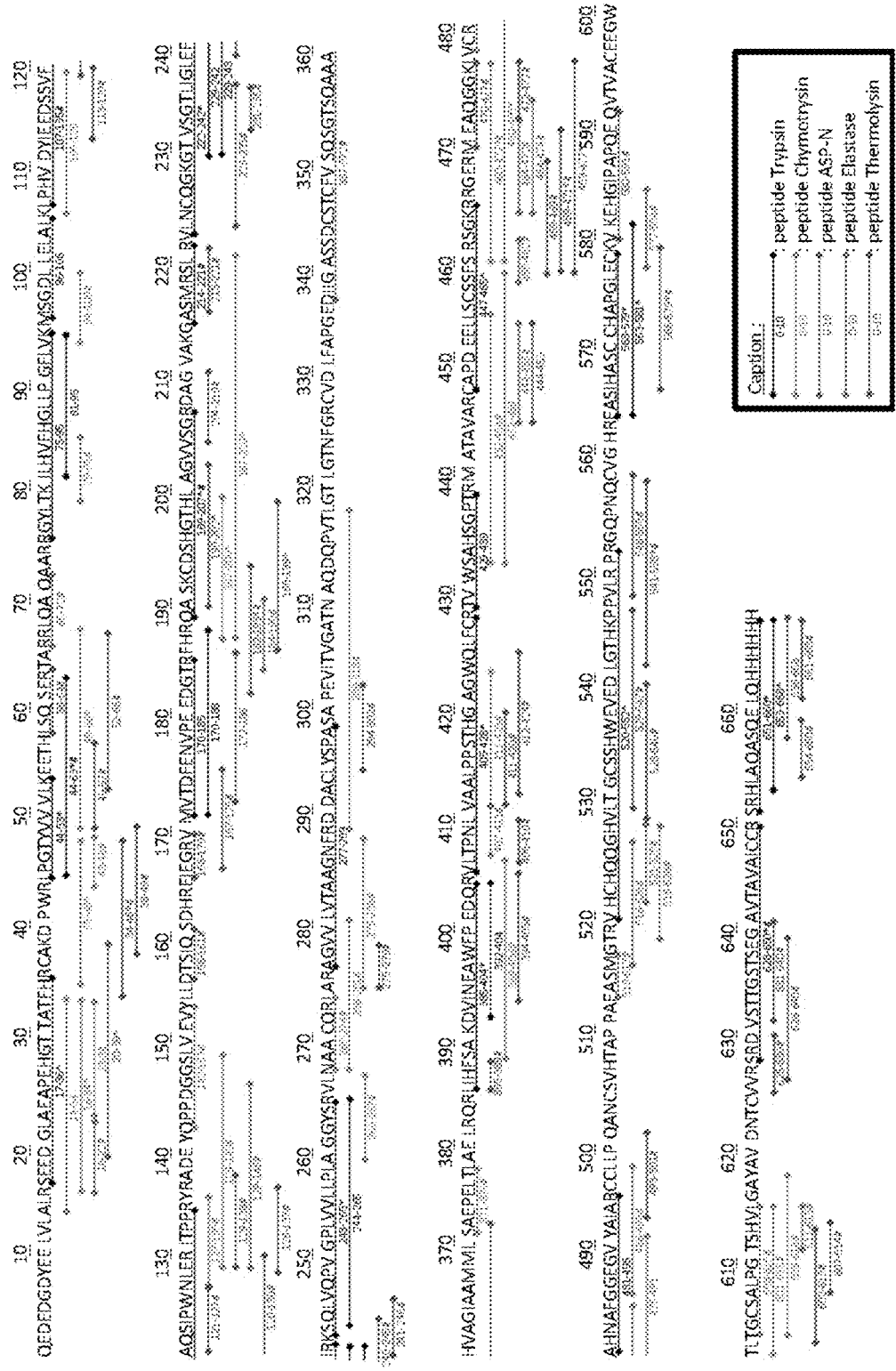
FIG. 7 shows trypsin, chymotrypsin, Asp-N, elastase and thermolysin peptide of PCSK9-WT. 88.77% of the sequences were covered by the identified peptides.

For the antigen PCSK9-WT alone (without anti-PCSK9 antibody), analysis of cross-linking and sequence characterization was performed (experimental steps were the same as the cross-linking and analysis for the antibody/antigen complexes listed below). Based on the results of endonuclease enzymatic hydrolysis and mass spectrometry analysis, the identified sequence coverage of PCSK9-WT was 88.77%. The amino acid sequence (SEQ ID NO: 54) and the peptides identified by different protein endonuclease enzymatic hydrolysis are shown in FIG. 7. The experimental results of these peptides and antibody/antigen complexes were integrated and analyzed to improve the accuracy of epitope identification.

1. Materials and Methods

1.1 Instruments

Ultimate 3000 (Dionex) nano-liquid phase chromatography system is connected in series with LTQ-Orbitrap XL mass spectrometer (Thermo Scientific).

1.2 Sample Preparation:

Antibody/Antigen Complex

To obtain an antibody/antigen mixture with a final concentration of 0.5 µM/4 µM, 5 µl of the antibody (concentration of 1 µM) was mixed with 5 µl of the antigen sample (concentration of 8 µM). The mixture was incubated at 37° C. for 180 minutes.

| mix | PCSK9-WT | | Anti-PCSK9 antibody | | Anti-PCSK9 antibody/ PCSK9-WT mixture | |
| --- | --- | --- | --- | --- | --- | --- |
| | volume | concentration | volume | concentration | volume | concentration |
| 1 | 5 µl | 8 µM | 5 µl | 1 µM | 10 µl | 0.5 µM/4 µM |

Cross-Linking Reaction 1 mg DSS (d0) cross-linking agent (Thermo Scientific) was mixed with 1 mg deuterated DSS (d12) cross-linking agent (CovalX AG), added with 1 ml of DMF to obtain 2 mg/ml DSS d0/d12 solution. 10 µl of the previously prepared antibody/antigen mixture was mixed with 1 µl of the prepared cross-linking agent DSS d0/d12 solution (2 mg/ml), and incubated at room temperature for 180 minutes for crosslinking.

Reduction/Alkylation

10 µl of the previously prepared cross-linked antibody/antigen complex was mixed with 40 µl of ammonium bicarbonate (25 mM, pH 8.3), added with 2 µl of DTT (500 mM), and incubated at 55° C. for 1 hour. After the incubation, 2 µl of iodoacetamide (1 M) was added and incubated at room temperature for 1 hour in dark room. After the incubation, 120 µl of proteolytic buffer (available from each endonuclease product) was added.

Trypsin Proteolysis

145 µl of the reduced/alkylated cross-linked antibody/antigen complex was mixed with 0.70 µl of Trypsin (Roche Diagnostic) at a ratio of 100:1 (protein: enzyme, w/w) and incubated overnight at 37° C.

Chymotrypsin Proteolysis

145 µl of the reduced/alkylated cross-linked antibody/antigen complex was mixed with 0.35 µl of Chymotrypsin (Roche Diagnostic) at a ratio of 200:1 (protein: enzyme, w/w) and incubated overnight at 25° C.

Asp-N Proteolysis

145 µl of the reduced/alkylated cross-linked antibody/antigen complex was mixed with 0.35 µl of Asp-N(Roche Diagnostic) at a ratio of 200:1 (protein: enzyme, w/w) and incubated overnight at 37° C.

Elastase Proteolysis

145 µl of the reduced/alkylated cross-linked antibody/antigen complex was mixed with 0.70 µl of Elastase (Roche Diagnostic) at a ratio of 100:1 (protein: enzyme, w/w) and incubated overnight at 37° C.

Thermolysin Proteolysis

145 µl of the reduced/alkylated cross-linked antibody/antigen complex was mixed with 1.40 µl of Thermolysin (Roche Diagnostic) at a ratio of 50:1 (protein: enzyme, w/w) and incubated overnight at 70° C.

After proteolysis overnight, the reaction was stopped by the addition of 1% formic acid.

nLC-LTQ-Orbitrap MS/MS Analysis

10 µl of the proteolytic peptide solution was injected into a nano-liquid phase chromatography system (Ultimate 3000, Dionex) connected online in series with TQ-Orbitrap XL (Thermo Scientific) and peptide fragments were identified. The running parameters for liquid chromatography and mass spectrometry are as follows:

| | |
|---|---|
| mobile phase A | 95/05/0.1 water/acetonitrile/formic acid v/v/v |
| mobile phase B | 20/80/0.1 water/acetonitrile/formic acid v/v/v |
| elution gradient | In 35 min, 5-40% B |
| injection volume | 10 μl |
| pre-column | 300 μm ID × 5 mm C4 PepMap ™ |
| pre-column flow rate | 30 μl/min |
| analytical column | 75 μm ID × 5 cm C4 PepMap ™ |
| analytical column flow rate | 200 nl/min |

| | |
|---|---|
| Needle voltage | 1.8 kV |
| Capillary voltage | 5 kV |
| μscan MS | 1 |
| μscan MS2 | 1 |
| MS range m/z | 300-1700 |
| MS/MS strategy | MS + 6 CID MS/MS |
| Min. Signal required | 500 |
| Ion isolation window | 3 m/z units |
| Normamized collision energy | 35% |
| Default charge state | 2 |
| Activation q | 0.25 |
| Activation time | 30 |
| Dynamic exclusion | ON |
| Dynamic exclusion params | RC 1, RD 30 s, ED 30 s |
| Charge state screening | ON |
| Charge state rejection | ON |
| Charge state rejection Params | +1 and Unassigned Rejected |

Data Analysis

Cross-linked peptide fragments were analyzed by using Xquest version 2.0 and Stavrox 2.1 software.

2. Results 2.1.1 Trypsin Proteolysis

A peptide fragment cross-linked between the anti-PCSK9 antibody and the antigen PCSK9 was detected by nLC-LTQ-Orbitrap MS/MS analysis, after the proteolysis of antibody/antigen complex cross-linked by DSS d0/d12 with Trypsin. This cross-linked peptide fragment was detectable with either Xquest or Stavrox software.

| sequence | Protein 1 | Protein 2 | sequence-Protein 1 | sequence-Protein 2 | Identification score | Cross-linking type | Cross-linking site 1 | Cross-linking site 2 | Xquest identification | Stavrox identification |
|---|---|---|---|---|---|---|---|---|---|---|
| NWFTFGGGTK-EETHLSQSER-a4-b3 | Anti-PCSK9 antibody LC(light chain) | PCSK9-WT | 93-102 | 54-63 | 8.35 | inter-protein xl | 96 | 56 | Yes | Yes |

2.1.2 Chymotrypsin Proteolysis

Six peptide fragments cross-linked between the anti-PCSK9 antibody and the antigen PCSK9 were detected by nLC-LTQ-Orbitrap MS/MS analysis, after the proteolysis of antibody/antigen complex cross-linked by DSS d0/d12 with Chymotrypsin. These cross-linked peptide fragments were detectable with either Xquest or Stavrox software.

| sequence | Protein 1 | Protein 2 | sequence-Protein 1 | sequence-Protein 2 | Identification score | Cross-linking type | Cross-linking site 1 | Cross-linking site 2 | Xquest identification | Stavrox identification |
|---|---|---|---|---|---|---|---|---|---|---|
| RGSTYY-VVVLKEETHL-a5-b8 | Anti-PCSK9 antibody HC (heavy chain) | PCSK9-WT | 56-61 | 49-58 | 10.1 | inter-protein xl | 60 | 56 | Yes | Yes |
| RGSTYY-VVVLKEETHL-a5-b9 | Anti-PCSK9 antibody HC | PCSK9-WT | 56-61 | 49-58 | 13.88 | inter-protein xl | 60 | 57 | Yes | Yes |
| CARENSGVVPAAGPNW-RLPGTYVVVL-a6-b6 | Anti-PCSK9 antibody HC | PCSK9-WT | 97-112 | 43-52 | 10.49 | inter-protein xl | 102 | 48 | Yes | Yes |
| SCRASQSVSSY-QAQAARRGYL-a5-b6 | Anti-PCSK9 antibody LC | PCSK9-WT | 22-32 | 69-78 | 13.22 | inter-protein xl | 26 | 74 | Yes | Yes |
| SCRASQSVSSYL-QAQAARRGY-a3-b6 | Anti-PCSK9 antibody LC | PCSK9-WT | 22-33 | 69-77 | 17.31 | inter-protein xl | 24 | 74 | Yes | Yes |
| SCRASQSVSSYL-QAQAARRGY-a7-b6 | Anti-PCSK9 antibody LC | PCSK9-WT | 22-33 | 69-77 | 14.67 | inter-protein xl | 28 | 74 | Yes | Yes |

2.1.3 Asp-N Proteolysis

No peptide fragment cross-linked between the anti-PCSK9 antibody and the antigen PCSK9 were detected by nLC-LTQ-Orbitrap MS/MS analysis, after the proteolysis of the antibody/antigen complex cross-linked by DSS d0/d12 with Asp-N.

2.1.4 Elastase Proteolysis

No peptide fragment cross-linked between the anti-PCSK9 antibody and the antigen PCSK9 were detected by nLC-LTQ-Orbitrap MS/MS analysis, after the proteolysis of the antibody/antigen complex cross-linked by DSS d0/d12 with Elastase.

2.1.5 Thermolysin Proteolysis

No peptide fragment cross-linked between the anti-PCSK9 antibody and the antigen PCSK9 were detected by nLC-LTQ-Orbitrap MS/MS analysis, after the proteolysis of the antibody/antigen complex cross-linked by DSS d0/d12 with Thermolysin.

3. Conclusion

We can characterize the interaction interface between the anti-PCSK9 antibody and the antigen PSCK9 by chemical cross-linking and nLC-LTQ-Orbitrap MS/MS analysis.

Figure 8:
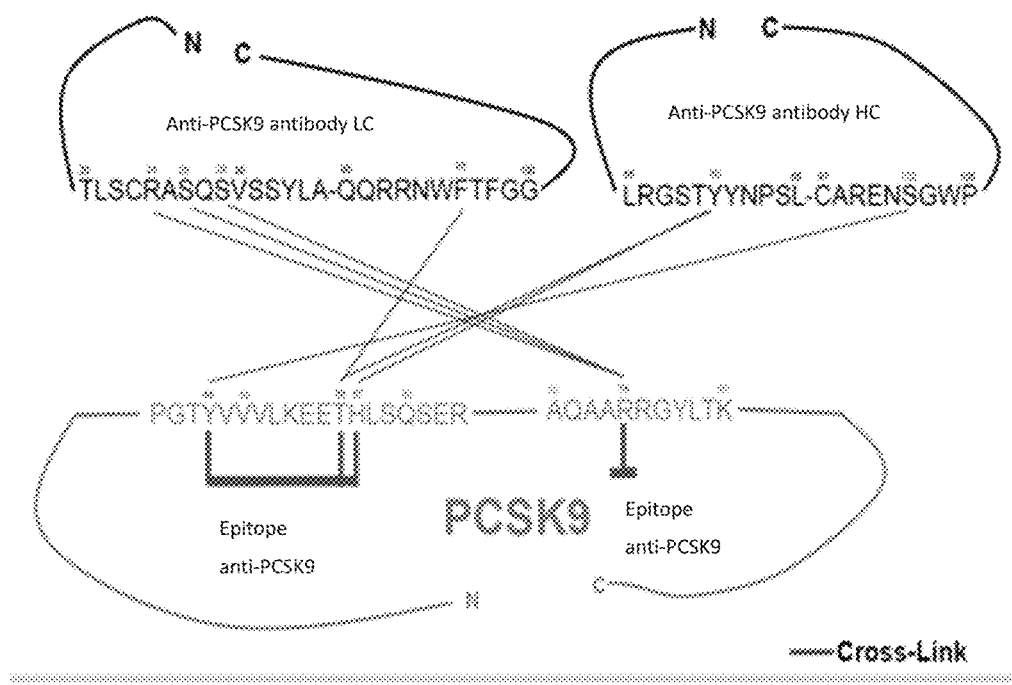
FIG. 8 shows the interaction between PCSK9-WT and anti-PCSK9 antibodies.

Our analysis indicates that the epitope of the monoclonal antibody comprises a region formed by several PSCK9 amino acid sites as follows: position 48 (tyrosine) (corresponding to Y78 of human PCSK9 shown in SEQ ID NO: 53), position 56 (threonine) (corresponding to T86 of human PCSK9 shown in SEQ ID NO: 53), position 57 (histidine) (corresponding to H87 of human PCSK9 shown in SEQ ID NO: 53) and position 74 (arginine) (corresponding to R104 of human PCSK9 shown in SEQ ID NO: 53). The results are shown in FIG. 8.

Sites on the anti-PCSK9 antibody capable of binding to the antigen PSCK9 includes arginine on position 24 (complementarity determining region 1), serine on position 26 (complementarity determining region 1), serine on position 28 (complementarity determining region 1) and phenylalanine on position 96 (complementarity determining region 2) of the antibody light chain, and tyrosine on position 60 (complementarity determining region 2) and serine on position 102 (complementarity determining region 3) of the heavy chain.

Example 7 the Effects of Anti-PCSK9 Antibodies on Lowering the Blood Fat of Healthy SD Rats The antibody (anti-PCSK9 antibody ADI-10087) to be tested was administered to SPF grade SD rats according to a conventional method in the art, wherein the female rats weighed about 254-294 g and were about 9-12 weeks old; the male rats weighed about 369-420 g and were about 9 to 12 weeks old. Each group were administered with a single dose, and the dosage regimen is shown in Table 6.

TABLE 6

| Group No. | Group | Dosage (mg/kg) | concentration (mg/mL) | Dosing capacity (mL/kg) | Number of animals |
|---|---|---|---|---|---|
| 1 | Anti-PCSK9 antibody was subcutaneously administered with a single, low dosage | 3 | 0.75 | 4 | 6, half male and half female |
| 2 | Anti-PCSK9 antibody was subcutaneously administered with a single, medium dosage | 10 | 2.5 | 4 | 6, half male and half female |
| 3 | Anti-PCSK9 antibody was subcutaneously administered with a single, high dosage | 30 | 7.5 | 4 | 6, half male and half female |
| 4 | Anti-PCSK9 antibody was intravenously administered with a single dosage | 10 | 2.5 | 4 | 6, half male and half female |
| 5 | Evolocumab, as a control, was subcutaneously administered with a single dosage | 10 | 2.5 | 4 | 6, half male and half female |

Figure 9:
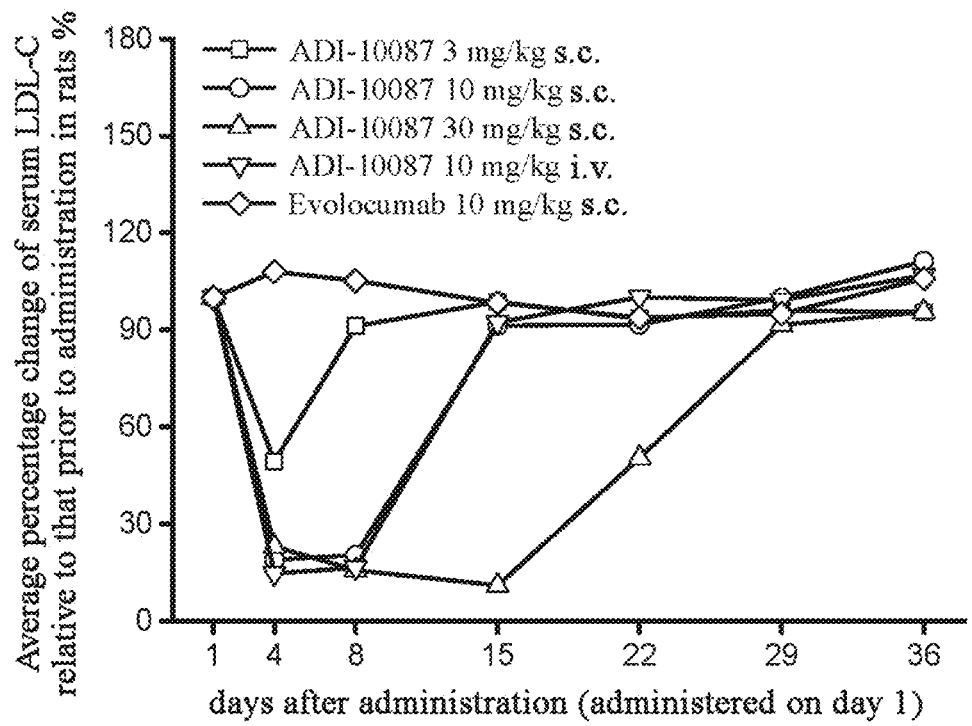
FIG. 9 is a graph plotting the % change rate (average) of the level serum LDL-C relative to that prior to the administration (prior to D1 administration, baseline) versus time, after subcutaneous or intravenous administration of anti-PCSK-9 antibodies or Evolocumab in rats.
Figure 10:
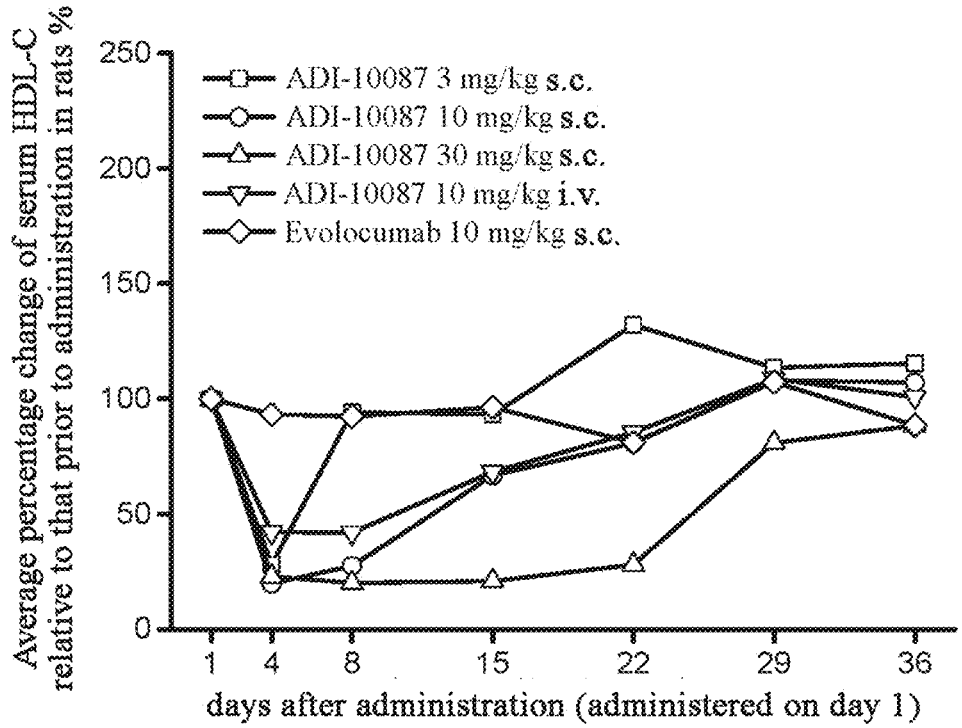
FIG. 10 is a graph plotting the % change rate (average) of the level of serum % HDL-C relative to that prior to the administration (prior to D1 administration, baseline) versus time, after subcutaneous or intravenous administration of anti-PCSK-9 antibodies or Evolocumab in rats.

The animals in each group were subjected to jugular vein blood collection according to a conventional method at the following time points: 0 h before administration (D1), 72 h (D4), 168 h (D8), 336 h (D15), 504 h (D22), 672 h (D29) and 840 h (D36) after administration. Blood was collected into a test tube without anticoagulant, placed on ice for clotting, and then centrifuged at 5000 rpm/min, at 2-8° C. for 10 minutes. The serum was collected and LDL-C and HDL-C were determined with Hitachi-7060 automatic biochemical analyzer. The percentage changes of LDL-C and HDL-C (% LDL-C and % HDL-C) at each time point relative to those before administration (baseline) were calculated according to analysis data of the blood fat. From the experimental results, it was found that the serum levels of LDL-C and HDL-C were dose-dependently decreased after a single subcutaneous administration of 3 to 30 mg/kg anti-PCSK9 antibody of the present invention in rats (FIG. 9 and FIG. 10). For example, there was significant decrease at 3 days, 7 days, 14 days, and 21 days after administration relative to the baseline level. In addition, it was also found that serum levels of LDL-C and HDL-C were not significantly reduced after a single subcutaneous administration of 10 mg/kg Evolocumab in rats.

The above method is also applicable for the other antibodies of the present invention for determination.

Example 8 the Effects of Anti-PCSK9 Antibodies on Lowering the Blood Fat of Healthy Cynomolgus The antibody (anti-PCSK9 antibody ADI-10087) to be tested was administered to cynomolgus according to a conventional method in the art, wherein the female animals weighed about 2-4 kg and were about 3-5 years old; the male animals weighed about 3-5 kg and were about 3-5 years old. The dosage regimen is shown in Table 7, wherein Group 1-5 were administered with a single dosage and Group 6 were administered once a week, totally administered four times.

TABLE 7

| Group No. | Group | Dosage (mg/kg) | concentration (mg/mL) | Dosing capacity (mL/kg) | Number of animals |
|---|---|---|---|---|---|
| 1 | Anti-PCSK9 antibody was subcutaneously administered with a single, low dosage | 1 | 3 | 0.5 | 6, half male and half female |
| 2 | Anti-PCSK9 antibody was subcutaneously administered with a single, medium dosage | 10 | 20 | 0.5 | 6, half male and half female |
| 3 | Anti-PCSK9 antibody was subcutaneously administered with a single, high dosage | 30 | 60 | 0.5 | 6, half male and half female |
| 4 | Anti-PCSK9 antibody was intravenously administered with a single dosage | 10 | 1 | 10 | 6, half male and half female |
| 5 | Evolocumab, as a control, was subcutaneously administered with a single dosage | 10 | 20 | 0.5 | 6, half male and half female |
| 6 | Anti-PCSK9 antibody was subcutaneously administered repeatly | 10 | 20 | 0.5 | 6, half male and half female |

For group 1 to 5, blood was collected from the subcutaneous vein or inguinal femoral artery/inguinal vein of forelimb or hind limb contralateral to the limbs administered with drugs according to a conventional method at the following time points: 0 h before administration and 24 h (D2), 72 h (D4), 120 h (D6), 168 h (D8), 336 h (D15), 504 h (D22), 672 h (D29), 840 h (D36), 1008 h (D43), 1176 h (D50) and 1344 h (D57) after administration. For group 6, blood was collected according to the above method at the following time points: 0 h before the first administration and 24 h (D2), 72 h (D4), 120 h (D6), 168 h (D8, before the second administration), 336 h (D15, before the third administration) after the first administration. And blood was collected 0 h before the last administration, 24 h (D2), 72 h (D4), 120 h (D6), 168 h (D8), 336 h (D15), 504 h (D22), 672 h (D29), 840 h (D36), 1008 h (D43), 1176 h (D50) and 1344 h (D57) after the last administration.

Figure 11:
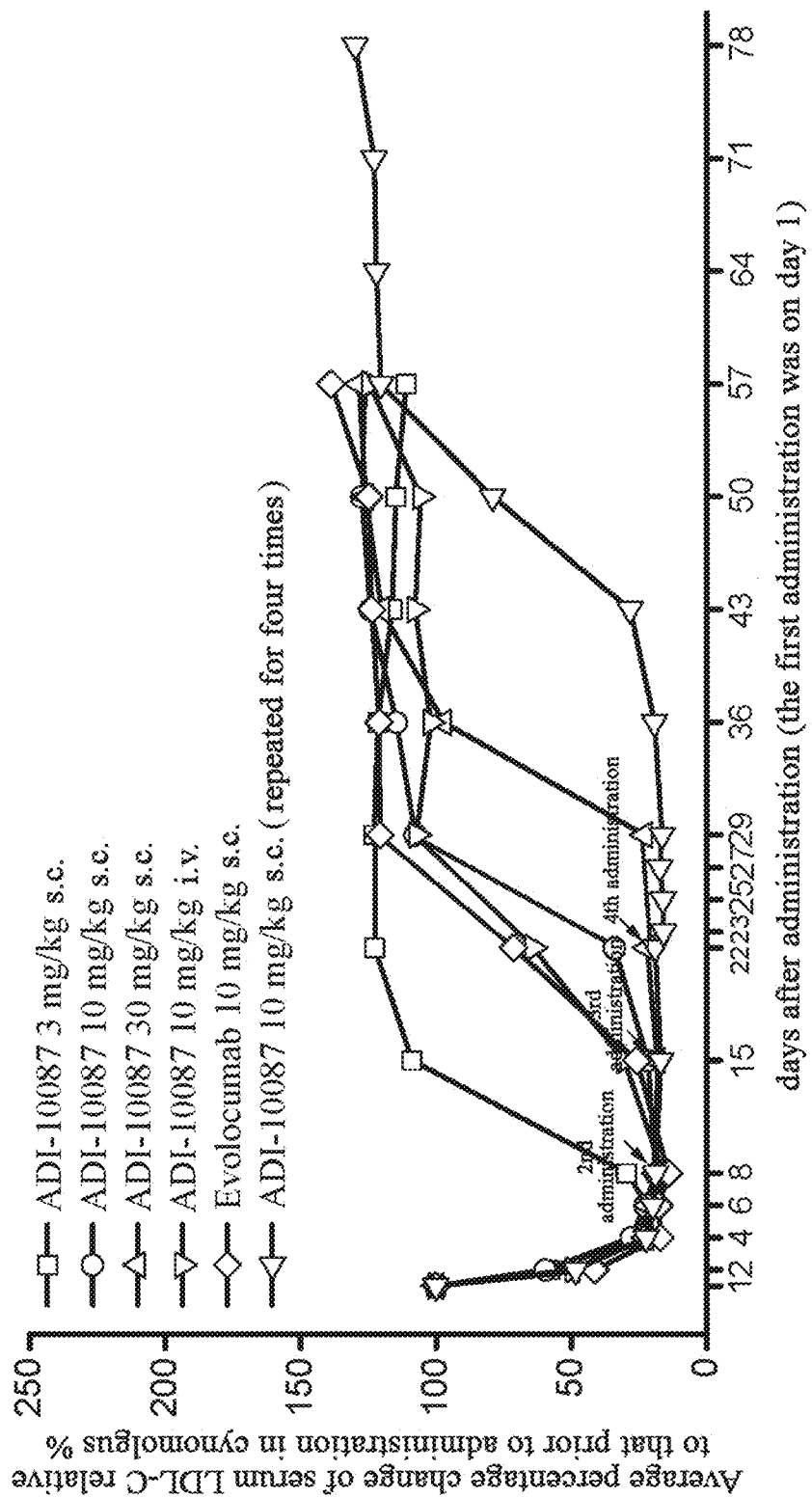
FIG. 11 is a graph plotting the % change rate (average) of the level of serum LDL-C relative to that prior to the administration (prior to D1 administration, baseline) versus time, after administration of anti-PCSK-9 antibodies or Evolocumab to cynomolgus.
Figure 13:
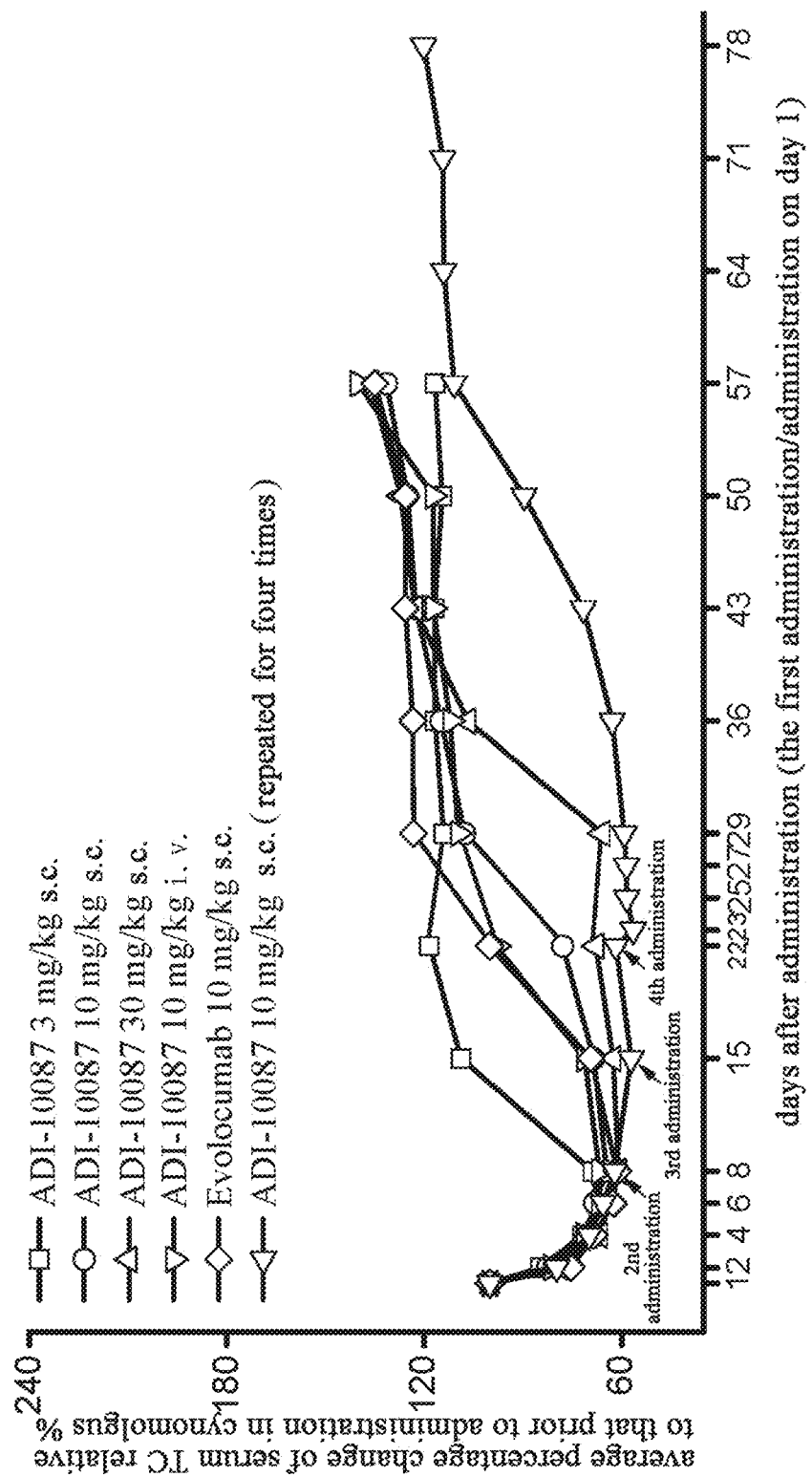
FIG. 13 is a graph plotting the % change rate (average) of the level of serum TC relative to that prior to the administration (prior to D1 administration, baseline) versus time, after administration of anti-PCSK-9 antibodies or Evolocumab to cynomolgus.

The whole blood was collected into a test tube containing coagulant and separation gel, placed on ice for clotting, and then centrifuged at 5000 rpm/min, at 2-8° C. for 10 minutes. After the blood sampling was finished, total cholesterol (TC), LDL-C and HDL-C were determined. The percentage changes of LDL-C and HDL-C (% LDL-C and % HDL-C) at each time point relative to those before administration (baseline) were calculated according to analysis data of the blood fat. From the experimental results, it was found that the serum levels of LDL-C (FIG. 11) and TC (FIG. 13) were significantly decreased after a single subcutaneous administration of 3, 10, 30 mg/kg anti-PCSK9 antibody (ADI-10087) of the present invention to cynomolgus, and a significant dose-effect relationship was observed, and there was a significant decrease at 3 to 28 days after administration relative to the baseline level. It indicates that the antibody disclosed herein can be used to effectively reduce symptoms and/or conditions associated with LDL-C and TC, for example, can be used to lower blood fats.

Figure 12:
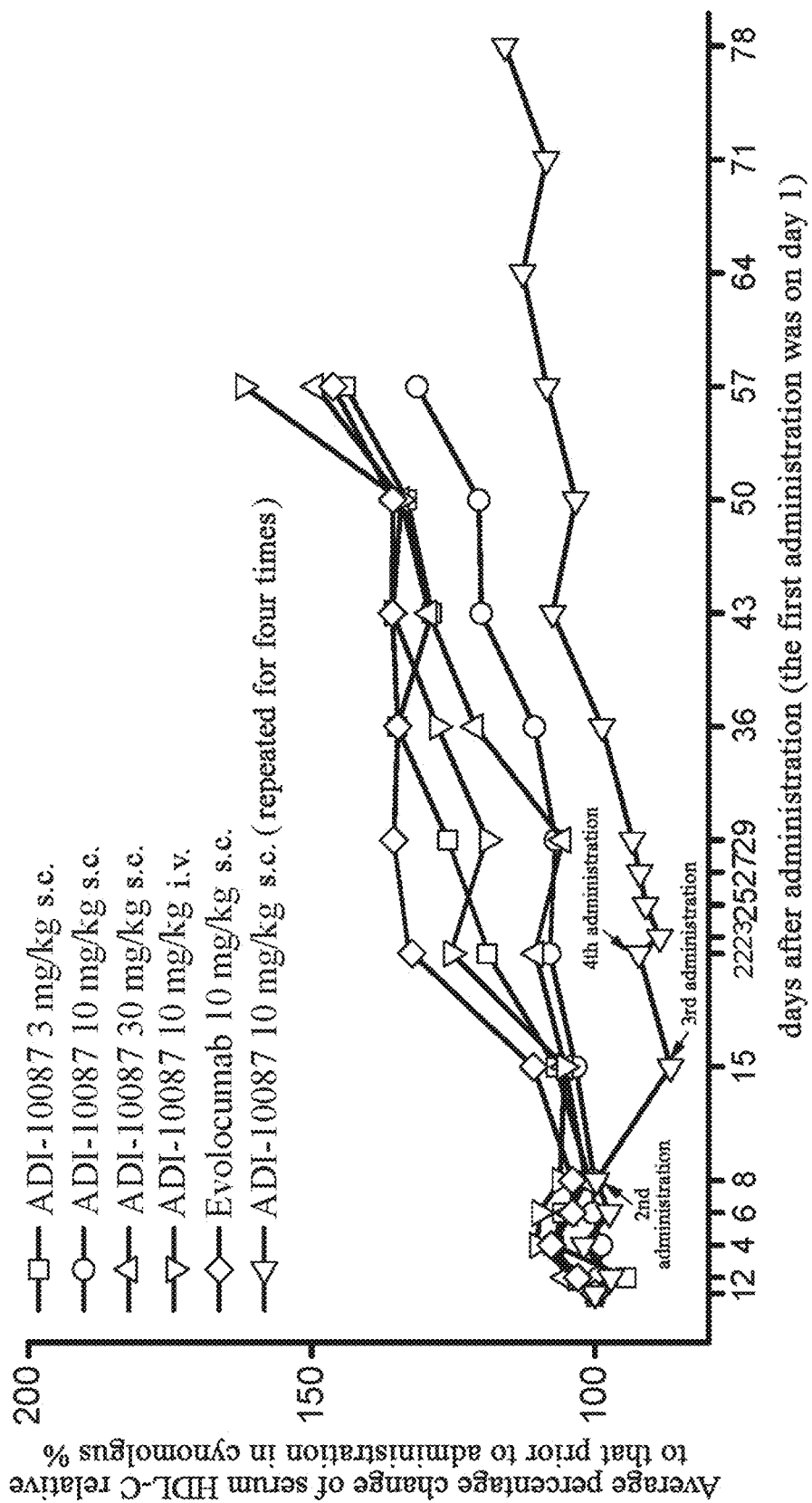
FIG. 12 is a graph plotting the % change rate (average) of the level of serum HDL-C relative to that prior to the administration (prior to D1 administration, baseline) versus time, after administration of anti-PCSK-9 antibodies or Evolocumab to cynomolgus.

As a whole, administration of the anti-PCSK9 antibody did not significantly affect the serum level of HDL-C in cynomolgus (FIG. 12).

However, the applicant has surprisingly found that after a single subcutaneous administration to cynomolgus of 10 mg/kg anti-PCSK9 antibody of the present application and Evolocumab, respectively, for Evolocumab administration, the significant decrease in LDL-C relative to the baseline level lasted for only 14 days, which was shorter than 21 days after administration of the antibody of the present application. That is, the duration for anti-PCSK9 antibody of the present application induced significant decrease in LDL-C was longer than that for Evolocumab.

The above method is also applicable for the other antibodies of the present invention for determination.

The invention claimed is:

1. Anti-proprotein convertase subtilisin/kexin type 9 (PCSK9) antibody or the antigen binding fragment thereof, which comprises a heavy chain variable region (HCVR) and a light chain variable region (LCVR), wherein said HCVR comprises complementary determinant regions (CDR) HCDR1, HCDR2 and HCDR3 and said LCVR comprises CDR LCDR1, LCDR2 and LCDR3, wherein HCDR1 comprises or consists of the amino acid sequence of SEQ ID NOs: 1, 7, 8, 9, 10, 11, 12, 13 or 20; HCDR2 comprises or consists of the amino acid sequence of SEQ ID NOs: 2, 14, 15, 16, 17 or 21; and HCDR3 comprises or consists of the amino acid sequence of SEQ ID NOs: 3, 18, 19 or 22; wherein LCDR1 comprises or consists of the amino acid sequence of SEQ ID NO:4; LCDR2 comprises or consists of the amino acid sequence of SEQ ID NO:5; and LCDR3 comprises or consists of the amino acid sequence of SEQ ID NO:6.

2. The antibody or the antigen binding fragment thereof of claim 1, wherein
   (a) the heavy chain variable region HCVR comprises or consists of the amino acid sequence of SEQ ID NO: 23; and wherein the light chain variable region LCVR comprises or consists of the amino acid sequence of SEQ ID NO: 24;
   (b) the heavy chain variable region HCVR comprises or consists of the amino acid sequence of SEQ ID NO: 25; and the light chain variable region LCVR comprises or consists of the amino acid sequence of SEQ ID NO: 24;
   (c) the heavy chain variable region HCVR comprises or consists of the amino acid sequence of SEQ ID NO: 26; and the light chain variable region LCVR comprises or consists of the amino acid sequence of SEQ ID NO: 24;
   (d) the heavy chain variable region HCVR comprises or consists of the amino acid sequence of SEQ ID NO: 27; and the light chain variable region LCVR comprises or consists of the amino acid sequence of SEQ ID NO: 24;
   (e) the heavy chain variable region HCVR comprises or consists of the amino acid sequence of SEQ ID NO: 28; and the light chain variable region LCVR comprises or consists of the amino acid sequence of SEQ ID NO: 24;
   (f) the heavy chain variable region HCVR comprises or consists of the amino acid sequence of SEQ ID NO: 29; and the light chain variable region LCVR comprises or consists of the amino acid sequence of SEQ ID NO: 24;
   (g) the heavy chain variable region HCVR comprises or consists of the amino acid sequence of SEQ ID NO: 30; and the light chain variable region LCVR comprises or consists of the amino acid sequence of SEQ ID NO: 24;
   (h) the heavy chain variable region HCVR comprises or consists of the amino acid sequence of SEQ ID NO: 31; and the light chain variable region LCVR comprises or consists of the amino acid sequence of SEQ ID NO: 24;
   (i) the heavy chain variable region HCVR comprises or consists of the amino acid sequence of SEQ ID NO: 32; and the light chain variable region LCVR comprises or consists of the amino acid sequence of SEQ ID NO: 24; or
   (j) the heavy chain variable region HCVR comprises or consists of the amino acid sequence of SEQ ID NO: 33; and the light chain variable region LCVR comprises or consists of the amino acid sequence of SEQ ID NO: 24.

3. The antibody or the antigen binding fragment thereof of claim 1, which comprises a heavy chain and a light chain, wherein
   (a) the heavy chain comprises or consists of the amino acid sequence of SEQ ID NO: 34; and the light chain comprises or consists of the amino acid sequence of SEQ ID NO:35;
   (b) the heavy chain comprises or consists of the amino acid sequence of SEQ ID NO: 36; and the light chain comprises or consists of the amino acid sequence of SEQ ID NO:35;
   (c) the heavy chain comprises or consists of the amino acid sequence of SEQ ID NO: 37; and the light chain comprises or consists of the amino acid sequence of SEQ ID NO:35;
   (d) the heavy chain comprises or consists of the amino acid sequence of SEQ ID NO: 38; and the light chain comprises or consists of the amino acid sequence of SEQ ID NO:35;
   (e) the heavy chain comprises or consists of the amino acid sequence of SEQ ID NO: 39; and the light chain comprises or consists of the amino acid sequence of SEQ ID NO:35;
   (f) the heavy chain comprises or consists of the amino acid sequence of SEQ ID NO: 40; and the light chain comprises or consists of the amino acid sequence of SEQ ID NO:35;
   (g) the heavy chain comprises or consists of the amino acid sequence of SEQ ID NO: 41; and the light chain comprises or consists of the amino acid sequence of SEQ ID NO:35;
   (h) the heavy chain comprises or consists of the amino acid sequence of SEQ ID NO: 42; and the light chain comprises or consists of the amino acid sequence of SEQ ID NO:35;
   (i) the heavy chain comprises or consists of the amino acid sequence of SEQ ID NO: 43; and the light chain comprises or consists of the amino acid sequence of SEQ ID NO:35; or
   (j) the heavy chain comprises or consists of the amino acid sequence of SEQ ID NO: 44; and the light chain comprises or consists of the amino acid sequence of SEQ ID NO:35.

4. The antibody or the antigen binding fragment thereof of claim 1, wherein
   (a) HCDR1 comprises or consists of the amino acid sequence of SEQ ID NO:20, HCDR2 comprises or consists of the amino acid sequence of SEQ ID NO:21, and HCDR3 comprises or consists of the amino acid sequence of SEQ ID NO:22; and wherein LCDR1 comprises or consists of the amino acid sequence of SEQ ID NO: 4, LCDR2 comprises or consists of the amino acid sequence of SEQ ID NO: 5, and LCDR3 comprises or consists of the amino acid sequence of SEQ ID NO: 6;
   (b) HCDR1 comprises or consists of the amino acid sequence of SEQ ID NO:1, HCDR2 comprises or consists of the amino acid sequence of SEQ ID NO:2, and HCDR3 comprises or consists of the amino acid sequence of SEQ ID NO:3; and LCDR1 comprises or consists of the amino acid sequence of SEQ ID NO: 4, LCDR2 comprises or consists of the amino acid sequence of SEQ ID NO: 5, and LCDR3 comprises or consists of the amino acid sequence of SEQ ID NO: 6;
   (c) HCDR1 comprises or consists of the amino acid sequence of SEQ ID NO:1, HCDR2 comprises or consists of the amino acid sequence of SEQ ID NO:2, and HCDR3 comprises or consists of the amino acid sequence of SEQ ID NO:18; and LCDR1 comprises or consists of the amino acid sequence of SEQ ID NO: 4, LCDR2 comprises or consists of the amino acid sequence of SEQ ID NO: 5, and LCDR3 comprises or consists of the amino acid sequence of SEQ ID NO: 6;

(d) HCDR1 comprises or consists of the amino acid sequence of SEQ ID NO:1, HCDR2 comprises or consists of the amino acid sequence of SEQ ID NO:14, and HCDR3 comprises or consists of the amino acid sequence of SEQ ID NO:19; and LCDR1 comprises or consists of the amino acid sequence of SEQ ID NO:4, LCDR2 comprises or consists of the amino acid sequence of SEQ ID NO:5, and LCDR3 comprises or consists of the amino acid sequence of SEQ ID NO:6;

(e) HCDR1 comprises or consists of the amino acid sequence of SEQ ID NO:7, HCDR2 comprises or consists of the amino acid sequence of SEQ ID NO:15, and HCDR3 comprises or consists of the amino acid sequence of SEQ ID NO: 18; and LCDR1 comprises or consists of the amino acid sequence of SEQ ID NO: 4, LCDR2 comprises or consists of the amino acid sequence of SEQ ID NO: 5, and LCDR3 comprises or consists of the amino acid sequence of SEQ ID NO: 6;

(f) HCDR1 comprises or consists of the amino acid sequence of SEQ ID NO:8, HCDR2 comprises or consists of the amino acid sequence of SEQ ID NO:16, and HCDR3 comprises or consists of the amino acid sequence of SEQ ID NO: 19; and LCDR1 comprises or consists of the amino acid sequence of SEQ ID NO: 4, LCDR2 comprises or consists of the amino acid sequence of SEQ ID NO:5, and LCDR3 comprises or consists of the amino acid sequence of SEQ ID NO: 6;

(g) HCDR1 comprises or consists of the amino acid sequence of SEQ ID NO:9, HCDR2 comprises or consists of the amino acid sequence of SEQ ID NO:17, and HCDR3 comprises or consists of the amino acid sequence of SEQ ID NO: 19; and LCDR1 comprises or consists of the amino acid sequence of SEQ ID NO: 4, LCDR2 comprises or consists of the amino acid sequence of SEQ ID NO:5, and LCDR3 comprises or consists of the amino acid sequence of SEQ ID NO: 6;

(h) HCDR1 comprises or consists of the amino acid sequence of SEQ ID NO:10, HCDR2 comprises or consists of the amino acid sequence of SEQ ID NO:17, and HCDR3 comprises or consists of the amino acid sequence of SEQ ID NO: 19; and LCDR1 comprises or consists of the amino acid sequence of SEQ ID NO: 4, LCDR2 comprises or consists of the amino acid sequence of SEQ ID NO: 5, and LCDR3 comprises or consists of the amino acid sequence of SEQ ID NO: 6;

(i) HCDR1 comprises or consists of the amino acid sequence of SEQ ID NO:11, HCDR2 comprises or consists of the amino acid sequence of SEQ ID NO: 17, and HCDR3 comprises or consists of the amino acid sequence of SEQ ID NO: 18; and LCDR1 comprises or consists of the amino acid sequence of SEQ ID NO: 4, LCDR2 comprises or consists of the amino acid sequence of SEQ ID NO: 5, and LCDR3 comprises or consists of the amino acid sequence of SEQ ID NO: 6;

(j) HCDR1 comprises or consists of the amino acid sequence of SEQ ID NO:12, HCDR2 comprises or consists of the amino acid sequence of SEQ ID NO:17, and HCDR3 comprises or consists of the amino acid sequence of SEQ ID NO: 18; and LCDR1 comprises or consists of the amino acid sequence of SEQ ID NO: 4, LCDR2 comprises or consists of the amino acid sequence of SEQ ID NO: 5, and LCDR3 comprises or consists of the amino acid sequence of SEQ ID NO: 6; or (k) HCDR1 comprises or consists of the amino acid sequence of SEQ ID NO:13, HCDR2 comprises or consists of the amino acid sequence of SEQ ID NO: 17, and HCDR3 comprises or consists of the amino acid sequence of SEQ ID NO: 18; and LCDR1 comprises or consists of the amino acid sequence of SEQ ID NO: 4, LCDR2 comprises or consists of the amino acid sequence of SEQ ID NO: 5, and LCDR3 comprises or consists of the amino acid sequence of SEQ ID NO: 6.

5. The antibody or the antigen binding fragment thereof of claim 4, wherein the HCVR comprises or consists of an amino acid sequence having at least 90% identity with an amino acid sequence selected from the group consisting of SEQ ID NOs: 23, 25, 26, 27, 28, 29, 30, 31, 32 and 33 and/or the LCVR comprises or consists of an amino acid sequence having at least 90% identity with the amino acid sequence of SEQ ID NO:24.

6. The antibody or the antigen binding fragment thereof of claim 4, comprising a heavy chain, wherein the heavy chain comprises or consists of an amino acid sequence having at least 90% identity with the amino acid sequence selected from SEQ ID NOs: 34, 36, 37, 38, 39, 40, 41, 42, 43 and 44, and/or the light chain comprises or consists of an amino acid sequence having at least 90% identity with the amino acid sequence of SEQ ID NO:35.

7. The antibody or the antigen binding fragment thereof of claim 4, wherein said antibody is a monoclonal antibody, a humanized antibody or a human antibody.

8. The antibody or the antigen binding fragment thereof of claim 4, wherein said antigen binding fragment is a fragment selected from Fab, Fab'-SH, Fv, scFv or (Fab')2 fragment.

9. A pharmaceutical composition comprising the anti-PCSK9 antibody or the antigen-binding fragment of claim 1 and optionally a pharmaceutically acceptable carrier.

10. A pharmaceutical composition comprising the anti-PCSK9 antibody or the antigen-binding fragment of claim 4 and optionally a pharmaceutically acceptable carrier.

11. A pharmaceutical composition comprising the anti-PCSK9 antibody or the antigen-binding fragment of claim 2 and optionally a pharmaceutically acceptable carrier.

12. An isolated nucleic acid encoding the anti-PCSK9 antibody or the antigen binding fragment thereof of claim 4.

13. A vector comprising the nucleic acid of claim 12.

14. An isolated mammalian cell comprising the nucleic acid of claim 12.

15. A method for preparing an anti-PCSK9 antibody or the antigen-binding fragment thereof, said method comprising culturing the isolated mammalian cell of claim 14 under conditions suitable for expression of the anti-PCSK9 antibody or the antigen-binding fragment thereof, optionally isolating said antibody or the antigen-binding fragment thereof, optionally said method further comprises recovering the anti-PCSK9 antibody or the antigen-binding fragment thereof from the isolated mammalian cell.

16. A method of reducing LDL-cholesterol level in a subject, said method comprising administering to the subject an effective amount of the anti-PCSK9 antibody or the antigen-binding fragment thereof of claim 1.

17. A method of treating hypercholesterolemia and/or hyperlipidemia in a subject, said method comprising administering to the subject an effective amount of the anti-PCSK9 antibody or the antigen-binding fragment thereof of claim 1.

18. The method of claim 17, wherein said method treats hypercholesterolemia.

19. The method of claim 17, further comprising administering to the subject an effective amount of a second medicament, wherein the anti-PCSK9 antibody or the antigen binding fragment thereof is the first medicament, wherein said second medicament comprises a statin.

20. A method of reducing cholesterol level in a subject, said method comprising administering to the subject an effective amount of the anti-PCSK9 antibody or the antigen-binding fragment thereof of claim 4.

21. The method of claim 20, wherein said cholesterol is LDL-cholesterol.

22. A method of treating hypercholesterolemia and/or hyperlipidemia in a subject, said method comprising administering to the subject an effective amount of the anti-PCSK9 antibody or the antigen-binding fragment thereof of claim 4.

23. The method of claim 22, wherein said method treats hypercholesterolemia.

24. The method of claim 22, further comprising administering to the subject an effective amount of a second medicament, wherein the anti-PCSK9 antibody or the antigen binding fragment thereof is the first medicament.

25. The method of claim 24, wherein said second medicament comprises a statin.

26. The method of claim 25, wherein said statin is selected from the group consisting of atorvastatin, fluvastatin, lovastatin, mevastatin, pitavastatin, pravastatin, rosuvastatin, simvastatin, and any combination thereof.

27. A method of reducing LDL-cholesterol level in a subject, said method comprising administering to the subject an effective amount of the anti-PCSK9 antibody or the antigen-binding fragment thereof of claim 2.

28. A method of treating hypercholesterolemia and/or hyperlipidemia in a subject, said method comprising administering to the subject an effective amount of the anti-PCSK9 antibody or the antigen-binding fragment thereof of claim 2.

29. The method of claim 28, wherein said method treats hypercholesterolemia.

\* \* \* \* \*

SEQUENCE LISTING

<160> NUMBER OF SEQ ID NOS: 59

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic peptide
<220> FEATURE:

```
<223> OTHER INFORMATION: heavy chain variable region CDR1

<400> SEQUENCE: 1

Gly Ser Ile Ser Ser Ser Ser Tyr Tyr Trp Gly
1               5                   10

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain variable region CDR2

<400> SEQUENCE: 2

Ser Ile Tyr Tyr Ser Gly Ser Thr Tyr Tyr Asn Pro Ser Leu Lys Ser
1               5                   10                  15

<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain variable region CDR3

<400> SEQUENCE: 3

Ala Arg Glu Gly Ser Gly Val Val Pro Ala Ala Gly Pro Asn Trp Phe
1               5                   10                  15

Asp Pro

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: light chain variable region CDR1

<400> SEQUENCE: 4

Arg Ala Ser Gln Ser Val Ser Ser Tyr Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: light chain variable region CDR2

<400> SEQUENCE: 5

Asp Ala Ser Asn Arg Ala Thr
1               5

<210> SEQ ID NO 6
<211> LENGTH: 8
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: light chain variable region CDR3

<400> SEQUENCE: 6

Gln Gln Arg Arg Asn Trp Phe Thr
1               5

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain variable region CDR1

<400> SEQUENCE: 7

Gly Ser Val Ser Ser Ser Ser Tyr Tyr Trp Gly
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain variable region CDR1

<400> SEQUENCE: 8

Gly Ser Ile Val Ser Ser Ser Tyr Tyr Trp Ala
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain variable region CDR1

<400> SEQUENCE: 9

Gly Ser Ile Arg Ser Ser Ala Tyr Tyr Trp Gly
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain variable region CDR1

<400> SEQUENCE: 10

Gly Ser Ile Ser Ser Ala Ser Tyr Tyr Trp Ser
1               5                   10

<210> SEQ ID NO 11
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: heavy chain variable region CDR1

<400> SEQUENCE: 11

Gly Ser Ile Gly Ser Ser Ser Tyr Tyr Trp Ala
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain variable region CDR1

<400> SEQUENCE: 12

Gly Ser Ile Gly Ser Ser Ser Tyr Tyr Trp Thr
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain variable region CDR1

<400> SEQUENCE: 13

Gly Ser Ile Trp Ser Ser Ser Tyr Tyr Trp Thr
1               5                   10

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain variable region CDR2

<400> SEQUENCE: 14

Ser Ile Tyr Tyr Ser Gly Ser Thr Tyr Tyr Asn Pro Phe Leu Lys Ser
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain variable region CDR2

<400> SEQUENCE: 15

Ser Ala Tyr Tyr Ser Gly Ser Thr Tyr Tyr Asn Pro Ser Leu Lys Ser
1               5                   10                  15

<210> SEQ ID NO 16
<211> LENGTH: 16
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain variable region CDR2

<400> SEQUENCE: 16

Ser Ile Asn Tyr Lys Gly Ser Thr Tyr Tyr Asn Pro Ser Leu Lys Ser
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain variable region CDR2

<400> SEQUENCE: 17

Ser Ile Asn Tyr Arg Gly Ser Thr Tyr Tyr Asn Pro Ser Leu Lys Ser
1               5                   10                  15

<210> SEQ ID NO 18
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain variable region CDR3

<400> SEQUENCE: 18

Ala Arg Glu Asn Ser Gly Val Val Pro Ala Ala Gly Pro Asn Trp Phe
1               5                   10                  15

Asp Pro

<210> SEQ ID NO 19
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain variable region CDR3

<400> SEQUENCE: 19

Ala Arg Glu Asn Ser Gly Val Val Pro Ala Ala Gly Pro Asn Trp Phe
1               5                   10                  15

Gly Pro

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain variable region CDR1
<220> FEATURE:
<221> NAME/KEY: MOD_RES
<222> LOCATION: (3)..(3)
<223> OTHER INFORMATION: Xaa is selected from V and I
<220> FEATURE:
```

```
<221> NAME/KEY: MOD_RES
<222> LOCATION: (4)..(4)
<223> OTHER INFORMATION: Xaa is selected from S, V, R, G or W
<220> FEATURE:
<221> NAME/KEY: MOD_RES
<222> LOCATION: (6)..(6)
<223> OTHER INFORMATION: Xaa is selected from S or A
<220> FEATURE:
<221> NAME/KEY: MOD_RES
<222> LOCATION: (7)..(7)
<223> OTHER INFORMATION: Xaa is selected from S or A
<220> FEATURE:
<221> NAME/KEY: MOD_RES
<222> LOCATION: (11)..(11)
<223> OTHER INFORMATION: Xaa is selected from G, A, S or T

<400> SEQUENCE: 20

Gly Ser Xaa Xaa Ser Xaa Xaa Tyr Tyr Trp Xaa
1               5                   10

<210> SEQ ID NO 21
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain variable region CDR2
<220> FEATURE:
<221> NAME/KEY: MOD_RES
<222> LOCATION: (2)..(2)
<223> OTHER INFORMATION: Xaa is selected from I or A
<220> FEATURE:
<221> NAME/KEY: MOD_RES
<222> LOCATION: (3)..(3)
<223> OTHER INFORMATION: Xaa is selected from Y or N
<220> FEATURE:
<221> NAME/KEY: MOD_RES
<222> LOCATION: (5)..(5)
<223> OTHER INFORMATION: Xaa is selected from S, K or R
<220> FEATURE:
<221> NAME/KEY: MOD_RES
<222> LOCATION: (13)..(13)
<223> OTHER INFORMATION: Xaa is selected from S or F

<400> SEQUENCE: 21

Ser Xaa Xaa Tyr Xaa Gly Ser Thr Tyr Tyr Asn Pro Xaa Leu Lys Ser
1               5                   10                  15

<210> SEQ ID NO 22
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain variable region CDR3
<220> FEATURE:
<221> NAME/KEY: MOD_RES
<222> LOCATION: (4)..(4)
<223> OTHER INFORMATION: Xaa is selected from G or N
<220> FEATURE:
<221> NAME/KEY: MOD_RES
<222> LOCATION: (17)..(17)
<223> OTHER INFORMATION: Xaa is selected from D or G

<400> SEQUENCE: 22

Ala Arg Glu Xaa Ser Gly Val Val Pro Ala Ala Gly Pro Asn Trp Phe
1               5                   10                  15

Xaa Pro
```

```
<210> SEQ ID NO 23
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ADI-02396: heavy chain variable region

<400> SEQUENCE: 23

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Gly Ser Gly Val Val Pro Ala Ala Gly Pro Asn Trp
            100                 105                 110

Phe Asp Pro Trp Gly Gln Gly Thr Leu Val Thr Val Ser Ser
        115                 120                 125

<210> SEQ ID NO 24
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: light chain variable region

<400> SEQUENCE: 24

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Arg Asn Trp Phe Thr
                85                  90                  95

Phe Gly Gly Gly Thr Lys Val Glu Ile Lys
            100                 105

<210> SEQ ID NO 25
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<223> OTHER INFORMATION: ADI-09111: heavy chain variable region

<400> SEQUENCE: 25

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asn Ser Gly Val Val Pro Ala Ala Gly Pro Asn Trp
            100                 105                 110

Phe Asp Pro Trp Gly Gln Gly Thr Leu Val Thr Val Ser Ser
        115                 120                 125

<210> SEQ ID NO 26
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ADI-09112: heavy chain variable region

<400> SEQUENCE: 26

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Phe
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asn Ser Gly Val Val Pro Ala Ala Gly Pro Asn Trp
            100                 105                 110

Phe Gly Pro Trp Gly Gln Gly Thr Leu Val Thr Val Ser Ser
        115                 120                 125

<210> SEQ ID NO 27
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ADI-09113: heavy chain variable region

<400> SEQUENCE: 27
```

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ala Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Glu Asn Ser Gly Val Val Pro Ala Ala Gly Pro Asn Trp
            100                 105                 110

Phe Asp Pro Trp Gly Gln Gly Thr Leu Val Thr Val Ser Ser
        115                 120                 125

<210> SEQ ID NO 28
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ADI-10085: heavy chain variable region

<400> SEQUENCE: 28

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Val Ser Ser
            20                  25                  30

Ser Tyr Tyr Trp Ala Trp Ile Arg Gln Pro Pro Gly Lys Gly Leu Glu
        35                  40                  45

Trp Ile Gly Ser Ile Asn Tyr Lys Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Glu Asn Ser Gly Val Val Pro Ala Ala Gly Pro Asn Trp
            100                 105                 110

Phe Gly Pro Trp Gly Gln Gly Thr Leu Val Thr Val Ser Ser
        115                 120                 125

<210> SEQ ID NO 29
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ADI-10086: heavy chain variable region

<400> SEQUENCE: 29

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Arg Ser Ser
            20                  25                  30

Ala Tyr Tyr Trp Gly Trp Ile Arg Gln Pro Pro Gly Lys Gly Leu Glu
            35                  40                  45

Trp Ile Gly Ser Ile Asn Tyr Arg Gly Ser Thr Tyr Tyr Asn Pro Ser
        50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asn Ser Gly Val Val Pro Ala Ala Gly Pro Asn Trp
                100                 105                 110

Phe Gly Pro Trp Gly Gln Gly Thr Leu Val Thr Val Ser Ser
            115                 120                 125

<210> SEQ ID NO 30
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ADI-10087: heavy chain variable region

<400> SEQUENCE: 30

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ala
                20                  25                  30

Ser Tyr Tyr Trp Ser Trp Ile Arg Gln Pro Pro Gly Lys Gly Leu Glu
            35                  40                  45

Trp Ile Gly Ser Ile Asn Tyr Arg Gly Ser Thr Tyr Tyr Asn Pro Ser
        50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asn Ser Gly Val Val Pro Ala Ala Gly Pro Asn Trp
                100                 105                 110

Phe Gly Pro Trp Gly Gln Gly Thr Leu Val Thr Val Ser Ser
            115                 120                 125

<210> SEQ ID NO 31
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ADI-10088: heavy chain variable region

<400> SEQUENCE: 31

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Gly Ser Ser
                20                  25                  30

Ser Tyr Tyr Trp Ala Trp Ile Arg Gln Pro Pro Gly Lys Gly Leu Glu
            35                  40                  45

Trp Ile Gly Ser Ile Asn Tyr Arg Gly Ser Thr Tyr Tyr Asn Pro Ser

```
                    50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                     85                  90                  95

Cys Ala Arg Glu Asn Ser Gly Val Val Pro Ala Ala Gly Pro Asn Trp
                    100                 105                 110

Phe Asp Pro Trp Gly Gln Gly Thr Leu Val Thr Val Ser Ser
            115                 120                 125

<210> SEQ ID NO 32
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ADI-10089: heavy chain variable region

<400> SEQUENCE: 32

Gln Leu Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Gly Ser Ser
             20                  25                  30

Ser Tyr Tyr Trp Thr Trp Ile Arg Gln Pro Pro Gly Lys Gly Leu Glu
         35                  40                  45

Trp Ile Gly Ser Ile Asn Tyr Arg Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                     85                  90                  95

Cys Ala Arg Glu Asn Ser Gly Val Val Pro Ala Ala Gly Pro Asn Trp
                    100                 105                 110

Phe Asp Pro Trp Gly Gln Gly Thr Leu Val Thr Val Ser Ser
            115                 120                 125

<210> SEQ ID NO 33
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ADI-10090: heavy chain variable region

<400> SEQUENCE: 33

Gln Leu Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Trp Ser Ser
             20                  25                  30

Ser Tyr Tyr Trp Thr Trp Ile Arg Gln Pro Pro Gly Lys Gly Leu Glu
         35                  40                  45

Trp Ile Gly Ser Ile Asn Tyr Arg Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80
```

```
Ser Leu Lys Leu Ser Ser Val Thr Ala Ala Asp Thr Ala Val Tyr Tyr
                 85                  90                  95

Cys Ala Arg Glu Asn Ser Gly Val Val Pro Ala Ala Gly Pro Asn Trp
            100                 105                 110

Phe Asp Pro Trp Gly Gln Gly Thr Leu Val Thr Val Ser Ser
        115                 120                 125

<210> SEQ ID NO 34
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ADI-02396: heavy chain

<400> SEQUENCE: 34

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Gly Ser Gly Val Val Pro Ala Ala Gly Pro Asn Trp
            100                 105                 110

Phe Asp Pro Trp Gly Gln Gly Thr Leu Val Thr Val Ser Ser Ala Ser
        115                 120                 125

Thr Lys Gly Pro Ser Val Phe Pro Leu Ala Pro Cys Ser Arg Ser Thr
130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Asn Phe Gly Thr Gln Thr Tyr Thr
        195                 200                 205

Cys Asn Val Asp His Lys Pro Ser Asn Thr Lys Val Asp Lys Thr Val
210                 215                 220

Glu Arg Lys Cys Cys Val Glu Cys Pro Pro Cys Pro Ala Pro Pro Val
225                 230                 235                 240

Ala Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
        290                 295                 300
```

Phe Arg Val Val Ser Val Leu Thr Val Val His Gln Asp Trp Leu Asn
305                 310                 315                 320

Gly Lys Glu Tyr Lys Cys Lys Val Ser Asn Lys Gly Leu Pro Ala Pro
            325                 330                 335

Ile Glu Lys Thr Ile Ser Lys Thr Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Met Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 35
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: light chain

<400> SEQUENCE: 35

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Arg Asn Trp Phe Thr
            85                  90                  95

Phe Gly Gly Gly Thr Lys Val Glu Ile Lys Arg Thr Val Ala Ala Pro
        100                 105                 110

Ser Val Phe Ile Phe Pro Pro Ser Asp Glu Gln Leu Lys Ser Gly Thr
    115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
            165                 170                 175

Thr Leu Thr Leu Ser Lys Ala Asp Tyr Glu Lys His Lys Val Tyr Ala
        180                 185                 190

```
Cys Glu Val Thr His Gln Gly Leu Ser Ser Pro Val Thr Lys Ser Phe
            195                 200                 205

Asn Arg Gly Glu Cys
    210
```

<210> SEQ ID NO 36
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ADI-09111: heavy chain

<400> SEQUENCE: 36

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asn Ser Gly Val Val Pro Ala Ala Gly Pro Asn Trp
            100                 105                 110

Phe Asp Pro Trp Gly Gln Gly Thr Leu Val Thr Val Ser Ser Ala Ser
        115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Asn Phe Gly Thr Gln Thr Tyr Thr
        195                 200                 205

Cys Asn Val Asp His Lys Pro Ser Asn Thr Lys Val Asp Lys Thr Val
    210                 215                 220

Glu Arg Lys Cys Cys Val Glu Cys Pro Pro Cys Pro Ala Pro Pro Val
225                 230                 235                 240

Ala Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Phe Arg Val Val Ser Val Leu Thr Val Val His Gln Asp Trp Leu Asn
305                 310                 315                 320
```

Gly Lys Glu Tyr Lys Cys Lys Val Ser Asn Lys Gly Leu Pro Ala Pro
             325                 330                 335

Ile Glu Lys Thr Ile Ser Lys Thr Lys Gly Gln Pro Arg Glu Pro Gln
         340                 345                 350

Val Tyr Thr Leu Pro Pro Ser Arg Glu Glu Met Thr Lys Asn Gln Val
     355                 360                 365

Ser Leu Thr Cys Leu Val Lys Gly Phe Tyr Pro Ser Asp Ile Ala Val
     370                 375                 380

Glu Trp Glu Ser Asn Gly Gln Pro Glu Asn Asn Tyr Lys Thr Thr Pro
385                 390                 395                 400

Pro Met Leu Asp Ser Asp Gly Ser Phe Phe Leu Tyr Ser Lys Leu Thr
                 405                 410                 415

Val Asp Lys Ser Arg Trp Gln Gln Gly Asn Val Phe Ser Cys Ser Val
             420                 425                 430

Met His Glu Ala Leu His Asn His Tyr Thr Gln Lys Ser Leu Ser Leu
         435                 440                 445

Ser Pro Gly
    450

<210> SEQ ID NO 37
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ADI-09112: heavy chain

<400> SEQUENCE: 37

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
             20                  25                  30

Ser Tyr Tyr Trp Gly Trp Ile Arg Gln Pro Pro Gly Lys Gly Leu Glu
         35                  40                  45

Trp Ile Gly Ser Ile Tyr Tyr Ser Gly Ser Thr Tyr Tyr Asn Pro Phe
     50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                 85                  90                  95

Cys Ala Arg Glu Asn Ser Gly Val Val Pro Ala Ala Gly Pro Asn Trp
             100                 105                 110

Phe Gly Pro Trp Gly Gln Gly Thr Leu Val Thr Val Ser Ser Ala Ser
         115                 120                 125

Thr Lys Gly Pro Ser Val Phe Pro Leu Ala Pro Cys Ser Arg Ser Thr
     130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                 165                 170                 175

His Thr Phe Pro Ala Val Leu Gln Ser Ser Gly Leu Tyr Ser Leu Ser
             180                 185                 190

Ser Val Val Thr Val Pro Ser Ser Asn Phe Gly Thr Gln Thr Tyr Thr
         195                 200                 205

```
Cys Asn Val Asp His Lys Pro Ser Asn Thr Lys Val Asp Lys Thr Val
        210                 215                 220

Glu Arg Lys Cys Cys Val Glu Cys Pro Pro Cys Pro Ala Pro Pro Val
225                 230                 235                 240

Ala Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
        260                 265                 270

His Glu Asp Pro Glu Val Gln Phe Asn Trp Tyr Val Asp Gly Val Glu
    275                 280                 285

Val His Asn Ala Lys Thr Lys Pro Arg Glu Glu Gln Phe Asn Ser Thr
290                 295                 300

Phe Arg Val Val Ser Val Leu Thr Val Val His Gln Asp Trp Leu Asn
305                 310                 315                 320

Gly Lys Glu Tyr Lys Cys Lys Val Ser Asn Lys Gly Leu Pro Ala Pro
            325                 330                 335

Ile Glu Lys Thr Ile Ser Lys Thr Lys Gly Gln Pro Arg Glu Pro Gln
        340                 345                 350

Val Tyr Thr Leu Pro Pro Ser Arg Glu Glu Met Thr Lys Asn Gln Val
    355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Met Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
        420                 425                 430

Met His Glu Ala Leu His Asn His Tyr Thr Gln Lys Ser Leu Ser Leu
    435                 440                 445

Ser Pro Gly
450

<210> SEQ ID NO 38
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ADI-09113: heavy chain

<400> SEQUENCE: 38

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ala Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95
```

Cys Ala Arg Glu Asn Ser Gly Val Val Pro Ala Ala Gly Pro Asn Trp
            100                 105                 110

Phe Asp Pro Trp Gly Gln Gly Thr Leu Val Thr Val Ser Ser Ala Ser
        115                 120                 125

Thr Lys Gly Pro Ser Val Phe Pro Leu Ala Pro Cys Ser Arg Ser Thr
130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Asn Phe Gly Thr Gln Thr Tyr Thr
        195                 200                 205

Cys Asn Val Asp His Lys Pro Ser Asn Thr Lys Val Asp Lys Thr Val
210                 215                 220

Glu Arg Lys Cys Cys Val Glu Cys Pro Pro Cys Pro Ala Pro Pro Val
225                 230                 235                 240

Ala Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
290                 295                 300

Phe Arg Val Val Ser Val Leu Thr Val Val His Gln Asp Trp Leu Asn
305                 310                 315                 320

Gly Lys Glu Tyr Lys Cys Lys Val Ser Asn Lys Gly Leu Pro Ala Pro
                325                 330                 335

Ile Glu Lys Thr Ile Ser Lys Thr Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Met Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 39
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ADI-10085: heavy chain

<400> SEQUENCE: 39

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Val Ser Ser
            20                  25                  30

Ser Tyr Tyr Trp Ala Trp Ile Arg Gln Pro Pro Gly Lys Gly Leu Glu
        35                  40                  45

Trp Ile Gly Ser Ile Asn Tyr Lys Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
            85                  90                  95

Cys Ala Arg Glu Asn Ser Gly Val Val Pro Ala Ala Gly Pro Asn Trp
        100                 105                 110

Phe Gly Pro Trp Gly Gln Gly Thr Leu Val Thr Val Ser Ser Ala Ser
        115                 120                 125

Thr Lys Gly Pro Ser Val Phe Pro Leu Ala Pro Cys Ser Arg Ser Thr
130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
            165                 170                 175

His Thr Phe Pro Ala Val Leu Gln Ser Ser Gly Leu Tyr Ser Leu Ser
        180                 185                 190

Ser Val Val Thr Val Pro Ser Ser Asn Phe Gly Thr Gln Thr Tyr Thr
        195                 200                 205

Cys Asn Val Asp His Lys Pro Ser Asn Thr Lys Val Asp Lys Thr Val
210                 215                 220

Glu Arg Lys Cys Cys Val Glu Cys Pro Pro Cys Pro Ala Pro Pro Val
225                 230                 235                 240

Ala Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
        260                 265                 270

His Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
290                 295                 300

Phe Arg Val Val Ser Val Leu Thr Val Val His Gln Asp Trp Leu Asn
305                 310                 315                 320

Gly Lys Glu Tyr Lys Cys Lys Val Ser Asn Lys Gly Leu Pro Ala Pro
            325                 330                 335

Ile Glu Lys Thr Ile Ser Lys Thr Lys Gly Gln Pro Arg Glu Pro Gln
        340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Met Leu Asp Ser Asp Gly Ser Phe Phe Leu Tyr Ser Lys Leu Thr

```
                        405                 410                 415
Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly
    450

<210> SEQ ID NO 40
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ADI-10086: heavy chain

<400> SEQUENCE: 40

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Arg Ser Ser
            20                  25                  30

Ala Tyr Tyr Trp Gly Trp Ile Arg Gln Pro Pro Gly Lys Gly Leu Glu
        35                  40                  45

Trp Ile Gly Ser Ile Asn Tyr Arg Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asn Ser Gly Val Val Pro Ala Ala Gly Pro Asn Trp
            100                 105                 110

Phe Gly Pro Trp Gly Gln Gly Thr Leu Val Thr Val Ser Ser Ala Ser
        115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Asn Phe Gly Thr Gln Thr Tyr Thr
        195                 200                 205

Cys Asn Val Asp His Lys Pro Ser Asn Thr Lys Val Asp Lys Thr Val
    210                 215                 220

Glu Arg Lys Cys Cys Val Glu Cys Pro Pro Cys Pro Ala Pro Pro Val
225                 230                 235                 240

Ala Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
```

```
            290                 295                 300

Phe Arg Val Val Ser Val Leu Thr Val His Gln Asp Trp Leu Asn
305                 310                 315                 320

Gly Lys Glu Tyr Lys Cys Lys Val Ser Asn Lys Gly Leu Pro Ala Pro
                325                 330                 335

Ile Glu Lys Thr Ile Ser Lys Thr Lys Gly Gln Pro Arg Glu Pro Gln
                340                 345                 350

Val Tyr Thr Leu Pro Pro Ser Arg Glu Glu Met Thr Lys Asn Gln Val
                355                 360                 365

Ser Leu Thr Cys Leu Val Lys Gly Phe Tyr Pro Ser Asp Ile Ala Val
                370                 375                 380

Glu Trp Glu Ser Asn Gly Gln Pro Glu Asn Asn Tyr Lys Thr Thr Pro
385                 390                 395                 400

Pro Met Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
                435                 440                 445

Ser Pro Gly
    450

<210> SEQ ID NO 41
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ADI-10087: heavy chain

<400> SEQUENCE: 41

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ala
                20                  25                  30

Ser Tyr Tyr Trp Ser Trp Ile Arg Gln Pro Pro Gly Lys Gly Leu Glu
            35                  40                  45

Trp Ile Gly Ser Ile Asn Tyr Arg Gly Ser Thr Tyr Tyr Asn Pro Ser
        50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asn Ser Gly Val Val Pro Ala Ala Gly Pro Asn Trp
                100                 105                 110

Phe Gly Pro Trp Gly Gln Gly Thr Leu Val Thr Val Ser Ser Ala Ser
            115                 120                 125

Thr Lys Gly Pro Ser Val Phe Pro Leu Ala Pro Cys Ser Arg Ser Thr
        130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
```

```
            180                 185                 190
Ser Val Val Thr Val Pro Ser Ser Asn Phe Gly Thr Gln Thr Tyr Thr
            195                 200                 205
Cys Asn Val Asp His Lys Pro Ser Asn Thr Lys Val Asp Lys Thr Val
            210                 215                 220
Glu Arg Lys Cys Cys Val Glu Cys Pro Pro Cys Pro Ala Pro Pro Val
225                 230                 235                 240
Ala Gly Pro Ser Val Phe Leu Phe Pro Pro Lys Pro Lys Asp Thr Leu
            245                 250                 255
Met Ile Ser Arg Thr Pro Glu Val Thr Cys Val Val Val Asp Val Ser
            260                 265                 270
His Glu Asp Pro Glu Val Gln Phe Asn Trp Tyr Val Asp Gly Val Glu
            275                 280                 285
Val His Asn Ala Lys Thr Lys Pro Arg Glu Glu Gln Phe Asn Ser Thr
            290                 295                 300
Phe Arg Val Val Ser Val Leu Thr Val Val His Gln Asp Trp Leu Asn
305                 310                 315                 320
Gly Lys Glu Tyr Lys Cys Lys Val Ser Asn Lys Gly Leu Pro Ala Pro
            325                 330                 335
Ile Glu Lys Thr Ile Ser Lys Thr Lys Gly Gln Pro Arg Glu Pro Gln
            340                 345                 350
Val Tyr Thr Leu Pro Pro Ser Arg Glu Glu Met Thr Lys Asn Gln Val
            355                 360                 365
Ser Leu Thr Cys Leu Val Lys Gly Phe Tyr Pro Ser Asp Ile Ala Val
            370                 375                 380
Glu Trp Glu Ser Asn Gly Gln Pro Glu Asn Asn Tyr Lys Thr Thr Pro
385                 390                 395                 400
Pro Met Leu Asp Ser Asp Gly Ser Phe Phe Leu Tyr Ser Lys Leu Thr
            405                 410                 415
Val Asp Lys Ser Arg Trp Gln Gln Gly Asn Val Phe Ser Cys Ser Val
            420                 425                 430
Met His Glu Ala Leu His Asn His Tyr Thr Gln Lys Ser Leu Ser Leu
            435                 440                 445
Ser Pro Gly
    450

<210> SEQ ID NO 42
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ADI-10088: heavy chain

<400> SEQUENCE: 42

Gln Leu Gln Leu Gln Glu Ser Gly Pro Gly Leu Val Lys Pro Ser Glu
1               5                   10                  15
Thr Leu Ser Leu Thr Cys Thr Val Ser Gly Gly Ser Ile Gly Ser Ser
            20                  25                  30
Ser Tyr Tyr Trp Ala Trp Ile Arg Gln Pro Pro Gly Lys Gly Leu Glu
            35                  40                  45
Trp Ile Gly Ser Ile Asn Tyr Arg Gly Ser Thr Tyr Tyr Asn Pro Ser
        50                  55                  60
Leu Lys Ser Arg Val Thr Ile Ser Val Asp Thr Ser Lys Asn Gln Phe
```

```
            65                  70                  75                  80
        Ser Leu Lys Leu Ser Ser Val Thr Ala Ala Asp Thr Ala Val Tyr Tyr
                        85                  90                  95

Cys Ala Arg Glu Asn Ser Gly Val Val Pro Ala Ala Gly Pro Asn Trp
                        100                 105                 110

Phe Asp Pro Trp Gly Gln Gly Thr Leu Val Thr Val Ser Ser Ala Ser
                        115                 120                 125

Thr Lys Gly Pro Ser Val Phe Pro Leu Ala Pro Cys Ser Arg Ser Thr
                        130                 135                 140

Ser Glu Ser Thr Ala Ala Leu Gly Cys Leu Val Lys Asp Tyr Phe Pro
        145                 150                 155                 160

Glu Pro Val Thr Val Ser Trp Asn Ser Gly Ala Leu Thr Ser Gly Val
                        165                 170                 175

His Thr Phe Pro Ala Val Leu Gln Ser Ser Gly Leu Tyr Ser Leu Ser
                        180                 185                 190

Ser Val Val Thr Val Pro Ser Ser Asn Phe Gly Thr Gln Thr Tyr Thr
                        195                 200                 205

Cys Asn Val Asp His Lys Pro Ser Asn Thr Lys Val Asp Lys Thr Val
                        210                 215                 220

Glu Arg Lys Cys Cys Val Glu Cys Pro Pro Cys Pro Ala Pro Pro Val
        225                 230                 235                 240

Ala Gly Pro Ser Val Phe Leu Phe Pro Pro Lys Pro Lys Asp Thr Leu
                        245                 250                 255

Met Ile Ser Arg Thr Pro Glu Val Thr Cys Val Val Val Asp Val Ser
                        260                 265                 270

His Glu Asp Pro Glu Val Gln Phe Asn Trp Tyr Val Asp Gly Val Glu
                        275                 280                 285

Val His Asn Ala Lys Thr Lys Pro Arg Glu Glu Gln Phe Asn Ser Thr
                        290                 295                 300

Phe Arg Val Val Ser Val Leu Thr Val Val His Gln Asp Trp Leu Asn
        305                 310                 315                 320

Gly Lys Glu Tyr Lys Cys Lys Val Ser Asn Lys Gly Leu Pro Ala Pro
                        325                 330                 335

Ile Glu Lys Thr Ile Ser Lys Thr Lys Gly Gln Pro Arg Glu Pro Gln
                        340                 345                 350

Val Tyr Thr Leu Pro Pro Ser Arg Glu Glu Met Thr Lys Asn Gln Val
                        355                 360                 365

Ser Leu Thr Cys Leu Val Lys Gly Phe Tyr Pro Ser Asp Ile Ala Val
        370                 375                 380

Glu Trp Glu Ser Asn Gly Gln Pro Glu Asn Asn Tyr Lys Thr Thr Pro
        385                 390                 395                 400

Pro Met Leu Asp Ser Asp Gly Ser Phe Phe Leu Tyr Ser Lys Leu Thr
                        405                 410                 415

Val Asp Lys Ser Arg Trp Gln Gln Gly Asn Val Phe Ser Cys Ser Val
                        420                 425                 430

Met His Glu Ala Leu His Asn His Tyr Thr Gln Lys Ser Leu Ser Leu
                        435                 440                 445

Ser Pro Gly
                450

<210> SEQ ID NO 43
<211> LENGTH: 451
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<223> OTHER INFORMATION: ADI-10089: heavy chain

<400> SEQUENCE: 43
```

| | | | | | | | | | | | | | | | |
|---|---|---|---|---|---|---|---|---|---|---|---|---|---|---|---|
| Gln | Leu | Gln | Leu | Gln | Glu | Ser | Gly | Pro | Gly | Leu | Val | Lys | Pro | Ser | Glu |
| 1 | | | | 5 | | | | | 10 | | | | | 15 | |
| Thr | Leu | Ser | Leu | Thr | Cys | Thr | Val | Ser | Gly | Gly | Ser | Ile | Gly | Ser | Ser |
| | | | 20 | | | | | 25 | | | | | 30 | | |
| Ser | Tyr | Tyr | Trp | Thr | Trp | Ile | Arg | Gln | Pro | Pro | Gly | Lys | Gly | Leu | Glu |
| | | 35 | | | | | 40 | | | | | 45 | | | |
| Trp | Ile | Gly | Ser | Ile | Asn | Tyr | Arg | Gly | Ser | Thr | Tyr | Tyr | Asn | Pro | Ser |
| 50 | | | | | 55 | | | | | 60 | | | | | |
| Leu | Lys | Ser | Arg | Val | Thr | Ile | Ser | Val | Asp | Thr | Ser | Lys | Asn | Gln | Phe |
| 65 | | | | | 70 | | | | | 75 | | | | | 80 |
| Ser | Leu | Lys | Leu | Ser | Ser | Val | Thr | Ala | Ala | Asp | Thr | Ala | Val | Tyr | Tyr |
| | | | | 85 | | | | | 90 | | | | | 95 | |
| Cys | Ala | Arg | Glu | Asn | Ser | Gly | Val | Val | Pro | Ala | Ala | Gly | Pro | Asn | Trp |
| | | | 100 | | | | | 105 | | | | | 110 | | |
| Phe | Asp | Pro | Trp | Gly | Gln | Gly | Thr | Leu | Val | Thr | Val | Ser | Ser | Ala | Ser |
| | | 115 | | | | | 120 | | | | | 125 | | | |
| Thr | Lys | Gly | Pro | Ser | Val | Phe | Pro | Leu | Ala | Pro | Cys | Ser | Arg | Ser | Thr |
| 130 | | | | | 135 | | | | | 140 | | | | | |
| Ser | Glu | Ser | Thr | Ala | Ala | Leu | Gly | Cys | Leu | Val | Lys | Asp | Tyr | Phe | Pro |
| 145 | | | | | 150 | | | | | 155 | | | | | 160 |
| Glu | Pro | Val | Thr | Val | Ser | Trp | Asn | Ser | Gly | Ala | Leu | Thr | Ser | Gly | Val |
| | | | 165 | | | | | 170 | | | | | 175 | | |
| His | Thr | Phe | Pro | Ala | Val | Leu | Gln | Ser | Ser | Gly | Leu | Tyr | Ser | Leu | Ser |
| | | | | 180 | | | | | 185 | | | | | 190 | |
| Ser | Val | Val | Thr | Val | Pro | Ser | Ser | Asn | Phe | Gly | Thr | Gln | Thr | Tyr | Thr |
| | | | 195 | | | | | 200 | | | | | 205 | | |
| Cys | Asn | Val | Asp | His | Lys | Pro | Ser | Asn | Thr | Lys | Val | Asp | Lys | Thr | Val |
| | 210 | | | | | 215 | | | | | 220 | | | | |
| Glu | Arg | Lys | Cys | Cys | Val | Glu | Cys | Pro | Pro | Cys | Pro | Ala | Pro | Pro | Val |
| 225 | | | | | 230 | | | | | 235 | | | | | 240 |
| Ala | Gly | Pro | Ser | Val | Phe | Leu | Phe | Pro | Pro | Lys | Pro | Lys | Asp | Thr | Leu |
| | | | | 245 | | | | | 250 | | | | | 255 | |
| Met | Ile | Ser | Arg | Thr | Pro | Glu | Val | Thr | Cys | Val | Val | Val | Asp | Val | Ser |
| | | | 260 | | | | | 265 | | | | | 270 | | |
| His | Glu | Asp | Pro | Glu | Val | Gln | Phe | Asn | Trp | Tyr | Val | Asp | Gly | Val | Glu |
| | | 275 | | | | | 280 | | | | | 285 | | | |
| Val | His | Asn | Ala | Lys | Thr | Lys | Pro | Arg | Glu | Glu | Gln | Phe | Asn | Ser | Thr |
| | 290 | | | | | 295 | | | | | 300 | | | | |
| Phe | Arg | Val | Val | Ser | Val | Leu | Thr | Val | Val | His | Gln | Asp | Trp | Leu | Asn |
| 305 | | | | | 310 | | | | | 315 | | | | | 320 |
| Gly | Lys | Glu | Tyr | Lys | Cys | Lys | Val | Ser | Asn | Lys | Gly | Leu | Pro | Ala | Pro |
| | | | 325 | | | | | 330 | | | | | 335 | | |
| Ile | Glu | Lys | Thr | Ile | Ser | Lys | Thr | Lys | Gly | Gln | Pro | Arg | Glu | Pro | Gln |
| | | | | 340 | | | | | 345 | | | | | 350 | |
| Val | Tyr | Thr | Leu | Pro | Pro | Ser | Arg | Glu | Glu | Met | Thr | Lys | Asn | Gln | Val |
| | | 355 | | | | | 360 | | | | | 365 | | | |
| Ser | Leu | Thr | Cys | Leu | Val | Lys | Gly | Phe | Tyr | Pro | Ser | Asp | Ile | Ala | Val |
| | 370 | | | | | 375 | | | | | 380 | | | | |

```
Glu Trp Glu Ser Asn Gly Gln Pro Glu Asn Asn Tyr Lys Thr Thr Pro
385                 390                 395                 400

Pro Met Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
        420                 425                 430

Met His Glu Ala Leu His Asn His Tyr Thr Gln Lys Ser Leu Ser Leu
        435                 440                 445

Ser Pro Gly
    450

<210> SEQ ID NO 44
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: ADI-10090: heavy chain

<400> SEQUENCE: 44

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Trp Ser Ser
            20                  25                  30

Ser Tyr Tyr Trp Thr Trp Ile Arg Gln Pro Pro Gly Lys Gly Leu Glu
        35                  40                  45

Trp Ile Gly Ser Ile Asn Tyr Arg Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asn Ser Gly Val Val Pro Ala Ala Gly Pro Asn Trp
            100                 105                 110

Phe Asp Pro Trp Gly Gln Gly Thr Leu Val Thr Val Ser Ser Ala Ser
        115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Asn Phe Gly Thr Gln Thr Tyr Thr
        195                 200                 205

Cys Asn Val Asp His Lys Pro Ser Asn Thr Lys Val Asp Lys Thr Val
    210                 215                 220

Glu Arg Lys Cys Cys Val Glu Cys Pro Pro Cys Pro Ala Pro Pro Val
225                 230                 235                 240

Ala Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270
```

His Glu Asp Pro Glu Val Gln Phe Asn Trp Tyr Val Asp Gly Val Glu
                275                 280                 285

Val His Asn Ala Lys Thr Lys Pro Arg Glu Glu Gln Phe Asn Ser Thr
            290                 295                 300

Phe Arg Val Val Ser Val Leu Thr Val Val His Gln Asp Trp Leu Asn
305                 310                 315                 320

Gly Lys Glu Tyr Lys Cys Lys Val Ser Asn Lys Gly Leu Pro Ala Pro
                325                 330                 335

Ile Glu Lys Thr Ile Ser Lys Thr Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Met Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly
    450

<210> SEQ ID NO 45
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain variable region FR1

<400> SEQUENCE: 45

Gln Leu Gln Leu Gln Glu Ser Gly Pro Gly Leu Val Lys Pro Ser Glu
1               5                   10                  15

Thr Leu Ser Leu Thr Cys Thr Val Ser Gly
            20                  25

<210> SEQ ID NO 46
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain variable region FR2

<400> SEQUENCE: 46

Trp Ile Arg Gln Pro Pro Gly Lys Gly Leu Glu Trp Ile Gly
1               5                   10

<210> SEQ ID NO 47
<211> LENGTH: 30
<212> TYPE: PRT
<213> ORGANISM: Artificial Sequence
<220> FEATURE:
<223> OTHER INFORMATION: Description of Artificial Sequence: Synthetic -continued

```
      polypeptide
<220> FEATURE:
<223> OTHER INFORMATION: heavy chain variable region FR3

<400> SEQUENCE: 47

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys
            20                  25                  30

<210> SEQ ID NO 48
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: heavy chain variable region FR4

<400> SEQUENCE: 48

Trp Gly Gln Gly Thr Leu Val Thr Val Ser Ser
1               5                   10

<210> SEQ ID NO 49
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: light chain variable region FR1

<400> SEQUENCE: 49

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 50
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: light chain variable region FR2

<400> SEQUENCE: 50

Trp Tyr Gln Gln Lys Pro Gly Gln Ala Pro Arg Leu Leu Ile Tyr
1               5                   10                  15

<210> SEQ ID NO 51
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: light chain variable region FR3

<400> SEQUENCE: 51

Gly Ile Pro Ala Arg Phe Ser Gly Ser Gly Ser Gly Thr Asp Phe Thr
1               5                   10                  15
```

```
Leu Thr Ile Ser Ser Leu Glu Pro Glu Asp Phe Ala Val Tyr Tyr Cys
                20                  25                  30
```

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: light chain variable region FR4

<400> SEQUENCE: 52

```
Phe Gly Gly Gly Thr Lys Val Glu Ile Lys
1               5                   10
```

<210> SEQ ID NO 53
<211> LENGTH: 692
<212> TYPE: PRT
<213> ORGANISM: Homo sapiens
<220> FEATURE:
<223> OTHER INFORMATION: amino acid sequence of PCSK9 antigen

<400> SEQUENCE: 53

```
Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
                20                  25                  30

Asp Glu Asp Gly Asp Tyr Glu Glu Leu Val Leu Ala Leu Arg Ser Glu
                35                  40                  45

Glu Asp Gly Leu Ala Glu Ala Pro Glu His Gly Thr Thr Ala Thr Phe
        50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
                100                 105                 110

His Val Phe His Gly Leu Leu Pro Gly Phe Leu Val Lys Met Ser Gly
            115                 120                 125

Asp Leu Leu Glu Leu Ala Leu Lys Leu Pro His Val Asp Tyr Ile Glu
        130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
                180                 185                 190

His Arg Glu Ile Glu Gly Arg Val Met Val Thr Asp Phe Glu Asn Val
            195                 200                 205

Pro Glu Glu Asp Gly Thr Arg Phe His Arg Gln Ala Ser Lys Cys Asp
        210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
                260                 265                 270
```

```
Lys Ser Gln Leu Val Gln Pro Val Gly Pro Leu Val Leu Leu Pro
        275                 280                 285
Leu Ala Gly Gly Tyr Ser Arg Val Leu Asn Ala Ala Cys Gln Arg Leu
290                 295                 300
Ala Arg Ala Gly Val Val Leu Val Thr Ala Ala Gly Asn Phe Arg Asp
305                 310                 315                 320
Asp Ala Cys Leu Tyr Ser Pro Ala Ser Ala Pro Glu Val Ile Thr Val
                325                 330                 335
Gly Ala Thr Asn Ala Gln Asp Gln Pro Val Thr Leu Gly Thr Leu Gly
                340                 345                 350
Thr Asn Phe Gly Arg Cys Val Asp Leu Phe Ala Pro Gly Glu Asp Ile
            355                 360                 365
Ile Gly Ala Ser Ser Asp Cys Ser Thr Cys Phe Val Ser Gln Ser Gly
            370                 375                 380
Thr Ser Gln Ala Ala Ala His Val Ala Gly Ile Ala Ala Met Met Leu
385                 390                 395                 400
Ser Ala Glu Pro Glu Leu Thr Leu Ala Glu Leu Arg Gln Arg Leu Ile
                405                 410                 415
His Phe Ser Ala Lys Asp Val Ile Asn Glu Ala Trp Phe Pro Glu Asp
                420                 425                 430
Gln Arg Val Leu Thr Pro Asn Leu Val Ala Ala Leu Pro Pro Ser Thr
            435                 440                 445
His Gly Ala Gly Trp Gln Leu Phe Cys Arg Thr Val Trp Ser Ala His
            450                 455                 460
Ser Gly Pro Thr Arg Met Ala Thr Ala Val Ala Arg Cys Ala Pro Asp
465                 470                 475                 480
Glu Glu Leu Leu Ser Cys Ser Ser Phe Ser Arg Ser Gly Lys Arg Arg
                485                 490                 495
Gly Glu Arg Met Glu Ala Gln Gly Gly Lys Leu Val Cys Arg Ala His
                500                 505                 510
Asn Ala Phe Gly Gly Glu Gly Val Tyr Ala Ile Ala Arg Cys Cys Leu
            515                 520                 525
Leu Pro Gln Ala Asn Cys Ser Val His Thr Ala Pro Pro Ala Glu Ala
            530                 535                 540
Ser Met Gly Thr Arg Val His Cys His Gln Gln Gly His Val Leu Thr
545                 550                 555                 560
Gly Cys Ser Ser His Trp Glu Val Glu Asp Leu Gly Thr His Lys Pro
                565                 570                 575
Pro Val Leu Arg Pro Arg Gly Gln Pro Asn Gln Cys Val Gly His Arg
                580                 585                 590
Glu Ala Ser Ile His Ala Ser Cys Cys His Ala Pro Gly Leu Glu Cys
            595                 600                 605
Lys Val Lys Glu His Gly Ile Pro Ala Pro Gln Glu Gln Val Thr Val
            610                 615                 620
Ala Cys Glu Glu Gly Trp Thr Leu Thr Gly Cys Ser Ala Leu Pro Gly
625                 630                 635                 640
Thr Ser His Val Leu Gly Ala Tyr Ala Val Asp Asn Thr Cys Val Val
                645                 650                 655
Arg Ser Arg Asp Val Ser Thr Thr Gly Ser Thr Ser Glu Gly Ala Val
                660                 665                 670
Thr Ala Val Ala Ile Cys Cys Arg Ser Arg His Leu Ala Gln Ala Ser
            675                 680                 685
```

```
Gln Glu Leu Gln
    690
```

<210> SEQ ID NO 54
<211> LENGTH: 668
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Antigen PCSK9-WT

<400> SEQUENCE: 54

```
Gln Glu Asp Glu Asp Gly Asp Tyr Glu Glu Leu Val Leu Ala Leu Arg
1               5                   10                  15

Ser Glu Glu Asp Gly Leu Ala Glu Ala Pro Glu His Gly Thr Thr Ala
            20                  25                  30

Thr Phe His Arg Cys Ala Lys Asp Pro Trp Arg Leu Pro Gly Thr Tyr
        35                  40                  45

Val Val Val Leu Lys Glu Glu Thr His Leu Ser Gln Ser Glu Arg Thr
    50                  55                  60

Ala Arg Arg Leu Gln Ala Gln Ala Ala Arg Arg Gly Tyr Leu Thr Lys
65                  70                  75                  80

Ile Leu His Val Phe His Gly Leu Leu Pro Gly Phe Leu Val Lys Met
                85                  90                  95

Ser Gly Asp Leu Leu Glu Leu Ala Leu Lys Leu Pro His Val Asp Tyr
            100                 105                 110

Ile Glu Glu Asp Ser Ser Val Phe Ala Gln Ser Ile Pro Trp Asn Leu
        115                 120                 125

Glu Arg Ile Thr Pro Pro Arg Tyr Arg Ala Asp Glu Tyr Gln Pro Pro
    130                 135                 140

Asp Gly Gly Ser Leu Val Glu Val Tyr Leu Leu Asp Thr Ser Ile Gln
145                 150                 155                 160

Ser Asp His Arg Glu Ile Glu Gly Arg Val Met Val Thr Asp Phe Glu
                165                 170                 175

Asn Val Pro Glu Glu Asp Gly Thr Arg Phe His Arg Gln Ala Ser Lys
            180                 185                 190

Cys Asp Ser His Gly Thr His Leu Ala Gly Val Val Ser Gly Arg Asp
        195                 200                 205

Ala Gly Val Ala Lys Gly Ala Ser Met Arg Ser Leu Arg Val Leu Asn
    210                 215                 220

Cys Gln Gly Lys Gly Thr Val Ser Gly Thr Leu Ile Gly Leu Glu Phe
225                 230                 235                 240

Ile Arg Lys Ser Gln Leu Val Gln Pro Val Gly Pro Leu Val Val Leu
                245                 250                 255

Leu Pro Leu Ala Gly Gly Tyr Ser Arg Val Leu Asn Ala Ala Cys Gln
            260                 265                 270

Arg Leu Ala Arg Ala Gly Val Val Leu Val Thr Ala Ala Gly Asn Phe
        275                 280                 285

Arg Asp Asp Ala Cys Leu Tyr Ser Pro Ala Ser Ala Pro Glu Val Ile
    290                 295                 300

Thr Val Gly Ala Thr Asn Ala Gln Asp Gln Pro Val Thr Leu Gly Thr
305                 310                 315                 320

Leu Gly Thr Asn Phe Gly Arg Cys Val Asp Leu Phe Ala Pro Gly Glu
                325                 330                 335
```

Asp Ile Ile Gly Ala Ser Ser Asp Cys Ser Thr Cys Phe Val Ser Gln
            340                 345                 350

Ser Gly Thr Ser Gln Ala Ala His Val Ala Gly Ile Ala Ala Met
        355                 360                 365

Met Leu Ser Ala Glu Pro Glu Leu Thr Leu Ala Glu Leu Arg Gln Arg
    370                 375                 380

Leu Ile His Phe Ser Ala Lys Asp Val Ile Asn Glu Ala Trp Phe Pro
385                 390                 395                 400

Glu Asp Gln Arg Val Leu Thr Pro Asn Leu Val Ala Ala Leu Pro Pro
                405                 410                 415

Ser Thr His Gly Ala Gly Trp Gln Leu Phe Cys Arg Thr Val Trp Ser
            420                 425                 430

Ala His Ser Gly Pro Thr Arg Met Ala Thr Ala Val Ala Arg Cys Ala
        435                 440                 445

Pro Asp Glu Glu Leu Leu Ser Cys Ser Ser Phe Ser Arg Ser Gly Lys
    450                 455                 460

Arg Arg Gly Glu Arg Met Glu Ala Gln Gly Gly Lys Leu Val Cys Arg
465                 470                 475                 480

Ala His Asn Ala Phe Gly Gly Glu Gly Val Tyr Ala Ile Ala Arg Cys
                485                 490                 495

Cys Leu Leu Pro Gln Ala Asn Cys Ser Val His Thr Ala Pro Pro Ala
            500                 505                 510

Glu Ala Ser Met Gly Thr Arg Val His Cys His Gln Gly His Gly His Val
        515                 520                 525

Leu Thr Gly Cys Ser Ser His Trp Glu Val Glu Asp Leu Gly Thr His
    530                 535                 540

Lys Pro Pro Val Leu Arg Pro Arg Gly Gln Pro Asn Gln Cys Val Gly
545                 550                 555                 560

His Arg Glu Ala Ser Ile His Ala Ser Cys Cys His Ala Pro Gly Leu
                565                 570                 575

Glu Cys Lys Val Lys Glu His Gly Ile Pro Ala Pro Gln Glu Gln Val
            580                 585                 590

Thr Val Ala Cys Glu Glu Gly Trp Thr Leu Thr Gly Cys Ser Ala Leu
        595                 600                 605

Pro Gly Thr Ser His Val Leu Gly Ala Tyr Ala Val Asp Asn Thr Cys
    610                 615                 620

Val Val Arg Ser Arg Asp Val Ser Thr Thr Gly Ser Thr Ser Glu Gly
625                 630                 635                 640

Ala Val Thr Ala Val Ala Ile Cys Cys Arg Ser Arg His Leu Ala Gln
                645                 650                 655

Ala Ser Gln Glu Leu Gln His His His His His
            660                 665

<210> SEQ ID NO 55
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Detection peptide

<400> SEQUENCE: 55

Asn Trp Phe Thr Phe Gly Gly Gly Thr Lys Glu Glu Thr His Leu Ser
1               5                   10                  15

```
Gln Ser Glu Arg
            20

<210> SEQ ID NO 56
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Detection peptide

<400> SEQUENCE: 56

Arg Gly Ser Thr Tyr Tyr Val Val Val Leu Lys Glu Glu Thr His Leu
1               5                   10                  15

<210> SEQ ID NO 57
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Detection peptide

<400> SEQUENCE: 57

Cys Ala Arg Glu Asn Ser Gly Val Val Pro Ala Ala Gly Pro Asn Trp
1               5                   10                  15

Arg Leu Pro Gly Thr Tyr Val Val Val Leu
            20                  25

<210> SEQ ID NO 58
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Detection peptide

<400> SEQUENCE: 58

Ser Cys Arg Ala Ser Gln Ser Val Ser Ser Tyr Gln Ala Gln Ala Ala
1               5                   10                  15

Arg Arg Gly Tyr Leu
            20

<210> SEQ ID NO 59
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Detection peptide

<400> SEQUENCE: 59

Ser Cys Arg Ala Ser Gln Ser Val Ser Ser Tyr Leu Gln Ala Gln Ala
1               5                   10                  15

Ala Arg Arg Gly Tyr
            20
```